(12) United States Patent
Shen et al.

(10) Patent No.: US 7,034,145 B2
(45) Date of Patent: *Apr. 25, 2006

(54) DIRECTIONALLY CLONED RANDOM CDNA EXPRESSION VECTOR LIBRARIES, COMPOSITIONS AND METHODS OF USE

(75) Inventors: Mary Shen, Newark, CA (US); Simon Yu, Newark, CA (US); Xian Wu, Redwood City, CA (US); Donald Payan, Hillsborough, CA (US)

(73) Assignee: Rigel Pharmaceuticals, Inc., South San Francisco, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 85 days.

This patent is subject to a terminal disclaimer.

(21) Appl. No.: 10/933,855

(22) Filed: Sep. 3, 2004

(65) Prior Publication Data

US 2005/0032110 A1    Feb. 10, 2005

Related U.S. Application Data

(63) Continuation of application No. 10/142,662, filed on May 8, 2002, now Pat. No. 6,808,906.

(51) Int. Cl.
    *C07H 21/04* (2006.01)
(52) U.S. Cl. .................... 536/24.3; 536/24.33
(58) Field of Classification Search ............. 536/24.3, 536/24.33
    See application file for complete search history.

(56) References Cited

U.S. PATENT DOCUMENTS 6,344,541 B1    2/2002    Bass et al.
6,808,906 B1 *  10/2004   Shen et al. ............ 435/91.41

OTHER PUBLICATIONS

Gossen, et al. "Tight Control of Gene Expression in Mammalian Cells by Tetracycline-Responsive Promoters", *Proc. Natl. Acad. Sci. USA*, (1992) vol. 89: 5547-5551.

Hofmann, et al. "Rapid Retroviral Delivery of Tetracycline-Inducible Genes in a Single Autoregulatory Cassette", *Proc. Natl. Acad. Sci. USA*, (1996) vol. 93: 5185-5190.

Lorens, et al. "Retroviral Delivery of Peptide Modulators of Cellular Functions", *Molecular Therapy*, (2000) vol. 1(5): 438-447.

Matz, et al. "Fluorescent Proteins from Nonbioluminescent Anthozoa Species", *Nature Biotechnology*, (1999) vol. 17: 969-973.

Xu, et al. "Dominant Effector Genetics in Mammalian Cells", *Nature Genetics*, (2001) vol. 27:23-29.

* cited by examiner

*Primary Examiner*—James Ketter
(74) *Attorney, Agent, or Firm*—James S. Keddie; Carol L. Francis; James J. Diehl

(57) ABSTRACT

The present invention provides random cDNA expression vector libraries, comprising expression vectors which comprise random cDNAs positioned in sense orientation. Also provided are random cDNA expression vector libraries, comprising expression vectors which comprise random cDNAs positioned in antisense orientation. Methods for producing these libraries through directional cloning of random cDNAs are also provided. Also provided herein are methods of using these libraries to screen for agents capable of modulating cell phenotype in desirable ways.

8 Claims, 4 Drawing Sheets

For example:

SfiIANB Adaptor (For random directional library construction)

```
                    SfiIA
5'p- CCGCCTCGGCCAGTGGCCGTA A- 3'
3' - GGCGGAGCCGGTCACCGGC-p-   5'
     Partial SfiIB
```

↓ Ligate to cDNA

```
     SfiIA
5'- p-CGGCCACTGGCCGAGGCGG- ds cDNA  GG -CCGCCTCGGCCAGTGGCCGTAA-3'
3'-AATGCCGGTGACCGGCTCCGCC-  NNNNNNCC -GGCGGAGCCGGTCACCGGC-p- 5'
                                                SfiIB
```

↓ Digest by SfiI

```
     SfiIA                              SfiIB
5'-p- CGGCCACTGGCCGAGGCGG- ds cDNA  GG -CCGCCT-3'
3'-AATGCCGGTGACCGGCTCCGCC-  NNNNNNCC -GGC    -5'
```

↓ Ligate to Vector

```
           SfiIA
Vector -GGCCATTACGGCCACTGGCCGAGGCGG-  ds cDNA GG -CCGCCTCGGCC- Vector
       -CCGGTAATGCCGGTGACCGGCTCCGCC-  NNNNNNCC -GGCGGAGCCGG-
                                                  SfiIB
```

Note: 1. SfiI restriction endonuclease    5'...GGCCNNNNNGGCC...3'
                                          3'...CCGGNNNNNCCGG...5'

2. SfiI random cDNA synthesis primer:   5'-CCNNNNNNN-3'

3. Vector: (have two SfiI digested sites which should match to two SfiI sites of cDNA)

```
5'-......GGCCATTACGGCC.........GGCCGCCTCGGCC......-3'   (Vector before cut)
3'-      CCGGTAATGCCGG         CCGGCGGAGCCGG      -5'
```

↓ Digest by SfiI and Purify

```
5'-........GGCCATTA -3'       5'- CGGCC......3'   (Vector)
3'-........CCGGT    -5'       3'-GGAGCCGG.......5'
```

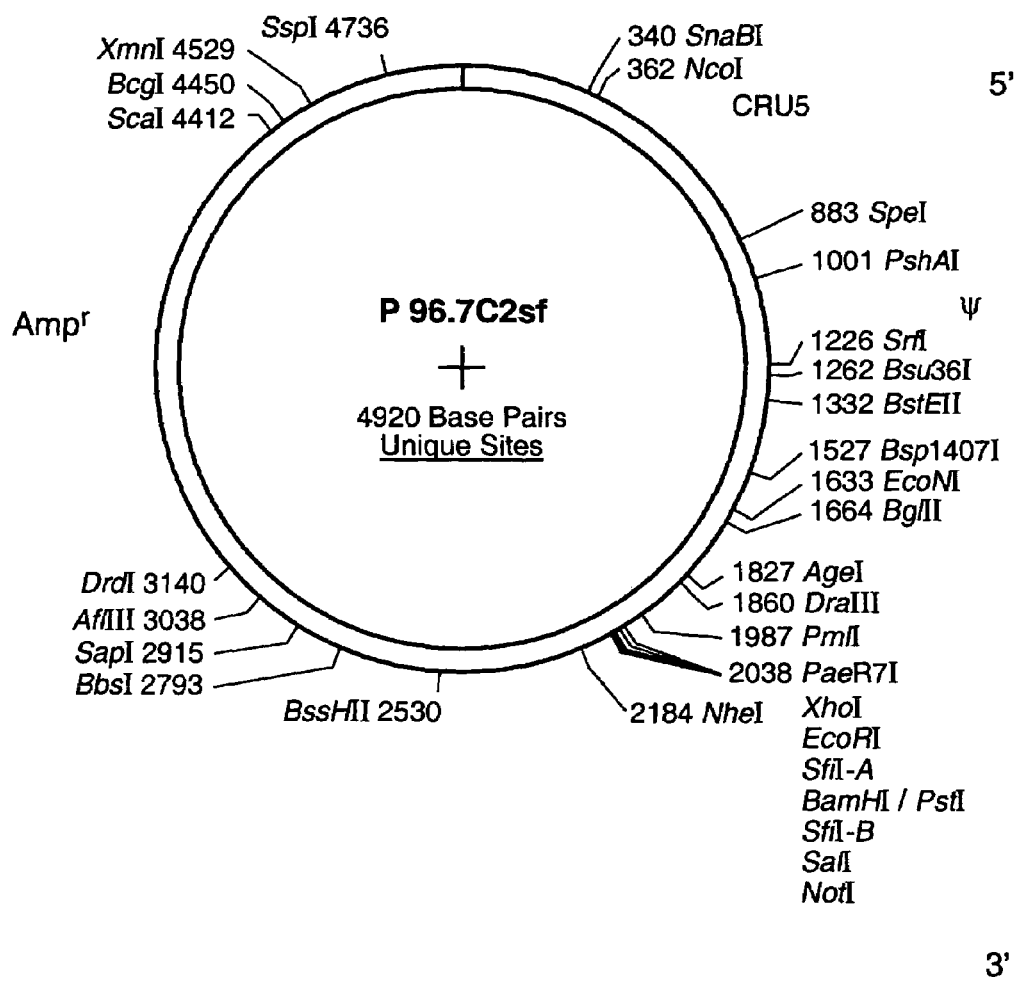
FIG._2

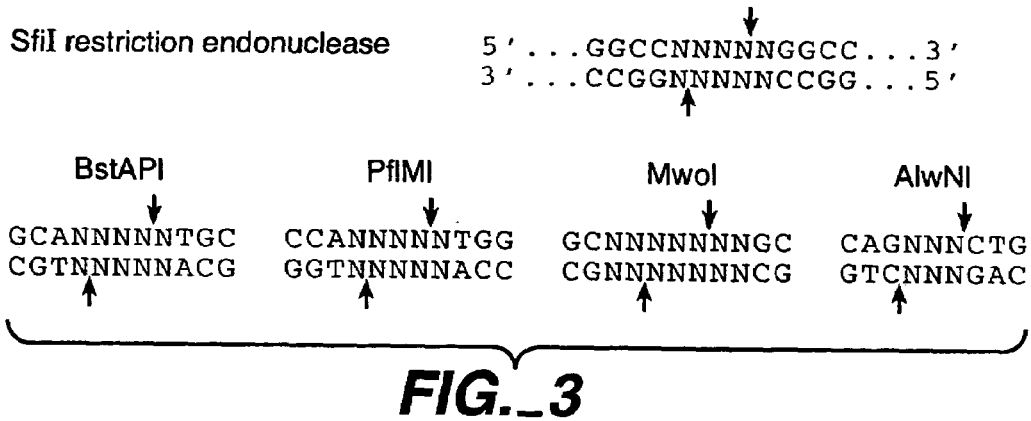
FIG._3
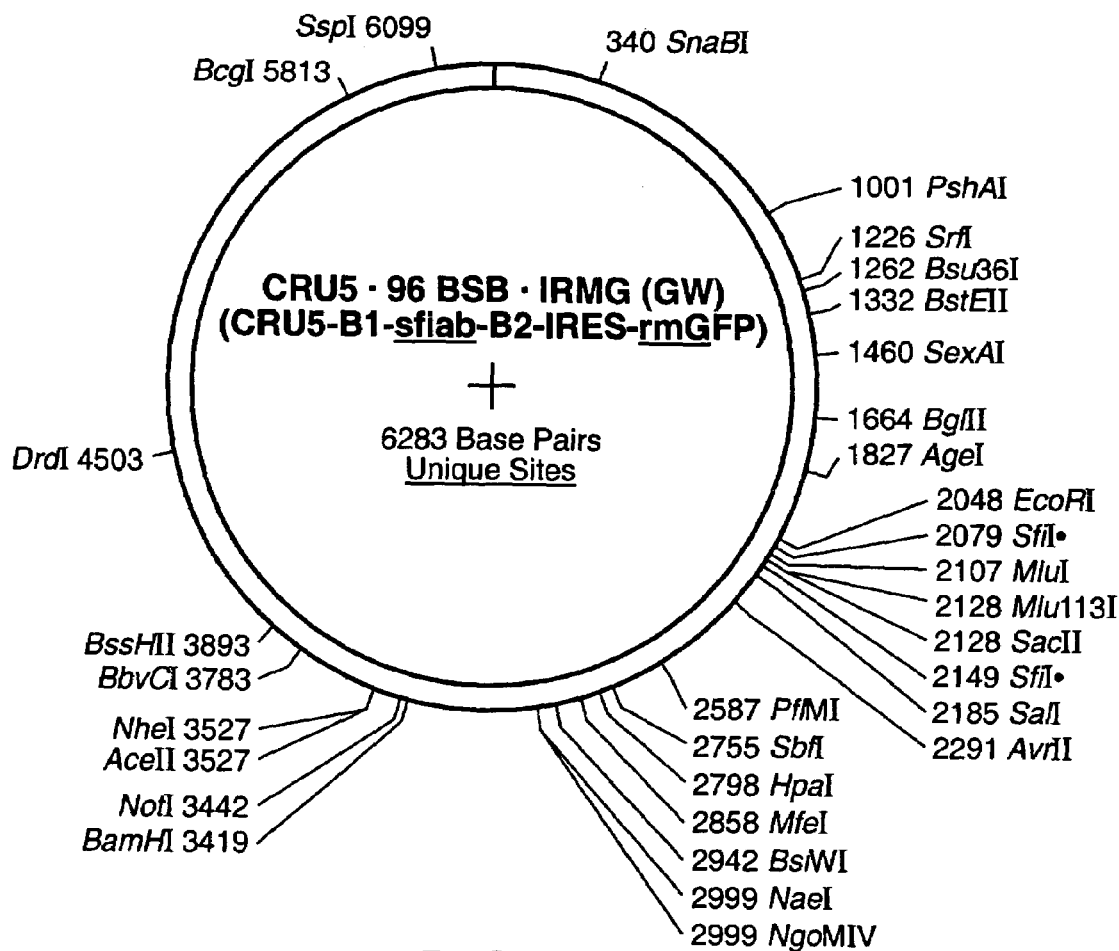
FIG._5

Jurkat Cells pTRAsf Random Directional Cloned cDNA Library Contruction
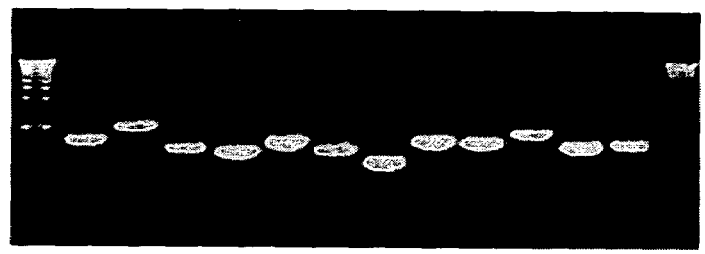
12 out of 12 Clones with cDNA Insert.
The average cDNA size is 1.4Kb.
*FIG._4*

SEQUENCE LISTING

<160> NUMBER OF SEQ ID NOS: 53

<210> SEQ ID NO 1
<211> LENGTH: 22
<212> TYPE: DNA
<213> ORGANISM: Artificial sequence
<220> FEATURE:
<223> OTHER INFORMATION: synthetic

<400> SEQUENCE: 1
ccgcctcggc cagtggccgt aa                                              22

<210> SEQ ID NO 2
<211> LENGTH: 19
<212> TYPE: DNA
<213> ORGANISM: Artificial sequence
<220> FEATURE:
<223> OTHER INFORMATION: synthetic

<400> SEQUENCE: 2
cggccactgg ccgaggcgg                                                  19

<210> SEQ ID NO 3
<211> LENGTH: 22
<212> TYPE: DNA
<213> ORGANISM: Artificial sequence
<220> FEATURE:
<223> OTHER INFORMATION: synthetic

<400> SEQUENCE: 3
ccgcctcggc cagtggccgt aa                                              22

<210> SEQ ID NO 4
<211> LENGTH: 19
<212> TYPE: DNA
<213> ORGANISM: Artificial sequence
<220> FEATURE:
<223> OTHER INFORMATION: synthetic

<400> SEQUENCE: 4
cggccactgg ccgaggcgg                                                  19

<210> SEQ ID NO 5
<211> LENGTH: 27
<212> TYPE: DNA
<213> ORGANISM: Artificial sequence
<220> FEATURE:
<223> OTHER INFORMATION: synthetic

<400> SEQUENCE: 5
ggccattacg gccactggcc gaggcgg                                         27

<210> SEQ ID NO 6
<211> LENGTH: 11
<212> TYPE: DNA
<213> ORGANISM: Artificial sequence
<220> FEATURE:
<223> OTHER INFORMATION: synthetic

<400> SEQUENCE: 6
ccgcctcggc c                                                          11

<210> SEQ ID NO 7
<211> LENGTH: 13

```
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (5)..(9)
<223> OTHER INFORMATION: "n" at positions 5-9 denotes any nucleotide,
      preferably a nucleotide selected from the group consisting of
      dAMP, dTMP, dGMP, dCMP, or analogs thereof

<400> SEQUENCE: 7
ggccnnnnng gcc                                                         13

<210> SEQ ID NO 8
<211> LENGTH: 13
<212> TYPE: DNA
<213> ORGANISM: Artificial sequence
<220> FEATURE:
<223> OTHER INFORMATION: synthetic

<400> SEQUENCE: 8
ggccattacg gcc                                                         13

<210> SEQ ID NO 9
<211> LENGTH: 13
<212> TYPE: DNA
<213> ORGANISM: Artificial sequence
<220> FEATURE:
<223> OTHER INFORMATION: synthetic

<400> SEQUENCE: 9
ggccgcctcg gcc                                                         13

<210> SEQ ID NO 10
<211> LENGTH: 12
<212> TYPE: DNA
<213> ORGANISM: Artificial sequence
<220> FEATURE:
<223> OTHER INFORMATION: synthetic

<400> SEQUENCE: 10
cctagttatt aa                                                          12

<210> SEQ ID NO 11
<211> LENGTH: 12
<212> TYPE: DNA
<213> ORGANISM: Artificial sequence
<220> FEATURE:
<223> OTHER INFORMATION: synthetic

<400> SEQUENCE: 11
cttgttctat gc                                                          12

<210> SEQ ID NO 12
<211> LENGTH: 68
<212> TYPE: DNA
<213> ORGANISM: Artificial sequence
<220> FEATURE:
<223> OTHER INFORMATION: synthetic

<400> SEQUENCE: 12
ctcgaggttg gaattcggcc attatggcct gcaggatccg gccgcctcgg cccagtcgac       60
gcggccgc                                                               68

<210> SEQ ID NO 13
```

```
<211> LENGTH: 11
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (4)..(8)
<223> OTHER INFORMATION: "n" at positions 4-8 can be any base

<400> SEQUENCE: 13
gcannnnntg c                                                            11

<210> SEQ ID NO 14
<211> LENGTH: 11
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (4)..(8)
<223> OTHER INFORMATION: "n" at positions 4-8 can be any base

<400> SEQUENCE: 14
ccannnnntg g                                                            11

<210> SEQ ID NO 15
<211> LENGTH: 11
<212> TYPE: DNA
<213> ORGANISM: Artificial sequence
<220> FEATURE:
<223> OTHER INFORMATION: aynthetic
<220> FEATURE:
<221> NAME/KEY: misc_feature
<222> LOCATION: (3)..(9)
<223> OTHER INFORMATION: "n" at positions 3-9 can be any base

<400> SEQUENCE: 15
gcnnnnnnng c                                                            11

<210> SEQ ID NO 16
<211> LENGTH: 9
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (4)..(6)
<223> OTHER INFORMATION: "n" at positions 4-6 can be any base

<400> SEQUENCE: 16 cagnnnctg                                                                9

<210> SEQ ID NO 17
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(7)
<223> OTHER INFORMATION: "n" at positions 3-7 are each any nucleotide
      selected from dAMP, dTMP, dGMP, dCMP, or analogs thereof
<220> FEATURE:
<221> NAME/KEY: misc_feature
<222> LOCATION: (12)..(20)
<223> OTHER INFORMATION: "n" at positions 12-20 indicates a number of
      any nucleotides from about 1 to about 9 nucleotides, with 3 being
```

```
            the most preferred
<220> FEATURE:
<221> NAME/KEY: misc_feature
<222> LOCATION: (25)..(28)
<223> OTHER INFORMATION: "n" at positions 25-28 are each any nucleotide
      selected from dAMP, dTMP, dGMP, dCMP, or analogs thereof

<400> SEQUENCE: 17 ccnnnnggc cnnnnnnnnn ggccnnnn                                         28

<210> SEQ ID NO 18
<211> LENGTH: 13
<212> TYPE: DNA
<213> ORGANISM: Artificial sequence
<220> FEATURE:
<223> OTHER INFORMATION: synthetic

<400> SEQUENCE: 18
ggccgaggcg gcc                                                        13

<210> SEQ ID NO 19
<211> LENGTH: 13
<212> TYPE: DNA
<213> ORGANISM: Artificial sequence
<220> FEATURE:
<223> OTHER INFORMATION: synthetic

<400> SEQUENCE: 19
ggccgtaatg gcc                                                        13

<210> SEQ ID NO 20
<211> LENGTH: 28
<212> TYPE: DNA
<213> ORGANISM: Artificial sequence
<220> FEATURE:
<223> OTHER INFORMATION: synthetic
<220> FEATURE:
<221> NAME/KEY: misc_feature
<222> LOCATION: (3)..(7)
<223> OTHER INFORMATION: "n" at positions 3-7 are each any nucleotide,
      prefereably selected from the group consisting of dAMP, dTMP,
      dGMP, dCMP, or analogs thereof
<220> FEATURE:
<221> NAME/KEY: misc_feature
<222> LOCATION: (12)..(25)
<223> OTHER INFORMATION: "n" at positions 12-25 may be any nucleotide,
      from about 4 to about 14 nucleotides, more preferably about 6 to
      about 14, more preferably about 8 to about 14
<220> FEATURE:
<221> NAME/KEY: misc_feature
<222> LOCATION: (26)..(28)
<223> OTHER INFORMATION: "n" at positions 26-28 are each any nucleotide,
      preferably from the group dAMP, dTMP, dGMP, dCMP, or analogs
      thereof

<400> SEQUENCE: 20 ccnnnnggc cnnnnnnnnn nnnnnnnn                                         28

<210> SEQ ID NO 21
<211> LENGTH: 8
<212> TYPE: PRT
<213> ORGANISM: Simian virus 40

<400> SEQUENCE: 21

Pro Lys Lys Lys Lys Arg Lys Val
1               5

<210> SEQ ID NO 22
<211> LENGTH: 6
```

```
<212> TYPE: PRT
<213> ORGANISM: Homo sapiens

<400> SEQUENCE: 22

Ala Arg Arg Arg Arg Pro
1               5

<210> SEQ ID NO 23
<211> LENGTH: 10
<212> TYPE: PRT
<213> ORGANISM: Mus musculus

<400> SEQUENCE: 23

Glu Glu Val Gln Arg Lys Arg Gln Lys Leu
1               5                   10

<210> SEQ ID NO 24
<211> LENGTH: 9
<212> TYPE: PRT
<213> ORGANISM: Mus musculus

<400> SEQUENCE: 24

Glu Glu Lys Arg Lys Arg Thr Tyr Glu
1               5

<210> SEQ ID NO 25
<211> LENGTH: 20
<212> TYPE: PRT
<213> ORGANISM: Xenopus laevis

<400> SEQUENCE: 25

Ala Val Lys Arg Pro Ala Ala Thr Lys Lys Ala Gly Gln Ala Lys Lys
1               5                   10                  15

Lys Lys Leu Asp
            20

<210> SEQ ID NO 26
<211> LENGTH: 31
<212> TYPE: PRT
<213> ORGANISM: Mus musculus

<400> SEQUENCE: 26

Met Ala Ser Pro Leu Thr Arg Phe Leu Ser Leu Asn Leu Leu Leu Leu
1               5                   10                  15

Gly Glu Ser Ile Leu Gly Ser Gly Glu Ala Lys Pro Gln Ala Pro
            20                  25                  30

<210> SEQ ID NO 27
<211> LENGTH: 21
<212> TYPE: PRT
<213> ORGANISM: Homo sapiens

<400> SEQUENCE: 27

Met Ser Ser Phe Gly Tyr Arg Thr Leu Thr Val Ala Leu Phe Thr Leu
1               5                   10                  15

Ile Cys Cys Pro Gly
            20

<210> SEQ ID NO 28
<211> LENGTH: 51
<212> TYPE: PRT
<213> ORGANISM: Mus musculus

<400> SEQUENCE: 28
```

```
Pro Gln Arg Pro Glu Asp Cys Arg Pro Arg Gly Ser Val Lys Gly Thr
1               5                   10                  15

Gly Leu Asp Phe Ala Cys Asp Ile Tyr Ile Trp Ala Pro Leu Ala Gly
            20                  25                  30

Ile Cys Val Ala Leu Leu Ser Leu Ile Ile Thr Leu Ile Cys Tyr
        35                  40                  45

His Ser Arg
    50

<210> SEQ ID NO 29
<211> LENGTH: 33
<212> TYPE: PRT
<213> ORGANISM: Homo sapiens

<400> SEQUENCE: 29

Met Val Ile Ile Val Thr Val Val Ser Val Leu Leu Ser Leu Phe Val
1               5                   10                  15

Thr Ser Val Leu Leu Cys Phe Ile Phe Gly Gln His Leu Arg Gln Gln
            20                  25                  30

Arg

<210> SEQ ID NO 30
<211> LENGTH: 37
<212> TYPE: PRT
<213> ORGANISM: Rattus sp.

<400> SEQUENCE: 30

Pro Asn Lys Gly Ser Gly Thr Thr Ser Gly Thr Thr Arg Leu Leu Ser
1               5                   10                  15

Gly His Thr Cys Phe Thr Leu Thr Gly Leu Leu Gly Thr Leu Val Thr
            20                  25                  30

Met Gly Leu Leu Thr
        35

<210> SEQ ID NO 31
<211> LENGTH: 14
<212> TYPE: PRT
<213> ORGANISM: Gallus gallus

<400> SEQUENCE: 31

Met Gly Ser Ser Lys Ser Lys Pro Lys Asp Pro Ser Gln Arg
1               5                   10

<210> SEQ ID NO 32
<211> LENGTH: 26
<212> TYPE: PRT
<213> ORGANISM: Homo sapiens

<400> SEQUENCE: 32

Leu Leu Gln Arg Leu Phe Ser Arg Gln Asp Cys Cys Gly Asn Cys Ser
1               5                   10                  15

Asp Ser Glu Glu Glu Leu Pro Thr Arg Leu
            20                  25

<210> SEQ ID NO 33
<211> LENGTH: 20
<212> TYPE: PRT
<213> ORGANISM: Rattus norvegicus

<400> SEQUENCE: 33
```

-continued

```
Lys Gln Phe Arg Asn Cys Met Leu Thr Ser Leu Cys Cys Gly Lys Asn
1               5                   10                  15

Pro Leu Gly Asp
            20

<210> SEQ ID NO 34
<211> LENGTH: 19
<212> TYPE: PRT
<213> ORGANISM: Homo sapiens

<400> SEQUENCE: 34

Leu Asn Pro Pro Asp Glu Ser Gly Pro Gly Cys Met Ser Cys Lys Cys
1               5                   10                  15

Val Leu Ser

<210> SEQ ID NO 35
<211> LENGTH: 5
<212> TYPE: PRT
<213> ORGANISM: Artificial sequence
<220> FEATURE:
<223> OTHER INFORMATION: lysosomal degradation sequence

<400> SEQUENCE: 35

Lys Phe Glu Arg Gln
1               5

<210> SEQ ID NO 36
<211> LENGTH: 36
<212> TYPE: PRT
<213> ORGANISM: Cricetulus griseus

<400> SEQUENCE: 36

Met Leu Ile Pro Ile Ala Gly Phe Phe Ala Leu Ala Gly Leu Val Leu
1               5                   10                  15

Ile Val Leu Ile Ala Tyr Leu Ile Gly Arg Lys Arg Ser His Ala Gly
            20                  25                  30

Tyr Gln Thr Ile
        35

<210> SEQ ID NO 37
<211> LENGTH: 35
<212> TYPE: PRT
<213> ORGANISM: Homo sapiens

<400> SEQUENCE: 37

Leu Val Pro Ile Ala Val Gly Ala Ala Leu Ala Gly Val Leu Ile Leu
1               5                   10                  15

Val Leu Leu Ala Tyr Phe Ile Gly Leu Lys His His His Ala Gly Tyr
            20                  25                  30

Glu Gln Phe
        35

<210> SEQ ID NO 38
<211> LENGTH: 27
<212> TYPE: PRT
<213> ORGANISM: Saccharomyces cerevisiae

<400> SEQUENCE: 38

Met Leu Arg Thr Ser Ser Leu Phe Thr Arg Arg Val Gln Pro Ser Leu
1               5                   10                  15

Phe Ser Arg Asn Ile Leu Arg Leu Gln Ser Thr
            20                  25
```

<210> SEQ ID NO 39
<211> LENGTH: 25
<212> TYPE: PRT
<213> ORGANISM: Saccharomyces cerevisiae

<400> SEQUENCE: 39

Met Leu Ser Leu Arg Gln Ser Ile Arg Phe Phe Lys Pro Ala Thr Arg
1               5                   10                  15

Thr Leu Cys Ser Ser Arg Tyr Leu Leu
            20                  25

<210> SEQ ID NO 40
<211> LENGTH: 64
<212> TYPE: PRT
<213> ORGANISM: Saccharomyces cerevisiae

<400> SEQUENCE: 40

Met Phe Ser Met Leu Ser Lys Arg Trp Ala Gln Arg Thr Leu Ser Lys
1               5                   10                  15

Ser Phe Tyr Ser Thr Ala Thr Gly Ala Ala Ser Lys Ser Gly Lys Leu
            20                  25                  30

Thr Gln Lys Leu Val Thr Ala Gly Val Ala Ala Ala Gly Ile Thr Ala
        35                  40                  45

Ser Thr Leu Leu Tyr Ala Asp Ser Leu Thr Ala Glu Ala Met Thr Ala
    50                  55                  60

<210> SEQ ID NO 41
<211> LENGTH: 41
<212> TYPE: PRT
<213> ORGANISM: Saccharomyces cerevisiae

<400> SEQUENCE: 41

Met Lys Ser Phe Ile Thr Arg Asn Lys Thr Ala Ile Leu Ala Thr Val
1               5                   10                  15

Ala Ala Thr Gly Thr Ala Ile Gly Ala Tyr Tyr Tyr Tyr Asn Gln Leu
            20                  25                  30

Gln Gln Gln Gln Gln Arg Gly Lys Lys
        35                  40

<210> SEQ ID NO 42
<211> LENGTH: 4
<212> TYPE: PRT
<213> ORGANISM: Homo sapiens

<400> SEQUENCE: 42

Lys Asp Glu Leu
1

<210> SEQ ID NO 43
<211> LENGTH: 15
<212> TYPE: PRT
<213> ORGANISM: Homo sapiens

<400> SEQUENCE: 43

Leu Tyr Leu Ser Arg Arg Ser Phe Ile Asp Glu Lys Lys Met Pro
1               5                   10                  15

<210> SEQ ID NO 44
<211> LENGTH: 15
<212> TYPE: PRT
<213> ORGANISM: Homo sapiens

<400> SEQUENCE: 44

Leu Thr Glu Pro Thr Gln Pro Thr Arg Asn Gln Cys Cys Ser Asn
1               5                   10                  15

<210> SEQ ID NO 45
<211> LENGTH: 9
<212> TYPE: PRT
<213> ORGANISM: Unknown
<220> FEATURE:
<223> OTHER INFORMATION: cyclin B1 destruction sequence

<400> SEQUENCE: 45

Arg Thr Ala Leu Gly Asp Ile Gly Asn
1               5

<210> SEQ ID NO 46
<211> LENGTH: 20
<212> TYPE: PRT
<213> ORGANISM: Unknown
<220> FEATURE:
<223> OTHER INFORMATION: signal sequence from Interleukin-2

<400> SEQUENCE: 46

Met Tyr Arg Met Gln Leu Leu Ser Cys Ile Ala Leu Ser Leu Ala Leu
1               5                   10                  15

Val Thr Asn Ser
            20

<210> SEQ ID NO 47
<211> LENGTH: 29
<212> TYPE: PRT
<213> ORGANISM: Homo sapiens

<400> SEQUENCE: 47

Met Ala Thr Gly Ser Arg Thr Ser Leu Leu Leu Ala Phe Gly Leu Leu
1               5                   10                  15

Cys Leu Pro Trp Leu Gln Glu Gly Ser Ala Phe Pro Thr
            20                  25

<210> SEQ ID NO 48
<211> LENGTH: 27
<212> TYPE: PRT
<213> ORGANISM: Homo sapiens

<400> SEQUENCE: 48

Met Ala Leu Trp Met Arg Leu Leu Pro Leu Leu Ala Leu Leu Ala Leu
1               5                   10                  15

Trp Gly Pro Asp Pro Ala Ala Ala Phe Val Asn
            20                  25

<210> SEQ ID NO 49
<211> LENGTH: 18
<212> TYPE: PRT
<213> ORGANISM: Influenza virus

<400> SEQUENCE: 49

Met Lys Ala Lys Leu Leu Val Leu Leu Tyr Ala Phe Val Ala Gly Asp
1               5                   10                  15

Gln Ile

<210> SEQ ID NO 50
<211> LENGTH: 24

```
-continued

<212> TYPE: PRT
<213> ORGANISM: Unknown
<220> FEATURE:
<223> OTHER INFORMATION: signal sequence from Interleukin-4

<400> SEQUENCE: 50

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 51
<211> LENGTH: 10
<212> TYPE: PRT
<213> ORGANISM: Artificial sequence
<220> FEATURE:
<223> OTHER INFORMATION: stability sequence
<220> FEATURE:
<221> NAME/KEY: MISC_FEATURE
<222> LOCATION: (3)..(6)
<223> OTHER INFORMATION: "Xaa" at positions 3 to 6 can be at least 4 of
      any amino acids

<400> SEQUENCE: 51

Met Gly Xaa Xaa Xaa Xaa Gly Gly Pro Pro
1               5                   10

<210> SEQ ID NO 52
<211> LENGTH: 5
<212> TYPE: PRT
<213> ORGANISM: Artificial sequence
<220> FEATURE:
<223> OTHER INFORMATION: linker consensus sequence

<400> SEQUENCE: 52

Gly Ser Gly Gly Ser
1               5

<210> SEQ ID NO 53
<211> LENGTH: 4
<212> TYPE: PRT
<213> ORGANISM: Artificial sequence
<220> FEATURE:
<223> OTHER INFORMATION: linker consensus sequence

<400> SEQUENCE: 53

Gly Gly Gly Ser
1
```

DIRECTIONALLY CLONED RANDOM cDNA EXPRESSION VECTOR LIBRARIES, COMPOSITIONS AND METHODS OF USE

CROSS REFERENCE

This application is a continuation of U.S. patent application Ser. No. 10/142,662, filed May 8, 2002 now U.S. Pat. No. 6,808,906, the disclosure of which is herein incorporated by reference in entirety and to which application priority is claimed.

FIELD OF THE INVENTION

The present invention relates generally to the field of molecular biology and in particular to the creation and use of gene libraries containing cloned cDNAs that encode expressed genes.

BACKGROUND OF THE INVENTION

A common practice in molecular biology is to create "gene libraries," which are collections of cloned fragments of DNA that represent genetic information in an organism, tissue or cell type. To construct a library, desired DNA fragments are prepared and inserted by molecular techniques into self-replicating units generally called cloning vectors. Each DNA fragment is therefore represented as part of an individual molecule, which can be reproduced in a single bacterial colony or bacteriophage plaque. Individual clones of interest can be identified by various screening methods, and then grown and purified in large quantities to allow study of gene organization, structure and function.

Only a small fraction of the genetic information for an organism is actually used in an individual cell or tissue at a particular time. A cDNA library is a type of gene library in which only DNA for actively expressed genes is cloned. These active genes can be selectively cloned over silent genes because the DNA for active genes is transcribed into messenger RNA (mRNA) as part of the pathway by which proteins are made. RNA molecules are polar in nature, i.e. the constituent nucleoside bases are linked via phosphodiester bonds between the 3' ribosyl position of one nucleoside and the 5' ribosyl position on the following nucleoside. RNA is synthesized in the 5' to 3' direction, and mRNAs are read by ribosomes in the same direction, such that proteins are synthesized from N-terminus to C-terminus. Over the past decade, cDNA libraries have become the standard source from which thousands of genes have been isolated for further study.

cDNA libraries may be expression libraries, whereby the cDNAs are transcribed and translated, resulting in the production of polypeptides corresponding to mRNA-encoded proteins. The activity of cDNA expression products may be assayed, and the function of corresponding mRNAs and proteins encoded thereby may be determined.

Full length cDNA, which comprises the entire open reading frame (ORF) of an mRNA, is desirable for many applications. Alternatively, partial cDNA and cDNA fragments are useful in some applications, for example, identifying functional domains within proteins. Interestingly, microdomains can exert unique biological effects compared to the parental molecules from which they are derived (Lorens et. al., Mol. Therapy, 1:438–447, 2000). The ability to express protein microdomains can be a powerful means to subtly perturb cellular physiology in manners that reveal new paths for therapeutic intervention.

The use of retroviruses is desirable for the stable transduction of genetic material into host cells, particularly host cells which are poorly transfectable, such as myoblasts and lymphocytes.

One object of the present invention is to provide methods and compositions for stably expressing genetic effectors, comprising random cDNAs, in host cells.

An additional object of the invention is to provide methods and compositions to screen for genetic effectors, comprising random cDNAs, that alter cell phenotype in a desirable way.

SUMMARY OF THE INVENTION

The present invention provides methods and compositions for producing directional random cDNA libraries. Directional random cDNA libraries comprising pluralities of directional random cDNA expression vectors, and methods of using these libraries, are also provided.

In one aspect of the invention, directional random cDNA expression vector libraries are provided. Each library comprises a plurality of directional random cDNA expression vectors. In a preferred embodiment, libraries comprising expression vectors with random cDNA in sense orientation are provided. In another embodiment, libraries comprising expression vectors with random cDNA in antisense orientation are provided. In another embodiment, libraries comprising a mixture of expression vectors with random cDNAs in sense orientation and antisense orientation are provided. As discussed below, the methods provided herein for making random cDNA libraries involve the directional cloning of random cDNAs into expression vectors. Accordingly, the orientation of a random cDNA in each vector is predetermined, facilitating construction of sense libraries, antisense libraries, and mixtures thereof. Such a scheme provides for the expression of antisense nucleic acid and nucleic acid corresponding in sequence to mRNA, as desired.

It will be understood that the cDNA libraries of the present invention comprise vectors, which comprise random cDNAs, which random cDNAs are directionally positioned in expression vectors in sense orientation, or antisense orientation. These libraries are sometimes referred to herein as directional random cDNA libraries. For the ease of description, the terms "directional" and "random" will often be omitted when referring herein to these libraries and methods of making the same.

In a preferred embodiment, the present invention provides cDNA expression vector libraries, each comprising a plurality of expression vectors, each vector comprising a) a first nucleic acid comprising a cDNA; b) a second nucleic acid which is a fusion partner; and c) a transcriptional regulatory sequence recognized by a host cell, wherein the first and second nucleic acids form a fusion nucleic acid which is operably linked to the transcriptional regulatory region (sometimes referred to herein as a transcriptional regulatory sequence). In some embodiments, the vectors also comprise a translational regulatory region (sometimes referred to herein as a translational regulatory sequence or start site) which forms part of the fusion nucleic acid and initiates translation of the fusion nucleic acid.

Preferred cDNAs for use in the present invention comprise sequences complementary to complete or near complete 5' mRNA ends, including native translational start sites, which facilitate translation of cDNA encoded transcript in a host cell.

Other cDNAs may be used however, as will be appreciated by those in the art. For example, cDNAs lacking native translation start sequences, and comprising sequences complementary to 3' mRNA ends also find use in some embodiments of the present invention.

In a preferred embodiment, the fusion partner encodes a detectable protein. In a preferred embodiment, the detectable protein is an autofluorescent protein. In a further preferred embodiment, the autofluorescent protein is a green fluorescent protein (GFP). In a further preferred embodiment, the autofluorescent protein is a GFP from Aequorea, or one of the well known variants thereof including red flourescent protein (RFP), blue fluorescent protein (BFP), and yellow fluorescent protein (YFP). In another further preferred embodiment, the autofluorescent protein is a GFP from *Renilla*. In another further preferred embodiment, the autofluorescent protein is a GFP from *Ptilosarcus*. In another preferred embodiment, the autofluorescent protein is a GFP homologue from *Anthozoa* species (Matz et al., Nat. Biotech., 17:96–973, 1999).

In a preferred embodiment, the first nucleic acid is fused to the 5' end of the second nucleic acid. The expression products of such a vector include a fusion nucleic acid wherein cDNA encoded sequence is located at the 5' end and nucleic acid sequence encoding detectable protein is located at the 3' end. Expression products also include a fusion protein that comprises an N-terminal polypeptide encoded by cDNA and a C-terminal polypeptide which is a detectable protein moiety. In embodiments where cDNA is inserted in antisense orientation, the expression products include a fusion nucleic acid wherein antisense nucleic acid is located at the 5' end and nucleic acid sequence encoding detectable protein is located at the 3' end.

In a preferred embodiment, the expression vector does not comprise a heterologous translation start site for the initiation of cDNA transcript translation.

In another embodiment, the expression vector comprises an heterologous translation start site for initiating translation of a cDNA transcript. In embodiments where cDNA is in antisense orientation, the heterologous translation start site provides for the translation of antisense cDNA transcripts. In embodiments where cDNA is in sense orientation, cDNA transcripts may be translated in frame or out of frame, depending on the positioning of the cDNA relative to the heterologous translation start site. cDNAs translated out of frame, and cDNA antisense transcripts, encode what are herein referred to as "random peptides".

Translation of cDNA transcripts out of frame may present internal "stop" codons (TAA, TGA, TAG), interrupting or inhibiting cDNA translation. Stop codons may also be encountered in antisense transcripts. For clarity of description, the occurrence of internal translational "stop" codons within cDNA antisense transcripts and cDNAs translated out of frame is not treated in every relevant embodiment discussed herein, though it is understood that such "stop" codons may occur.

In one embodiment, the first nucleic acid is fused to the 3' end of the second nucleic acid. The expression products of such a vector include a fusion nucleic acid wherein cDNA encoded sequence is located at the 3' end and nucleic acid sequence encoding detectable protein is located at the 5' end. Expression products may also include a fusion protein that comprises a C-terminal polypeptide encoded by cDNA and an N-terminal polypeptide which is a detectable protein moiety. Some cDNAs will be translated in frame while others will translate out of frame, encoding what are herein referred to as "random peptides". In embodiments where cDNA is in antisense orientation, the expression products include a fusion nucleic acid wherein antisense nucleic acid is located at the 3' end and nucleic acid sequence encoding detectable protein is located at the 5' end. In addition, antisense transcripts may be translated yielding fusion proteins comprising an N-terminus polypeptide which is a detectable protein moiety and a C-terminus peptide which is encoded by antisense cDNA transcript.

In another embodiment, the first nucleic acid is positioned within the second nucleic acid (e.g., the second nucleic acid comprises the first nucleic acid). Expression products of such vectors include fusion nucleic acids wherein cDNA-encoded sequence is located within nucleic acid sequence encoding detectable protein. Expression products also include fusion proteins that comprise cDNA-encoded peptides within detectable proteins, preferably in the surface exposed loop region of a detectable protein, as described herein. Some cDNAs will be translated in frame while others will translate out of frame, encoding what are referred to herein as random peptides. In embodiments where cDNA is inserted in antisense orientation, the expression products include fusion nucleic acids wherein antisense nucleic acid is located within nucleic acid sequence encoding detectable protein. In addition, antisense nucleic acids may be translated if stop codons are not encountered, yielding fusion proteins that comprise antisense encoded peptide within detectable protein.

In a preferred embodiment, expression vectors additionally comprise a third nucleic acid sequence, referred to herein as a linker, which is interposed between the first and second nucleic acids. In this embodiment, the linker may encode a linking peptide that joins cDNA encoded peptide to the detectable protein moiety in a fusion protein. Alternatively, as outlined, the linker may be a separation sequence that provides for the expression of separate cDNA encoded peptide and detectable protein moieties.

In a preferred embodiment, the linker connecting the first and second nucleic acids comprises an internal ribosome entry site (IRES). Such a linker may be used to fuse the first nucleic acid to the 5' end or the 3' end of the second nucleic acid. The expression products of such a vector include a fusion nucleic acid and two separate polypeptides translated from a fusion nucleic acid, particularly a first polypeptide which is encoded by a cDNA, and a second polypeptide which is a detectable protein.

In another embodiment, the linker connecting the first and second nucleic acids comprises a cleavage site. Such a linker may fuse the first nucleic acid to the 5' end or the 3' end of the second nucleic acid. The expression products of such a vector include a fusion nucleic acid, and a fusion protein wherein the cDNA-encoded polypeptide moiety and the detectable protein moiety are separated by an intervening cleavage site which is a polypeptide sequence that is recognized by a protease. This site provides for cleavage of the covalent peptide linkage which fuses the cDNA-encoded polypeptide moiety to the detectable protein moiety in the fusion protein and thereby provides for the expression of two separate polypeptides.

In another embodiment, the linker comprises a 2a sequence. Such a linker may fuse the first nucleic acid to the 5' end or the 3' end of the second nucleic acid. The expression products of such a vector include a fusion nucleic acid and two separate polypeptides translated from a fusion nucleic acid, particularly a first polypeptide which is encoded by a cDNA, and a second polypeptide which is a detectable protein.

In a preferred embodiment, cDNA expression vectors comprise a fusion partner, in addition to the second nucleic acid encoding a detectable protein. The fusion partner may be fused or linked to the first or second nucleic acid, or both.

In some embodiments, the second nucleic acid is a fusion partner other than a fusion partner encoding a detectable protein.

In some especially preferred embodiments, the cDNA expression vectors provided are retroviral vectors. Accordingly, retroviral cDNA expression vectors and libraries comprising the same are provided herein. In a preferred embodiment, retroviral vectors comprising random cDNAs which are operably linked to transcriptional regulatory sequence in sense orientation are provided. In another embodiment, retroviral vectors comprising random cDNAs which are operably linked to transcriptional regulatory sequence in antisense orientation are provided. In another embodiment, libraries comprising a mixture of retroviral vectors with random cDNAs in sense orientation and antisense orientation are provided.

In a preferred embodiment, the present invention provides retroviral expression vector libraries, each comprising a plurality of retroviral expression vectors, each vector comprising a) a first nucleic acid comprising a cDNA; b) a second nucleic acid which is a fusion partner; and c) a transcriptional regulatory sequence recognized by a host cell, wherein the first and second nucleic acids form a fusion nucleic acid which is operably linked to the transcriptional regulatory region. In some embodiments, the vectors also comprise a translational regulatory region which forms part of the fusion nucleic acid and initiates translation of the fusion nucleic acid.

In a preferred embodiment, the retroviral cDNA expression vectors provided herein comprise a self-inactivating 3' long terminal repeat (LTR) region which is located 3' of the first and second nucleic acids. These vectors are sometimes referred to as SIN vectors.

In a preferred embodiment, the retroviral cDNA expression vectors provided herein comprise a tetracycline-inducible (tet-inducible) promoter with an orientation opposite to the LTR and are SIN vectors. Preferred tet-inducible promoters comprise multiple copies of the tet operon operably linked to a minimal human cytomegalovirus (CMV) promoter (for example, see Gossen et al., PNAS 89:5547–5551, 1992).

In one aspect of the present invention, methods for producing random cDNA expression vectors, and libraries comprising the same, are provided. The methods involve the directional cloning of random cDNAs into expression vectors using particular adaptors and cloning sites, described below. In a preferred embodiment, the expression vectors are retroviral expression vectors. Accordingly, in a preferred embodiment, methods for producing retroviral random cDNA expression vectors, and libraries comprising the same, are provided.

In one aspect of the present invention, methods of screening for a bioactive agent capable of altering the phenotype of a cell in a desirable way are provided. In a preferred embodiment, the methods comprise the steps of a) introducing a cDNA expression vector library into a plurality of cells; b) screening the plurality of cells for a cell exhibiting a phenotype which is altered in a desirable way, wherein the altered phenotype is due to the expression of a cDNA. The methods may also comprise any of the steps of c) isolating at least one cell exhibiting an altered phenotype; d) isolating a nucleic acid comprising the cDNA from the cell exhibiting an altered phenotype; e) identifying the bioactive agent; and f) identifying and/or isolating the molecule(s) to which the agent binds. Additionally, in some preferred embodiments, the methods involve stimulating the plurality of cells in manner known to produce a disease-like response or a phenotype of the disease process. In an especially preferred embodiment, retroviral cDNA libraries provided herein are used.

In another preferred embodiment of this aspect of the invention, the methods comprise the steps of a) introducing a cDNA expression vector library into a first plurality of cells; b) contacting the first plurality of cells with a second plurality of cells; and c) screening the second plurality of cells for a cell exhibiting a phenotype which is altered in a desirable way, wherein the altered phenotype is due to contact with the first plurality of cells and expression of cDNA in the first plurality of cells. The method may also comprise any of the steps of d) isolating a cell from the first plurality of cells which is contacted with at least one cell in the second plurality of cells exhibiting an altered phenotype; e) isolating a nucleic acid comprising the cDNA from the cell isolated from the first plurality of cells; f) identifying the bioactive agent; and g) identifying and/or isolating the molecule(s) to which the agent binds. In an especially preferred embodiment, retroviral cDNA libraries provided herein are used.

In preferred embodiments of this aspect of the invention, methods of screening for bioactive agents capable of modulating the following physiological processes or biochemical activities are provided: IgE production in B cells; mast cell activation by IgE binding; mast cell degranulation; B cell activation and antibody secretion in response to antigen receptor stimulation; T cell activation in response to antigen receptor stimulation; epithelial cell activation; E3 ubiquitin ligase activity; inflammation induced by E3 ubiquitin ligase activity; inflammation induced by TNF activity; apoptosis in activated T cells; angiogenesis; uncontrolled cell proliferation; uncontrolled cell proliferation mediated by E3 ubiquitin ligase activity; and translation of Hepatitis C-encoded proteins.

Bioactive agents interact with target molecules to modulate cell phenotype. Provided herein are methods for isolating and identifying a target molecule using either the cDNA insert of a cDNA expression vector or an expression product thereof, including nucleic acids and polypeptides. Target molecules may be used to characterize signaling pathways, provide lead compounds for pharmaceutical development, and to screen for bioactive agents, including small molecule chemical compounds, capable of modulating target molecule activity.

BRIEF DESCRIPTION OF THE DRAWINGS

FIG. 1 (SEQ ID NOS: 1–9) is a schematic diagram showing the preferred scheme for modifying random cDNA with adaptors, and for directionally cloning adaptor-modified cDNA into an expression vector. The sequence of preferred SfiI adaptors for use in the present invention is given. Additionally, the figure shows preferred vector cloning site sequences, comprising SfiI recognition sequence, for directionally cloning adaptor-modified cDNAs following digestion with SfiI.

FIG. 2 (SEQ ID NOS: 10–12) is a schematic diagram showing the vector P·96.7·C2sf, a preferred vector for directionally cloning random cDNA modified with preferred adaptors comprising the SfiI site. The vector comprises the composite CRU5 promoter, which is located upstream of the SfiI-a and SfiI-b cloning sites.

FIG. 3 (SEQ ID NOS:7, 13–16) is a schematic diagram showing the recognition sequences and cleavage patterns of restriction endonucleases SfiI, BstAP1, PfiM1, Mwo1 and AlwN1.

FIG. 4 shows cDNA inserts present in 12 samplings from a directionally cloned random cDNA library generated from Jurkat T cell RNA (method described in Example 1).

FIG. 5 depicts a schematic diagram of a preferred vector.

DETAILED DESCRIPTION OF THE INVENTION

The present invention provides methods and compositions for producing directional random cDNA libraries. Directional random cDNA libraries comprising pluralities of directional random cDNA expression vectors, and methods of using these libraries, are also provided.

As used herein, the term "cDNA" means DNA that corresponds to or is complementary to at least a portion of messenger RNA (mRNA) sequence and is generally synthesized from an mRNA preparation using reverse transcriptase or other methods. cDNA as used herein includes full length cDNA, corresponding to or complementary in sequence to full length mRNA sequences, partial cDNA, corresponding to or complementary in sequence to portions of mRNA sequences, and cDNA fragments, also corresponding to or complementary to portions of mRNA sequences. It should be understood that references to a particular "number" of cDNAs or other nucleic acids actually refers to the number of clones, cDNA sequences or species, rather than the number of physical copies of substantially identical sequences present. Moreover, the term is often used to refer to cDNA sequences incorporated into a plasmid or viral vector which can, in turn, be present in a bacterial cell, mammalian packaging cell line, or host cell.

By "cDNA fragment" is meant a portion of a cDNA that is derived by fragmentation of a larger cDNA. cDNA fragments may be derived from partial or full length cDNAs. As will be appreciated, a number of methods may be used to generate cDNA fragments. For example, cDNA may be subjected to shearing forces in solution that can break the covalent bonds of the backbone of the cDNA. In a preferred embodiment, cDNA fragments are generated by digesting cDNA with restriction endonuclease(s). Other methods are well known in the art.

"Partial cDNA" refers to cDNA that comprises part of the nucleic acid sequence which corresponds to or is complementary to the open reading frame (ORF) of the corresponding mRNA.

"Full length cDNA" refers to cDNA that comprises the complete sequence which is complementary to or corresponds to the ORF of the corresponding mRNA. In some instances, which are clear, full length cDNA refers to cDNA that comprises sequence complementary to or corresponding to the 5' untranslated region (UTR) of the corresponding mRNA, in addition to sequence which is complementary to or corresponds to the complete ORF.

A corresponding mRNA comprises the nucleotide sequence of the mRNA used as template for synthesis of a particular cDNA, or is the template mRNA used for synthesis of a particular cDNA.

The occurrence of alternatively spliced mRNAs in an mRNA pool used to make cDNA may lead to the synthesis of a cDNA which has sequence corresponding to more than one mRNA type. In addition, the cDNA may comprise a nucleotide sequence that is identical to only a segment of an alternatively spliced mRNA.

By "libraries" is meant a plurality. In a preferred embodiment, the cDNA expression vector libraries provided herein comprise between about $10^3$ and about $10^9$ independent clones, with from about $10^5$ to about $10^8$ being preferred, and about $10^5$ to about $10^6$ being especially preferred.

In one aspect, provided herein are methods for producing cDNA expression vector libraries. In a preferred embodiment, methods for producing retroviral cDNA expression vector libraries are provided. The methods involve the directional cloning of random cDNA into expression vectors, using adaptors and vector cloning sites described herein. Directional cloning of random cDNA refers to the insertion of a random cDNA into a vector in a single determined orientation, which is facilitated by the non-equivalent nature of adaptor-modified cDNA ends and complementary vector cloning site sequences. In contrast, bi-directional, or non-directional cloning, involves the insertion of cDNA in either of the two possible orientations, whereby half of the cDNA is inserted in sense orientation and half of the cDNA is inserted in antisense orientation. Non-directional cloning can be achieved through the use of identical adaptor-modified cDNA ends and complementary vector cloning site sequences.

General methods for producing cDNA libraries are known in the art (Blumberg et al. Science 253:194–196 (1991); Cho et al. Cell 67:1111–1120 (1991); Hawley et al. Genes Dev. 9:2923–2935 (1995)).

Methods for constructing cDNA libraries from mRNA isolated from a cellular source are well known in the art. General protocols are, for example, disclosed in *Current Protocols in Molecular Biology*, John Wiley & Sons, Ausubel et. al. eds., 1988, updated October 2001, Chapter 5, *Construction of Recombinant DNA Libraries*, particularly Section III, *Preparation of Insert DNA from Messenger RNA*, expressly incorporated herein by reference. Additionally, two commonly used methods of producing cDNA from mRNA are described in Okayama and Berg, Mol. Cell Biol. 2, 161–170 (1982) and Gubler and Hoffman, Gene 25 263–269, (1983).

In a typical procedure, poly(A)+ mRNAs are isolated from cells. However, isolated RNA that is not poly(A)+ enriched may also be used.

Methods for isolating RNA from eukaryotic and prokaryotic cells are well known in the art. For example, see *Current Protocols in Molecular Biology*, John Wiley & Sons, Ausubel et. al. eds., 1988, updated October 2001, Chapter 4, *Preparation of RNA from Eukaryotic and Prokaryotic Cells*, expressly incorporated herein by reference; *Molecular Cloning: A Laboratory Manual*, $3^{rd}$ Edition, Sambrook et al. eds., Cold Spring Harbor Press, Cold Spring Harbor, N.Y., 2001, ISBN 0-87969-577-3. Poly(A)+, which is greatly enriched in mRNA can be separated from the remainder of total RNA, which is largely ribosomal RNA (rRNA) and transfer RNA (tRNA), for example, by binding to oligo(dT) cellulose (e.g., latex beads) while the remainder washes through. The poly(A)+ mRNA can be eluted from the beads following known procedures, such as the protocol described in Ausubel et al., supra, Unit 4.5. Some other protocols use poly(U)Sephadex instead of oligo(dT). See, e.g. Moore and Sharp, Cell 36, 581–591 (1984). A preferred method is that of Chomczynski and Sacchi, Anal. Biochem. 162:156–159 (1987). The RNA can be from any organism.

The initial mRNA may be present in a variety of different samples, where the sample will typically be derived from a physiological source. The physiological source may be derived from a variety of eukaryotic and prokaryotic sources. In addition, viral RNA may be used to serve as template for cDNA synthesis. Physiological sources of interest include sources derived from single celled organisms such as yeast and multicellular organisms, including plants and animals, particularly mammals, preferably humans, primates and rodents, where the physiological sources from multicellular organisms may be derived from particular organs or tissues of the multicellular organism, or from isolated cells derived therefrom. In obtaining the sample of RNAs from the physiological source from which it is derived, the physiological source may be subjected to a number of different processing steps, where such processing steps might include tissue homogenization, cell isolation and cytoplasmic extraction, nucleic acid extraction and the like, where such processing steps are known to those of skill in the art. Eukaryotic and prokaryotic sources include, but are not limited to, bacteria, plant, fungi, insect and mammalian sources, which include, but are not limited to algae, *Arabidopsis thaliana, Aspergillus*, Axolotl, baboon, bovine, barley, canine, carp, chicken, corn, *Drosophila melanogaster*, feline, firefly, frog, Fugu fish, hamster, human, lobster, monkey, mouse, nematode, opposum, pea, porcine, rabbit, rat, rice, sea urchin, sheep, soybean, spinach, tobacco, tomato, wheat, *Xenopus laevis*, yeast, and zebrafish. Preferred sources of RNA for use in the present invention are human, rodent, and primate. Tissue and cell sources for RNA include, but are not limited to, adipose, adrenal, adult brain, adult liver, adult ovary, amygdala, aorta, B-cell, T-cell, mast cell, bladder, blood, bone marrow, brain tumor, breast, breast tumor, capillary endothelial cells, carcinoma, cerebellum, cervix, chondrocyte, colon, colon tumor, colorectal adenocarcinoma, embryo, embryonic brain, embryonic adrenal, embryonic eye, embryonic gut, embryonic liver, embryonic lung, embryonic muscle, embryonic spleen, endothelial, epidermis, epithelial cell, erythroleukemia, esophageal tumor, esophagus, eye, fetus, fetal brain, fetal adrenal, fetal eye, fetal gut, fetal liver, fetal lung, fetal muscle, fetal spleen, fibroblast, fibrosarcoma, glioblastoma, glioma, heart, adult heart, HeLa, hepatocarcinoma, hepatoma, hippocampus, hypothalamus, intestine, small intestine, keratinocyte, kidney, kidney tumor, liver, liver tumor, lung, lung tumor, lymph node, lymphocyte, lymphoblast, lymphoma, macrophage, microglia, mammary gland, mucus-producing gland, muscle, myoblast, monocyte, nasal mucosa, neuronal, NIH 3T3, stomach, thyroid, uterus, oocyte, pancreas, ovarian tumor, pituitary, prostate, rectal tumor, rectum, retina, salivary gland, spinal cord, spleen, submucosa, stem cell, and tonsil. Viral nucleic acids may also be used.

Once isolated, mRNAs are then used as template for the synthesis of double stranded cDNA (dscDNA) using the enzyme reverse transcriptase. Synthesis of cDNA may be done in vitro or in vivo, as is known (for example, see U.S. Pat. No. 5,891,637, issued 6 Apr. 1999 to Ruppert et. al, incorporated herein be reference).

Reverse transcriptases have been traditionally purified from retroviruses, such as avian myoblastosis virus (AMV) and Moloney murine leukemia virus (M-MuLV), which use them to make DNA copies of their own RNA genomes. The M-MuLV reverse transcriptase has also been purified from overproducing *E. coli* cells containing the cloned gene. Tanese et al. in PNAS USA 82, 4944–4948 (1985) and Roth et al. in J. Biol. Chem. 260(16), 9326–9335 (1985) report on the expression, isolation and characterization of a reverse transcriptase isolated from Moloney murine leukemia virus (M-MuLV). This reverse transcriptase is encoded by the viral pol gene and is a monomer having a molecular weight of about 80 kD. See also U.S. Pat. No. 4,943,531.

In the process of converting mRNA into double stranded cDNA in vitro, a first cDNA strand is synthesized by the reverse transcriptase. A DNA polymerase, such as *E. coli* DNA polymerase, then uses the first cDNA strand as a template for the synthesis of the second cDNA strand, thereby producing a population of dscDNA molecules from the original poly(A)+ mRNA. The dscDNA is ligated to adaptors, and adaptor-modified cDNA is subsequently directionally cloned into expression vectors.

First strand cDNA synthesis is performed using any convenient protocol. In preparing the first strand cDNA, a primer is contacted with the mRNA, a reverse transcriptase, and other reagents necessary for primer extension under conditions sufficient for first strand cDNA synthesis to occur. In a preferred embodiment, the primers used for cDNA synthesis comprise a random polynucleotide from about 6 to about 12, more preferably from about 6 to about 10, more preferably from about 6 to about 9, most preferably about 8 nucleotides in length, and further comprise a 5' terminal nucleotide comprising the base cytosine, and a nucleotide immediately 3' to the 5' terminal nucleotide, comprising the base cytosine. Preferred primers may be generally described by the nucleic acid sequence 5'-CCN$_x$-3', wherein N is any nucleotide, preferably a nucleotide selected from the group consisting of dAMP, dTMP, dGMP, dCMP, or analogs thereof which are known in the art, and where x indicates a number of N nucleotides from about 4 to about 10, more preferably about 4 to about 8, with about 6 being most preferred. Thus, an especially preferred primer has the general sequence 5'-CCNNNNNN-3'.

These primers are sometimes referred to herein as random primers, with the "CC" portion being considered an overhang to the random primer.

By "random primers" is meant random sequence oligonucleotide primers, in which each of the nucleotide positions is occupied by a nucleotide selected at random from among a complete set of possibilities, but commonly limited to the four nucleotides, dAMP, dCMP, dGMP, or dTMP.

The use of primers in cDNA synthesis is well known in the art, see for example, Sambrook et al., supra.

Additional reagents that may be present include: dNTPs; buffering agents, e.g. TrisCl; cationic sources, both monovalent and divalent, e.g. KCl, MgCl$_2$; sulfhydril reagents, e.g. dithiothreitol; and the like. A variety of enzymes, usually DNA polymerases, possessing reverse transcriptase activity can be used for the first strand cDNA synthesis step. Examples of suitable DNA polymerases are described above. Preferably, the DNA polymerase will be selected from the group consisting of Moloney murine leukemia virus (M-MLV) as described in U.S. Pat. No. 4,943,531 and M-MLV reverse transcriptase lacking RNaseH activity as described in U.S. Pat. No. 5,405,776 (the disclosures of which patents are herein incorporated by reference), human T-cell leukemia virus type I (HTLV-I), bovine leukemia virus (BLV), Rous sarcoma virus (RSV), human immunodeficiency virus (HIV) and *Thermus aquatcus* (Taq) or *Thermus thermophilus* (Tth) as described in U.S. Pat. No. 5,322,770, the disclosure of which is herein incorporated by reference, avian reverse transcriptase, and the like. Suitable DNA polymerases possessing reverse transcriptase activity may be isolated from an organism, obtained commercially, or obtained from cells which express high levels of cloned genes encoding the polymerases by methods known to those of skill in the art, where the particular manner of obtaining the polymerase will be chosen based primarily on factors such as convenience, cost, availability and the like. Of particular interest because of their commercial availability and well characterized properties are avian reverse transcriptase and M-MLV.

The order in which the reagents are combined may be modified as desired. One protocol that may be used is as follows.

Primers are mixed with the total RNA or poly(A)+ RNA and processed under suitable conditions to promote first strand cDNA synthesis. Initially, the mixture of primers and RNA is, for a sufficient time, brought to a temperature sufficiently high to denature double-stranded portions of the nucleic acids. A denaturing step at 70° C. for 10 minutes is generally suitable. While reaction components are added, the mixture is kept chilled to prevent renaturation or priming. Reaction components are added to bring the mixture to a suitable buffered pH and ionic strength, to allow RNA-dependent DNA synthesis to proceed. Also added to the reaction are deoxynucleotide triphosphates for incorporation into the first cDNA strand and an RNA-dependent DNA polymerase as described above. A preferred reverse transcriptase is the Moloney murine leukemia virus reverse transcriptase.

When the first strand synthesis reaction components have been added, the mixture is incubated for a sufficient time and at a temperature appropriate for RNA-dependent DNA polymerization. Incubation at 37° C. for 60 minutes is generally suitable. When first strand synthesis is complete, the reaction is heated to a sufficiently high temperature for an adequate length of time to inactivate the RNA-dependent DNA polymerase (e.g., 70° C. for 10 minutes).

In a preferred method, following first strand cDNA synthesis, the resultant duplex mRNA/cDNA (e.g., hybrid) is contacted with an RNAse capable of degrading single stranded RNA but not RNA complexed to DNA under conditions sufficient for any single stranded RNA to be degraded. A variety of different RNAses may be employed, where known suitable RNAses include: RNAse Ti from *Aspergillus orzyae*, RNase I, RNase A and the like. The exact conditions and duration of incubation during this step will vary depending on the specific nuclease employed. However, the temperature is generally between about 20 to 37° C., and usually between about 25 to 37° C. Incubation usually lasts for a period of time ranging from about 10 to 60 min, usually from about 15 to 60 min.

Nuclease treatment results in the production of blunt-ended mRNA/cDNA duplexes or hybrids. In the resultant mixture, those mRNA/cDNA hybrids that include a full length cDNA will have the 5' cap structure of the template mRNA.

Second strand cDNA synthesis can proceed in the same reaction vessel as the first strand synthesis reaction. The reaction mixture is adjusted to buffering conditions appropriate for DNA polymerization using a DNA-dependent DNA polymerase. Also added to the second strand synthesis reaction are nucleotides for incorporation into a nascent second strand. Finally, an agent for introducing nicks into the RNA strand is added to the second strand reaction. By introducing nicks into the RNA strand, the DNA-dependent DNA polymerase can utilize the nicked RNA strands as primers for second strand DNA synthesis. During second strand synthesis, remaining RNA residues are displaced from the first strand by the growing second strand. A suitable nicking agent is RNase H (Okayama, H. and Berg, P. (1982) Mol. Cell. Biol. 2, 161; Gubler, U. and Hoffman, B. (1983) Gene 25, 263). When the reaction components have been added, the second strand synthesis reaction is allowed to proceed for a suitable length of time at a temperature adequate to support DNA-dependent DNA polymerization. A generally suitable incubation condition is 15° C. for 90 minutes. When second strand synthesis is complete, the double-stranded cDNA molecules thus formed are purified from the reaction components. Proteins can be inactivated and removed from the mixture by phenol:chloroform:isoamyl alcohol extraction. The double stranded cDNA is then precipitated with alcohol, centrifuged, and resuspended in water.

Alternatively, the first cDNA strand may be separated from mRNA using methods known in the art, and oligonucleotide primers may be used to prime synthesis of the second cDNA strand.

Secondary structure in mRNA, which can decrease the efficiency of the synthesis of cDNA, can be reduced with the use of methylmercury hydroxide to destroy base pairing as is known in the art. However, cDNA yields are reduced with the use thereof (see Krug and Berger, Methods Enzymol., 152:313–325, 1987, incorporated herein by reference.

As is known in the art, by altering the ratio of primers to mRNA in the synthesis of cDNA, the average cDNA size is modified. Decreasing the ratio of primer to mRNA increases the average cDNA length, while increasing the ratio of primer to mRNA decreases the average cDNA length. For some applications, shorter cDNA length may be desirable, for example, screening for functional domains of proteins, or screening for protein fragments with dominant negative activity. Additionally, shorter cDNA may be desired when cDNA is fused to a fusion partner that better accommodates smaller cDNA as opposed to longer cDNA, as described below. For other applications, longer cDNA sequences may be desired.

cDNAs greater than about 0.5 kb in length, preferably from between about 0.5 kb and about 5.0 kb in length, and comprising native translation start sites are particularly preferred for use in the present methods of producing expression vectors.

By native translation start site is meant the translation start site sequence found in the corresponding mRNA.

Following second strand synthesis, 3' single stranded protrusions or overhangs commonly remain on the cDNA due to dissociation of short primers near the termini. Therefore, it is desirable to remove any overhanging bases in the cDNA molecules thus formed. An appropriate enzyme for "trimming" 3' extensions and/or adding terminal nucleotides to fill in 5' overhang ends is T4 DNA polymerase.

Conditions for using T4 DNA polymerase to make double stranded DNA blunt ended are well known, for example, see Sambrook et al., supra.

It will be appreciated that the preferred primers used for cDNA synthesis in the present methods provide for the synthesis of a double stranded cDNA wherein the sense strand comprises a 3' terminus GG. As is known in the art, by convention, mRNA is a sense strand.

Alternatively, in one embodiment, following second strand synthesis, dscDNA is cleaved with selected restriction endonucleases to generate restriction fragments. These restriction fragments are then blunted with T4 DNA polymerase and used in place of uncut dscDNA. In this way, cDNA fragments are produced. Fragments useful in the present invention are those comprising the 3' terminus sequence GG or the 5' terminus sequence CC, but not both. That is, restriction enzyme digestion and blunting produces a dscDNA product having the 3' terminus sequence GG, or the 5' terminus sequence CC. Any restriction endonuclease that satisfies these requirements may be used. Preferred enzymes are those which do not cut DNA frequently (i.e., those with longer recognition sequences). Many such restriction endonucleases are known, see Sambrook et al., supra. When restriction endonuclease digestion is used to generate one of these termini, it will be appreciated that random primers or poly dT primers, rather than the preferred primers described above which comprise a 5' terminus CC, may be used in the cDNA synthesis step.

Particularly preferred are those fragments additionally comprising a translational start site.

The next step in the method is to ligate the cDNA molecule to a pair of adaptors, generating adaptor modified cDNA.

cDNA synthesis by prior art methods typically involves methylation of cDNA in order to avoid digestion in subsequent steps, for example, during cleavage of adaptors. dCTP can be replaced in the reaction mix with 5-methyl dCTP. Incorporation of 5-methyl dCTP into the growing first strand

```
5'-p-C C G C C T C G G C C A G T G G C C G T A A-3'    (SEQ ID NO:1)
   3'-G C G G A G C C G G T C A C C G G C-p-5';
``` protects the synthetic DNA from cleavage by restriction endonucleases. dCTP can, if desired, be replaced with 5-methyl dCTP during synthesis of the second cDNA strand as well so that the second strand will also be methylated, and thereby protected from cleavage by restriction endonucleases. Hemi-methylated and fully-methylated DNA are protected from cleavage by most restriction endonucleases. Another acceptable method for protecting against digestion at internal sequences is to treat the cDNA fragments with a specific DNA methylase prior to adaptor ligation.

However, an advantage of the present invention is that cDNA need not be methylated during or after synthesis to protect from digestion, as the adaptors provided for directional cloning of random cDNAs are cut with an infrequently cutting restriction enzyme, particularly SfiI. While SfiI will cut adaptors linked to cDNAs (at one end), as described below, it will not cut cDNAs internally at a high frequency, thus obviating the need to protect cDNA with methylation.

The present methods have an additional advantage over prior art methods for directionally cloning cDNA. In a preferred embodiment, cDNA synthesis is done using the preferred primer 5'-CCN$_6$-3'. Other directional cloning strategies typically use primers having long overhangs (12–20 nucleotides). These long overhangs are used to introduce restriction sites which provide for directional cloning of cDNA, but the primers are difficult to use and do not anneal to mRNA as stably as primers having short overhangs.

The primers used in the present methods comprise two nucleotides of the SfiI recognition sequence, which recognition sequence is generated in full at one cDNA end when cDNA produced with these primers is ligated to the present adaptors, as discussed below. Thus, primers with long primer overhangs comprising full restriction sites are not used in the present methods.

Adaptors are ligated to cDNA using T4 DNA ligase. The same adaptors are ligated to the 5' and 3' end of the cDNA. Preferred adaptors are generally described by the following sequence:

```
5'-p-C C N₁ N₂ N₃ N₄ N₅ G G C C Nₓ G G C C N₆ N₇ N₈ N₉-3'    (SEQ ID NO:17)
   3'-G G N'₁N'₂N'₃N'₄N'₅C C G G N'ₓC C G G N'₆-p-5';
``` wherein N$_1$ through N$_9$ are each any nucleotide, preferably a nucleotide selected from the group consisting of dAMP, dTMP, dGMP, dCMP, or analogs thereof which are known in the art, and where N$_x$ indicates a number of nucleotides, which may be any nucleotide, from about 1 to about 9 nucleotides, with 3 being most preferred, and wherein N' denotes a nucleotide which is complementary to N.

In addition, the preferred adaptors are designed such that unwanted blunt end ligated adaptor dimers are also cut with SfiI.

In an especially preferred embodiment, the adaptors have the following sequence:

Excess adaptors and small cDNAs may be removed in a gel filtration step. Preferred cDNAs are from about 0.5 kb to about 5.0 kb in size.

Adaptor modified cDNA is inserted between 5' and 3' sites in an expression vector. The vector sites when cut provide distinct 3' overhangs which are complementary to the 3' overhangs of adaptor-modified cDNA which has been cut with SfiI, providing for the directional cloning of cDNA.

The preferred vector sites are as follows:
a) a 5' SfiI-a site comprising the sequence 5'-GGCCNN'$_9$ N'$_8$ N'$_7$ NGGCC-3' (SEQ ID NO:7), and an SfiI-b site located 3' of this SfiI-a site, comprising the sequence 5'-GGCCNN$_2$ N$_3$ N$_4$ NGGCC-3' (SEQ ID NO:7) as read on the same strand; or
b) a 5' SfiI-b site comprising the sequence 5'-GGCCNN'$_4$ N'$_3$ N'$_2$ NGGCC-3' (SEQ ID NO:7) and an SfiI-a site located 3' of this SfiI-b site, comprising the sequence 5'-GGCCNN$_7$ N$_8$ N$_9$ NGGCC-3' (SEQ ID NO:7) as read on the same strand;

wherein N$_2$ N$_3$ N$_4$ and N$_7$ N$_8$ N$_9$ are the same nucleotides denoted for adaptors, wherein N is any nucleotide, preferably a nucleotide selected from the group consisting of dAMP, dTMP, dGMP, dCMP, or analogs thereof which are known in the art, and wherein N' denotes a nucleotide which is complementary to N.

Especially preferred vector sites for use with the especially preferred adaptors described above are as follows:
a) the 5' SfiI-a site 5'-GGCCATTACGGCC-3' SEQ ID NO:8 and the 3' SfiI-b site 5'-GGCCGCCTCGGCC-3' (SEQ ID NO:9);
b) the 5' SfiI-b site GGCCGAGGCGGCC (SEQ ID NO:18) and the 3' SfiI-a site GGCCGTAATGGCC (SEQ ID NO:19).

These sites comprise the SfiI recognition sequence, and the vector is engineered such that these are the only SfiI sites present in the expression vector.

By cleaving adaptor-modified cDNA with SfiI, distinct, non-complementary ends are produced. By cleaving vector with SfiI, the same distinct, non-complementary ends are produced. The cleaved adaptor-modified cDNA can then be directionally cloned into the expression vector. Further, when cDNA-modified with preferred adaptors is cloned into these preferred vector sites, SfiI sites remain flanking the cDNA insert, and SfiI may be used to excise the cDNA from the expression vector.

Additional adaptors may also be used, but are less preferred because they do not generate SfiI recognition sites at both ends following insertion into an expression vector comprising SfiI-a and SfiI-b sites.

These adaptors are generally described by the following sequence:

```
5'-p-C C N1 N2 N3 N4 N5 G G C C Nx N6 N7 N8 -3'        (SEQ ID NO:20)

3'-G G N'1N'2N'3N'4N'5C C G G Nx'-p-5';
```

In one embodiment, cDNA used in the methods is a cDNA restriction fragment having a 3' terminus GG, or a 5' terminus CC, but not both, as described above. As will be appreciated, those cDNA fragments which have both a 3' terminus GG and a 5' terminus CC (3' antisense GG) will not be directionally cloned, as both ends of the adaptor-modified cDNA will be cut with SfiI, generating identical 3' overhangs.

Especially preferred cDNA fragments are those fragments cut once with restriction endonuclease and comprising a native translation start site.

Additional vector sites may be used, but are less preferred because insertion of adaptor-modified cDNA at these sites does not generate an SfiI site, which is desirable for excision. In addition, SfiI is an infrequently cutting restriction endonuclease, which is desirable. The use of restriction endonucleases which cut DNA with a higher frequency than SfiI increases the chance of cutting cDNA internally with excision from the expression vector. However, flanking sites may be engineered into a vector, and cDNA may be removed using these flanking sites, which may be SfiI sites. Additionally, cDNA may be obtained by means other than excision, for example, by PCR.

Accordingly, a vector can comprise cloning sites other than SfiI-a and SfiI-b sites, and still provide for directional cloning of cDNA that is adaptor modified as described herein. Useful vector sites are those that when cut with the corresponding restriction enzymes generate distinct 3' overhangs which are complementary to those of the adaptor-modified cDNA. Useful sites include, but are not limited to, the recognition sequences for BstAP1, PfiM1, Mwo1 and AlwN1. When these sequences are cut with corresponding restriction enzymes, 3' overhangs 3 nucleotides in length are generated. The sequence of the overhangs is determined by the sequence of the recognition site. The consensus recognition sequences of the enzymes listed above are similar to that of SfiI, in that the core region of the sequence, which comprises the overhang sequence generated following digestion, may comprise any nucleotide sequence. For example, the MwoI recognition sequence is as follows:

5'-GCNNNNNNNGC-3' (SEQ ID NO:15),
3'-CGNNNNNNNCG-5' (SEQ ID NO:15)

where N is any nucleotide.

When cut with MwoI, the following 3' overhang is generated:

```
5'-GCNNNNN-3'

3'-CGNN-5'.
```

Accordingly, an MwoI site can be engineered in the vector to provide a specific 3' overhang sequence, which by design will be complementary to one of the adaptor modified cDNA ends.

wherein $N_1$ through $N_8$ are each any nucleotide, preferably a nucleotide selected from the group consisting of dAMP, dTMP, dGMP, dCMP, or analogs thereof which are known in the art, and where $N_x$ indicates a number of nucleotides, which may be any nucleotide, from about 4 to about 14 nucleotides, more preferably about 6 to about 14, more preferably about 8 to about 14, and wherein N' denotes a nucleotide which is complementary to N.

When adaptors are ligated to cDNA as described above, an SfiI recognition site is generated at one end of the molecule. Once cut with SfiI, the adaptor-modified cDNA has distinct non-complementary 3' overhangs; one being $N_2N_3N_4$, the other being $N_6N_7N_8$. The adaptor-modified cDNA can be directionally cloned into an appropriate vector, which may comprise the preferred SfiI-a/b sites, or other sites capable of generating distinct overhangs complementary to those of the cDNA.

The requirement of at least four nucleotides ($N_x$) following the 3' end of the SfiI recognition sequence (as formed at one end of the cDNA following ligation thereto) is to ensure cleavage of the sequence by SfiI, which requires some sequence following the end of the recognition sequence for effective cleavage.

Enriching for full-length cDNAs is useful in the present invention. Clones having cDNAs that comprise the 5' UTR and which are operably linked to transcription control sequences in the vector allow initiation from proper transcription initiation sites. In addition, full length cDNAs comprise native translation start sites, providing for translation of a native ORF. Further, full length cDNAs provide 5' sequence which often encodes important N-terminal functional moieties, including targeting signals.

Enriching for full length cDNAs can be done by the oligo-capping method (Manuyama and Sugano, Gene 138: 171–174 (1994)). This method has been used to obtain libraries with more than 80% full-length clones (Suzuki et al., Gene 200:149–156 (1997)). Regarding the capping method, see also Kato et al. Gene 25, 243–250 (1994). Kits for performing the oligo-capping method are commercially available and may be used in the present methods. For example, see Ambion, FirstChoice™ RLM-RACE kit, catalog #1700, Ambion Inc., Austin, Tex., USA.

The capping method is briefly described as follows. A combination of enzymes may be used to select full length poly(A)+ mRNAs and tag their ultimate 5' ends. Starting from a population of poly(A)+ mRNAs including sequences that are not full length, a phosphatase (such as HK thermolabile phosphatase) can be used to remove the phosphate moiety from mRNAs that are not full length, leaving 5'-OH ends at those mRNAs. Full length poly(A)+ mRNAs are protected due to the 7-methyl-Gppp cap. Tobacco Acid Pyrophosphatase is then used to digest the 7-methyl-Gppp cap, leaving a 5' phosphate moiety at the 5' end of the full length mRNA. T4 RNA ligase is then used to tag the full length poly(A)+ mRNAs at their 5' ends with "oligo-caps".

The oligo caps have a 3'-OH end and thus can be ligated only to poly(A)+ mRNAs displaying a 5' phosphate moiety. Thus, at the end of this procedure, the full-length mRNAs are tagged at the 5' end by an oligonucleotide and naturally at the 3' end by poly(A). Conveniently, the oligonucleotide cap is an RNA oligonucleotide, made by in vitro transcription or made by using an oligonucleotide synthesizer, or a hybrid RNA/DNA oligonucleotide made in an oligonucleotide synthesizer. The oligonucleotide cap can be engineered to include other sequences, including linker sequences for linking first and second nucleic acids, as described herein.

In a preferred embodiment, the oligonucleotide cap is engineered to provide a 5' terminus CC (encoding a first strand cDNA 3' terminus GG). A preferred oligonucleotide CAP comprises a 5' terminus CC. Alternatively, the CAP may comprise an internal CC sequence, and the 5' terminus CC required for the method may be generated subsequent to capping with an inner PCR reaction (for example, see Ambion, FirstChoice™ RLM-RACE kit, catalog #1700, Ambion Inc., Austin, Tex., USA).

The 5' CAP attached to the mRNA is transcribed into cDNA. An oligonucleotide comprising the CAP oligo sequence can be annealed to the cDNA CAP and used as a primer for synthesizing the second cDNA strand.

In one embodiment, cDNA synthesis biased towards the 5' end, as opposed to the 3' end bias that typically occurs with poly dT primer, is performed. Random primers are used in combination with CAP oligos and primers. This method provides for capturing important 5' encoded functional moieties, described above, without synthesizing full length cDNA.

Normalizing cDNA synthesis may also be done. Normalizing is useful because it generally increases the diversity of isolated mRNAs. Normalizing reduces the number of abundant mRNAs while increasing the frequency of rare mRNAs in a sample. For example, abundant mRNAs can be reduced between 100- to 1000-fold, while rare mRNAs can be increased up to 100-fold. Normalized libraries are well known in the art (Soares et al., Proc. Nat'l Acad. Sci. USA 91:9228–9232 (1994); Bonaldo et al., Genome Res. 6:791–806 (1996), Komiya et al., Anal. Biochem. 254: 23–30 (1997)).

Typically, normalization is carried out prior to capping and comprises the following steps:
(i) binding the poly(A)+ mRNAs to oligo d(T) coated substrate;
(ii) synthesizing cDNA strands that are complementary to the mRNAs;
(iii) denaturing the cDNA and mRNA strands;
(iv) annealing the mRNAs to the substrate bound cDNAs under conditions such that high abundant mRNAs anneal to the substrate bound cDNAs and low abundance mRNAs do not anneal; and,
(v) collecting a fraction containing the low abundance mRNAs.

These steps may be repeated until the desired level of normalization is achieved in the population of mRNAs.

Expression vectors additionally comprise control sequences, particularly transcriptional regulatory sequences, which are operably linked to cDNA. The orientation of cDNA with respect to these transcriptional regulatory sequences determines whether the cDNA is in sense or antisense configuration.

By transcriptional regulatory sequence (or transcriptional regulatory region, or transcriptional control sequence) is meant a nucleic acid sequence that can regulate transcription from a template strand of nucleic acid by a nucleic acid polymerase. Transcriptional regulatory sequences regulate the expression of an operably linked nucleic acid sequence. The preferred transcriptional regulatory sequence is an RNA polymerase promoter which is positioned relative to a cDNA in such a manner that transcription of the cDNA sequence is initiated.

By "operably linked" is meant that a nucleic acid sequence is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; and a ribosome binding site is operably linked to a coding sequence if it is positioned so as to facilitate translation. As another example, operably linked refers to DNA sequences linked so as to be contiguous, and, in the case of a secretory leader, contiguous and in reading frame. However, enhancers do not have to be contiguous. Linking is accomplished by ligation at convenient restriction sites. If such sites do not exist, the synthetic oligonucleotide adaptors or linkers are used in accordance with conventional practice. The transcriptional and translational regulatory nucleic acid will generally be appropriate to the host cell used; for example, transcriptional and translational regulatory nucleic acid sequences from *Bacillus* are preferably used to express cDNA in *Bacillus*. Numerous types of appropriate expression vectors, and suitable regulatory sequences are known in the art for a variety of host cells.

In some embodiments, expression vectors additionally comprise translation regulatory sequences.

In general, the transcriptional and translational regulatory sequences may include, but are not limited to, promoter sequences, ribosomal binding sites, transcriptional start and stop sequences, translational start and stop sequences, repressor sequences, and enhancer or activator sequences. In a preferred embodiment, the regulatory sequences include a promoter and transcriptional start and stop sequences.

Promoter sequences are either constitutive or inducible promoters. The promoters may be either naturally occurring promoters or hybrid promoters. Hybrid promoters, which combine elements of more than one promoter, are also known in the art, and are useful in the present invention.

A preferred promoter for use in the expression vectors provided herein is the composite promoter "CRU5", discussed further below.

A preferred inducible promoter for use in the expression vectors provided herein is a tet-inducible promoter, discussed further below.

Expression vectors provided herein may comprise additional elements. For example, the expression vector may have two replication systems, thus allowing it to be maintained in two organisms, for example in mammalian or insect cells for expression and in a prokaryotic host for cloning and amplification. Furthermore, for some integrating expression vectors, the expression vector contains at least one sequence homologous to the host cell genome, and preferably two homologous sequences which flank the expression construct. The integrating vector may be directed to a specific locus in the host cell by selecting the appropriate homologous sequence for inclusion in the vector. Constructs for integrating vectors are well known in the art.

Expression vectors may also include cDNA fusion partners. "Fusion partner" as used herein can refer to nucleic acids and peptides. Fusion partner can refer both to the fusion partner encoding nucleic acid sequence in an expression vector, and a nucleic acid or peptide expression product of the encoding sequence. The use of fusion partners is particularly desirable when using cDNA libraries to screen for bioactive agents that can modulate cell phenotype in a desirable way, as described below.

In a preferred embodiment, cDNAs are fused to fusion partners. In another preferred embodiment, cDNAs are linked to fusion partners by linkers, as described below. In this embodiment, cDNAs may be tethered to fusion partners, or may be separate or separable from fusion partners, as described below.

cDNA may be positioned 5', 3', or within a fusion partner, as described below. By "fusion partner" or "functional group" herein is meant a sequence that is associated with a cDNA expression product, including nucleic acids and peptides, that confers upon all members of the library in that class a common function or ability.

In the discussion of fusion partners that follows, cDNA expression products are sometimes referred to as candidate bioactive agents, candidate agents, candidate peptides, or candidate nucleic acids, stemming from their use in methods of screening for bioactive agents, described below.

Fusion partners can be heterologous (i.e. not native to the host cell), or synthetic (not native to any cell). Suitable fusion partners include, but are not limited to: a) presentation structures, as defined below, which provide the candidate bioactive agents in a conformationally restricted or stable form; b) targeting sequences, defined below, which allow the localization of the candidate bioactive agent into a subcellular or extracellular compartment; c) rescue sequences as defined below, which allow the purification or isolation of either the candidate bioactive agents or the nucleic acids encoding them; d) stability sequences, which confer stability or protection from degradation to the candidate bioactive agent or the nucleic acid encoding it, for example resistance to proteolytic degradation; e) dimerization sequences, to allow for peptide dimerization; f) label sequences; or g) any combination of a), b), c), d), e), and f), as well as linker sequences as needed.

In a preferred embodiment, the fusion partner is a presentation structure. By "presentation structure" or grammatical equivalents herein is meant a sequence, which, when fused to candidate bioactive agents, causes the candidate agents to assume a conformationally restricted form. Proteins interact with each other largely through conformationally constrained domains. Although small peptides with freely rotating amino and carboxyl termini can have potent functions as is known in the art, the conversion of such peptide structures into pharmacologic agents is difficult due to the inability to predict side-chain positions for peptidomimetic synthesis. Therefore the presentation of cDNA-encoded peptides in conformationally constrained structures will benefit both the later generation of pharmaceuticals and will also likely lead to higher affinity interactions of the peptide with the target protein. This fact has been recognized in the combinatorial library generation systems using biologically generated short peptides in bacterial phage systems. A number of workers have constructed small domain molecules in which one might present randomized peptide structures.

Synthetic presentation structures are usually peptides, i.e. artificial polypeptides, and are capable of presenting a candidate peptide as a conformationally-restricted domain. Generally such presentation structures comprise a first portion joined to the N-terminal end of the candidate peptide, and a second portion joined to the C-terminal end of the peptide; that is, the peptide is inserted into the presentation structure, although variations may be made. To increase the functional isolation of the candidate peptide, the presentation structures are selected or designed to have minimal biological activity when expressed in the target cell.

Preferred presentation structures maximize accessibility to the cDNA-encoded peptide by presenting it on an exterior loop. Accordingly, suitable presentation structures include, but are not limited to, minibody structures, loops on beta-sheet turns and coiled-coil stem structures in which residues not critical to structure are found, zinc-finger domains, cysteine-linked (disulfide) structures, transglutaminase linked structures, cyclic peptides, B-loop structures, helical barrels or bundles, leucine zipper motifs, etc.

In a preferred embodiment, the presentation structure is a coiled-coil structure, allowing the presentation of the candidate peptide on an exterior loop. See, for example, Myszka et al., Biochem. 33:2362–2373 (1994), hereby incorporated by reference). Using this system investigators have isolated peptides capable of high affinity interaction with the appropriate target.

In a preferred embodiment, the presentation structure is a minibody structure. A "minibody" is essentially composed of a minimal antibody complementarity region. The minibody presentation structure generally provides two sequence replacement regions that in the folded protein are presented along a single face of the tertiary structure. See for example Bianchi et al., J. Mol. Biol. 236(2):649–59 (1994), and references cited therein, all of which are incorporated by reference). Investigators have shown this minimal domain is stable in solution and have used phage selection systems in combinatorial libraries to select minibodies with peptide regions exhibiting high affinity, $Kd=10^{-7}$, for the pro-inflammatory cytokine IL-6.

In a preferred embodiment, the presentation structure is a sequence that contains generally two cysteine residues, such that a disulfide bond may be formed, resulting in a conformationally constrained sequence. This embodiment is particularly preferred when secretory targeting sequences are used. As will be appreciated by those in the art, any number of candidate peptides, with or without spacer sequences, may be flanked with cysteine residues.

In a preferred embodiment, the presentation structure can be a protein, such as that encoded by a reporter gene. For example, fusion of peptides to reporter proteins such as GFP have been shown to confer conformational stability.

In a preferred embodiment, the fusion partner is a targeting sequence. As will be appreciated by those in the art, the localization of proteins within a cell is a simple method for increasing effective concentration and determining function. For example, RAF1 when localized to the mitochondrial membrane can inhibit the anti-apoptotic effect of BCL-2. Similarly, membrane bound Sos induces Ras mediated signaling in T-lymphocytes. These mechanisms are thought to rely on the principle of limiting the search space for ligands, that is to say, the localization of a protein to the plasma membrane limits the search for its ligand to that limited dimensional space near the membrane as opposed to the three dimensional space of the cytoplasm. Alternatively, the concentration of a protein can also be simply increased by nature of the localization. Shuttling the proteins into the nucleus confines them to a smaller space thereby increasing concentration. Finally, the ligand or target may simply be localized to a specific compartment, and inhibitors must be localized appropriately.

Targetting sequences may serve to deliver cDNA expression products to subcellular locations in which full length transcription or translation products of the corresponding mRNA are not typically found.

Suitable targeting sequences include, but are not limited to, binding sequences capable of causing binding of the cDNA fragment expression product to a predetermined molecule or class of molecules while retaining bioactvity of the expression product, (for example by using enzyme inhibitor or substrate sequences to target a class of relevant enzymes); sequences signalling selective degradation, of itself or co-bound proteins; and signal sequences capable of constitutively localizing the candidate expression products to a predetermined cellular locale, including a) subcellular locations such as the Golgi, endoplasmic reticulum, nucleus, nucleoli, nuclear membrane, mitochondria, chloroplast, secretory vesicles, lysosome, and cellular membrane; and b) extracellular locations via a secretory signal. Particularly preferred is localization to either subcellular locations or to the outside of the cell via secretion.

In a preferred embodiment, the targeting sequence is a nuclear localization signal (NLS). NLSs are generally short, positively charged (basic) domains that serve to direct the entire protein in which they occur to the cell's nucleus. Numerous NLS amino acid sequences have been reported including single basic NLS's such as that of the SV40 (monkey virus) large T Antigen (Pro Lys Lys Lys Arg Lys Val) (SEQ ID NO:21), Kalderon (1984), et al., Cell, 39:499–509; the human retinoic acid receptor-.beta. nuclear localization signal (ARRRRP) (SEQ ID NO:22); NFκB p50 (EEVQRKRQKL (SEQ ID NO:23); Ghosh et al., Cell 62:1019 (1990); NFκB p65 (EEKRKRTYE (SEQ ID NO:24); Nolan et al., Cell 64:961 (1991); and others (see for example Boulikas, J. Cell. Biochem. 55(1):32–58 (1994), hereby incorporated by reference) and double basic NLS's exemplified by that of the *Xenopus* (African clawed toad) protein, nucleoplasmin (Ala Val Lys Arg Pro Ala Ala Thr Lys Lys Ala Gly Gln Ala Lys Lys Lys Lys Leu Asp) (SEQ ID NO:25), Dingwall, et al., Cell, 30:449–458, 1982 and Dingwall, et al., J. Cell Biol., 107:641–849; 1988). Numerous localization studies have demonstrated that NLSs incorporated in synthetic peptides or grafted onto reporter proteins not normally targeted to the cell nucleus cause these peptides and reporter proteins to be concentrated in the nucleus. See, for example, Dingwall, and Laskey, Ann, Rev. Cell Biol., 2:367–390, 1986; Bonnerot, et al., Proc. Natl. Acad. Sci. USA, 84:6795–6799, 1987; Galileo, et al., Proc. Natl. Acad. Sci. USA, 87:458–462, 1990.

In a preferred embodiment, the targeting sequence is a membrane anchoring signal sequence. This is particularly useful since many parasites and pathogens bind to the membrane, in addition to the fact that many intracellular events originate at the plasma membrane. Thus, membrane-bound cDNA-encoded peptide libraries are useful for both the identification of important elements in these processes as well as for the discovery of effective inhibitors. The invention provides methods for presenting the candidate agent extracellularly or in the cytoplasmic space. For extracellular presentation, a membrane anchoring region is provided at the carboxyl terminus of the peptide presentation structure. The candidate agent is expressed on the cell surface and presented to the extracellular space, such that it can bind to other surface molecules (affecting their function) or molecules present in the extracellular medium. The binding of such molecules could confer function on the cells expressing a peptide that binds the molecule. The cytoplasmic region could be neutral or could contain a domain that, when the extracellular candidate agent is bound, confers a function on the cells (activation of a kinase, phosphatase, binding of other cellular components to effect function). Similarly, the candidate agent could be contained within a cytoplasmic region, and the transmembrane region and extracellular region remain constant or have a defined function.

Membrane-anchoring sequences are well known in the art and are based on the genetic geometry of mammalian transmembrane molecules. Peptides are inserted into the membrane based on a signal sequence (designated herein as ssTM) and require a hydrophobic transmembrane domain (herein TM). The transmembrane proteins are inserted into the membrane such that the regions encoded 5' of the transmembrane domain are extracellular and the sequences 3' become intracellular. Of course, if these transmembrane domains are placed 5' of the candidate agent region, they will serve to anchor it as an intracellular domain, which may be desirable in some embodiments. ssTMs and TMs are known for a wide variety of membrane bound proteins, and these sequences may be used accordingly, either as pairs from a particular protein or with each component being taken from a different protein, or alternatively, the sequences may be synthetic, and derived entirely from consensus as artificial delivery domains.

As will be appreciated by those in the art, membrane-anchoring sequences, including both ssTM and TM, are known for a wide variety of proteins and any of these may be used. Particularly preferred membrane-anchoring sequences include, but are not limited to, those derived from CD8, ICAM-2, IL-BR, CD4 and LFA-1.

Useful sequences include sequences from: 1) class I integral membrane proteins such as IL-2 receptor beta-chain (residues 1–26 are the signal sequence, 241–265 are the transmembrane residues; see Hatakeyama et al., Science 244:551 (1989) and von Heijne et al, Eur. J. Biochem. 174:671 (1988)) and insulin receptor beta chain (residues 1–27 are the signal, 957–959 are the transmembrane domain and 960–1382 are the cytoplasmic domain; see Hatakeyama, supra, and Ebina et al., Cell 40:747 (1985)); 2) class II integral membrane proteins such as neutral endopeptidase (residues 29–51 are the transmembrane domain, 2–28 are the cytoplasmic domain; see Malfroy et al., Biochem. Biophys. Res. Commun. 144:59 (1987)); 3) type III proteins such as human cytochrome P450 NF25 (Hatakeyama, supra); and 4) type IV proteins such as human P-glycoprotein (Hatakeyama, supra). Particularly preferred are CD8 and ICAM-2. For example, the signal sequences from CD8 and ICAM-2 lie at the extreme 5' end of the transcript. These consist of the amino acids 1–32 in the case of CD8 (MASPLTRFLSLNLLLLGESILGSGEAKPQAP (SEQ ID NO:26); Nakauchi et al., PNAS USA 82:5126 (1985) and 1–21 in the case of ICAM-2 (MSSFGYRTLTVALFTLICCPG (SEQ ID NO:27); Staunton et al., Nature (London) 339:61 (1989)). These leader sequences deliver the construct to the membrane while the hydrophobic transmembrane domains, placed 3' of the candidate agent region, serve to anchor the construct in the membrane. These transmembrane domains are encompassed by amino acids 145–195 from CD8 (PQRPEDCRPRGSVKGTGLDFACDIYIWAPLAGICVALLLSLIITLICYHSR (SEQ ID NO:28); Nakauchi, supra) and 224–256 from ICAM-2 (MVIIVTVVSVLLSLFVTSVLLCFIFGQHLRQQR (SEQ ID NO:29); Staunton, supra).

Alternatively, membrane anchoring sequences include the GPI anchor, which results in a covalent bond between the molecule and the lipid bilayer via a glycosyl-phosphatidylinositol bond for example in DAF (PNKGSGTTSGTTRLLSGHTCFTLTGLLGTLVTMGLLT (SEQ ID NO:30), with the bolded serine the site of the anchor; see Homans et al., Nature 333(6170):269–72 (1988), and Moran et al., J. Biol. Chem. 266:1250 (1991)). In order to do this, the GPI sequence from Thy-1 can be cassetted 3' of the candidate agent region in place of a transmembrane sequence.

Similarly, myristylation sequences can serve as membrane anchoring sequences. It is known that the myristylation of c-src recruits it to the plasma membrane. This is a simple and effective method of membrane localization, given that the first 14 amino acids of the protein are solely responsible for this function: MGSSKSKPKDPSQR (SEQ ID NO:31) (see Cross et al., Mol. Cell. Biol. 4(9):1834 (1984); Spencer et al., Science 262:1019–1024 (1993), both of which are hereby incorporated by reference). This motif has already been shown to be effective in the localization of reporter genes and can be used to anchor the zeta chain of the TCR. This motif is placed 5' of the candidate agent region in order to localize the construct to the plasma membrane. Other modifications such as palmitoylation can be used to anchor constructs in the plasma membrane; for example, palmitoylation sequences from the G protein-coupled receptor kinase GRK6 sequence (LLQRLFSRQD-CCGNCSDSEEELPTRL (SEQ ID NO:32), with the bold cysteines being palmitoylated; Stoffel et al., J. Biol. Chem 269:27791 (1994)); from rhodopsin (KQFRNCM-LTSLCCGKNPLGD (SEQ ID NO:33); Barnstable et al., J. Mol. Neurosci. 5(3):207 (1994)); and the p21 H-ras 1 protein (LNPPDESGPGCMSCKCVLS (SEQ ID NO:34); Capon et al., Nature 302:33 (1983)).

In a preferred embodiment, the targeting sequence is a lysozomal targeting sequence, including, for example, a lysosomal degradation sequence such as Lamp-2 (KFERQ (SEQ ID NO:35); Dice, Ann. N.Y. Acad. Sci. 674:58 (1992); or lysosomal membrane sequences from Lamp-1 (MLIP-IAGFFALAGLVUVLIAYLIGRKRSHAGYQTI (SEQ ID NO:36), Uthayakumar et al., Cell. Mol. Biol. Res. 41:405 (1995)) or Lamp-2 (LVPIAVGAALAGVLILVLLAY-FIGLKHHHAGYEQF (SEQ ID NO:37), Konecki et la., Biochem. Biophys. Res. Comm. 205:1–5 (1994), both of which show the transmembrane domains in italics and the cytoplasmic targeting signal underlined).

Alternatively, the targeting sequence may be a mitrochondrial localization sequence, including mitochondrial matrix sequences (e.g. yeast alcohol dehydrogenase III; MLRTSS-LFTRRVQPSLFSRNILRLQST (SEQ ID NO:38); Schatz, Eur. J. Biochem. 165:1–6 (1987)); mitochondrial inner membrane sequences (yeast cytochrome c oxidase subunit IV; MLSLRQSIRFFKPATRTLCSSRYLL (SEQ ID NO:39); Schatz, supra); mitochondrial intermembrane space sequences (yeast cytochrome c1; MFSMLSKRWAQRTL-SKSFYSTATGAASKS-GKLTQKLVTAGVAAAGITASTLLYADSLTAEAMT A (SEQ ID NO:40); Schatz, supra) or mitochondrial outer membrane sequences (yeast 70 kD outer membrane protein; MKSFITRNKTAJLATVMTG-TAIGAYYYYNQLQQQQQRGKK (SEQ ID NO:41); Schatz, supra).

The target sequences may also be endoplasmic reticulum sequences, including the sequences from calreticulin (KDEL (SEQ ID NO:42); Pelham, Royal Society London Transactions B; 1–10 (1992)) or adenovirus E3/19K protein (LYLSRRSFIDEKKMP (SEQ ID NO:43); Jackson et al., EMBO J. 9:3153 (1990).

Furthermore, targeting sequences also include peroxisome sequences (for example, the peroxisome matrix sequence from Luciferase; SKL; Keller et al., PNAS USA 4:3264 (1987)); farnesylation sequences (for example, P21 H-ras 1; LNPPDESGPGCMSCKCVLS (SEQ ID NO:34), with the bold cysteine farnesylated; Capon, supra); geranylgeranylation sequences (for example, protein rab-5A; LTEPTQPTRNQCCSN (SEQ ID NO:44), with the bold cysteines geranylgeranylated; Farnsworth, PNAS USA 91:11963 (1994)); or destruction sequences (cyclin B1; RTALGDIGN (SEQ ID NO:45); Klotzbucher et al., EMBO J. 1:3053 (1996)).

In a preferred embodiment, the targeting sequence is a secretory signal sequence capable of effecting the secretion of the candidate translation product. There are a large number of known secretory signal sequences which are placed 5' to the variable peptide region, and are cleaved from the peptide region to effect secretion into the extracellular space. Secretory signal sequences and their transferability to unrelated proteins are well known, e.g., Silhavy, et al. (1985) Microbiol. Rev. 49, 398–418. This is particularly useful to generate a peptide capable of binding to the surface of, or affecting the physiology of, a target cell that is other than the host cell, e.g., the cell infected with the retrovirus. In a preferred approach, a fusion product is configured to contain, in series, secretion signal peptide-presentation structure-candidate agent-presentation structure, In this manner, target cells grown in the vicinity of cells caused to express the library of peptides, are bathed in secreted peptide. Target cells exhibiting a physiological change in response to the presence of a peptide, e.g., by the peptide binding to a surface receptor or by being internalized and binding to intracellular targets, and the secreting cells are localized by any of a variety of selection schemes and the peptide causing the effect determined. Exemplary effects include variously that of a designer cytokine (e.g., a stem cell factor capable of causing hematopoietic stem cells to divide and maintain their totipotental), a factor causing cancer cells to undergo spontaneous apoptosis, a factor that binds to the cell surface of target cells and labels them specifically, etc.

Suitable secretory sequences are known, including signals from IL-2 (MYRMQLLSCIALSLALVTNS (SEQ ID NO:46); Villinger et al., J. Immunol. 155:3946 (1995)), growth hormone (MATGSRTSLLLAFGLLCLPWLQEG-SAFPT (SEQ ID NO:47); Roskam et al., Nucleic Acids Res. 7:30 (1979)); preproinsulin (MALWMRLLPLLALLAL-WGPDPAAAFVN (SEQ ID NO:48); Bell et al., Nature 284:26 (1980)); and influenza HA protein (MKAKLLVL-LYAFVAGDQI (SEQ ID NO:49); Sekiwawa et al., PNAS 80:3563)), with cleavage between the non-underlined-underlined junction. A particularly preferred secretory signal sequence is the signal leader sequence from the secreted cytokine IL-4, which comprises the first 24 amino acids of IL-4 as follows: MGLTSQLLPPLFFLLACAGNFVHG (SEQ ID NO:50).

In a preferred embodiment, the fusion partner is a rescue sequence. A rescue sequence is a sequence which may be used to purify or isolate either the candidate agent or the nucleic acid encoding it. Thus, for example, peptide rescue sequences include purification sequences such as the $His_6$ tag for use with Ni affinity columns and epitope tags for detection, immunoprecipitation or FACS (fluoroscence-activated cell sorting). Suitable epitope tags include myc (for use with the commercially available 9E10 antibody), the BSP biotinylation target sequence of the bacterial enzyme BirA, flu tags, lacZ, and GST.

Alternatively, the rescue sequence may be a unique oligonucleotide sequence which serves as a probe target site to allow the quick and easy isolation of the cDNA, via PCR, related techniques, or hybridization. The probe target site may be incorporated into the cDNA using the oligo capping method, discussed above, in conjunction with CAP oligos comprising probe sequence.

In a preferred embodiment, the fusion partner is a stability sequence to confer stability to the candidate bioactive agent or the nucleic acid encoding it. Thus, for example, candidate peptides may be stabilized by the incorporation of glycines after the initiation methionine (MG or MGG), for protection of the peptide to ubiquitination as per Varshavsky's N-End Rule, thus conferring long half-life in the cytoplasm. Similarly, two prolines at the C-terminus provide for candidate peptides that are largely resistant to carboxypeptidase action. The presence of two glycines prior to the prolines imparts flexibility and prevents structure initiating events in the di-proline from being propagated into the candidate peptide structure. Thus, preferred stability sequences are as follows: MG(X)$_n$ GGPP (SEQ ID NO:51), where X is any amino acid and n is an integer of at least four.

In one embodiment, the fusion partner is a dimerization sequence. A dimerization sequence allows the non-covalent association of one candidate peptide to another candidate peptide, with sufficient affinity to remain associated under normal physiological conditions. This effectively allows small libraries of candidate peptides (for example, $10^4$) to become large libraries if two peptides per cell are generated which then dimerize, to form an effective library of $10^8$ ($10^4 \times 10^4$). It also allows the formation of longer candidate peptides, if needed, or more structurally complex candidate peptide molecules. The dimers may be homo- or heterodimers. See for example U.S. Ser. No. 09/285,912, incorporated herein in its entirety by reference.

Dimerization sequences may be a single sequence that self-aggregates, or two sequences, each of which is generated in a different cDNA expression vector construct. That is, nucleic acids encoding both a first candidate peptide with dimerization sequence 1, and a second candidate peptide with dimerization sequence 2, such that upon introduction into a cell and expression of the nucleic acid, dimerization sequence 1 associates with dimerization sequence 2 to form a new candidate peptide structure.

Suitable dimerization sequences will encompass a wide variety of sequences. Any number of protein-protein interaction sites are known (for example, see description of dimerization sequences set forth in WO 99/51625, incorporated herein by reference). In addition, dimerization sequences may also be elucidated using standard methods such as the yeast two hybrid system, traditional biochemical affinity binding studies, or even using the present methods.

In a preferred embodiment, the fusion partner is a selection gene or a reporter gene.

By "reporter gene" or "selection gene" or grammatical equivalents herein is meant a gene that by its presence in a cell (i.e. upon expression) can allow the cell to be distinguished from a cell that does not contain the reporter gene. Reporter genes can be classified into several different types, including detection genes, survival genes, death genes and cell cycle genes.

In the screening methods described below, which use cDNA libraries, expression of the cDNA causes the effect distinguishing between cells expressing the reporter gene and those that do not. As is more fully outlined below, additional components, such as substrates, ligands, etc., may be additionally added to allow selection or sorting on the basis of the reporter gene.

In an especially preferred embodiment, the reporter gene encodes a detectable protein that can be used as a direct label, for example a detection gene for sorting the cells or for cell enrichment by FACS. In this embodiment, the protein product of the reporter gene itself can serve to distinguish cells that are expressing the reporter gene. In this embodiment, suitable reporter genes include those encoding a luciferase gene from firefly, *Renilla*, or *Ptiolosarcus*, as well as genes encoding green fluorescent protein (GFP; Chalfie, M. et al. (1994) Science 263: 802–05; and EGFP; Clontech—Genbank Accession Number U55762), blue fluorescent protein (BFP; Quantum Biotechnologies, Inc. 1801 de Maisonneuve Blvd. West, 8th Floor, Montreal (Quebec) Canada H3H 1J9; Stauber, R. H. (1998) Biotechniques 24: 462–71; Heim, R. et al. (1996) Curr. Biol. 6: 178–82), enhanced yellow fluorescent protein (EYFP; 1. Clontech Laboratories, Inc., 1020 East Meadow Circle, Palo Alto, Calif. 94303), luciferase (Kennedy, H. J. et al. (1999) J. Biol. Chem. 274: 13281–91), *Renilla reniformis* GFP (WO 99/49019), *Ptilosarcus gumeyi* GFP (WO 99/49019; U.S. Ser. No. 60/164,592; U.S. Ser. No. 09/710,058; U.S. Ser. No. 60/290,287), *Renilla mulleris* GFP (WO 99/49019; U.S. Ser. No. 60/164,592; U.S. Ser. No. 09/710,058; U.S. Ser. No. 60/290,287); GFP homologue from *Anthozoa* species (Nat. Biotech., 17:969–973, 1999); β-galactosidase (Nolan, G. et al. (1988) Proc. Natl. Acad. Sci. USA 85: 2603–07), β-glucouronidase (Jefferson, R. A. et al. (1987) EMBO J. 6: 3901–07; Gallager, S., "GUS Protocols: Using the GUS Gene as a reporter of gene expression," Academic Press, Inc., 1992), and secreted form of human placental alkaline phosphatase, SEAP (Cullen, B. R. et al. (1992) Methods Enzymol. 216: 362–68). In a preferred embodiment, the codons of the reporter genes are optimized for expression within a particular organism, especially mammals, and particularly preferred for humans (see Zolotukhin, S. et al. (1996) J. Virol. 70: 4646–54; U.S. Pat. No. 5,968,750; U.S. Pat. No. 6,020,192; U.S. Ser. No. 60/290,287, all of which are expressly incorporate by reference).

The green fluorescent protein from Aequorea Victoria is a 238 amino add protein. The crystal structure of the protein and of several point mutants has been solved (Ormo et al., Science 273, 1392–5, 1996; Yang et al., Nature Biotechnol. 14, 1246–51, 1996). The fluorophore, consisting of a modified tripeptide, is buried inside a relatively rigid beta-can structure, where it is almost completely protected from solvent access. The fluorescence of this protein is sensitive to a number of point mutations (Phillips, G. N., Curr. Opin. Struct. Biol. 7, 821–27, 1997). The fluorescence appears to be a sensitive indication of the preservation of the native structure of the protein, since any disruption of the structure allowing solvent access to the fluorophoric tripeptide will quench the fluorescence.

The *Renilla* GFP preferred for use in the present invention preferably has significant homology to the wild-type *Renilla* GFP protein as depicted in WO 99/49019, hereby incorporated by reference in its entirety.

Alternatively, the reporter gene encodes a protein that will bind a label that can be used as the basis of the cell enrichment (sorting); that is, the reporter gene serves as an indirect label or detection gene. In this embodiment, the reporter gene should encode a cell-surface protein. For example, the reporter gene may be any cell-surface protein not normally expressed on the surface of the cell, such that secondary binding agents serve to distinguish cells that contain the reporter gene from those that do not. Alternatively, albeit non-preferably, reporters comprising normally expressed cell-surface proteins could be used, and differences between cells containing the reporter construct and those without could be determined. Thus, secondary binding agents bind to the reporter protein. These secondary binding agents are preferably labeled, for example with fluorophores, and can be antibodies, haptens, etc. For example, fluorescently labeled antibodies to the reporter gene can be used as the label. The use of such secondary binding agents is particularly desirable for use with FACS. Similarly, membrane-tethered streptavidin could serve as a reporter gene, and fluorescently-labeled biotin could be used as the label, i.e. the secondary binding agent. Alternatively, the secondary binding agents need not be labeled as long as the secondary binding agent can be used to distinguish the cells containing the construct; for example, the secondary binding agents may be used in a column, and the cells passed through, such that the expression of the reporter gene results in the cell being bound to the column, and a lack of the reporter gene (i.e. inhibition), results in the cells not being retained on the column. Other suitable reporter proteins/secondary labels include, but are not limited to, antigens and antibodies, enzymes and substrates (or inhibitors), etc.

In a preferred embodiment, the reporter gene is a survival gene that serves to provide a nucleic acid (or encode a protein) without which the cell cannot survive, such as drug resistance genes. In this embodiment, expressing the survival gene allows selection of cells by identifying cells that survive, for example in presence of a selection drug. Examples of drug resistance genes include, but are not limited to, puromycin resistance (puromycin-N-acetyl-transferase) (de la Luna, S. and Ortin, J. Methods Enzymol. (1992) 216:376–385), G418 neomycin resistance gene, hygromycin resistance gene (hph), and blasticidine resistance genes (bsr, brs, and BSD)(Pere-Gonzalez, et al., Gene (1990).86: 129–134; Izumi et al.,. Exp. Cell Res. (1991) 197: 229–233; Itaya et al. (1990) J. Biochem. 107: 799–801; Kimura, et al. Mol. Gen. Genet. (1994) 242: 121–129). In addition, generally applicable survival genes are the family of ATP-binding cassette transporters, including multiple drug resistance gene (MDR1) (see Kane et. al. (1988) Mol. Cell. Biol. 8: 3316 and Choi et al. (1988) Cell 53: 519), multidrug resistance associated proteins (MRP) (Bera T. K. et al. (2001) Mol. Med. 7:509–16), and breast cancer associated protein (BCRP or MXR) (Tan B. et al. (2000) Curr. Opin. Oncol. 12:450–8). When expressed in cells, these selectable genes can confer resistance to a variety of anticancer drugs (i.e. methotrexate, colchicine, tamoxifen, mitoxanthrone, and doxorubicin).

In a preferred embodiment, the reporter gene is a death gene, which encodes a protein that causes the cells to die. Death genes fall into two basic categories: death genes that encode death proteins that require a death ligand to kill the cells, and death genes that encode death proteins that kill cells as a result of high expression within the cell, and do not require the addition of any death ligand. In one embodiment, cell death requires a two-step process: the expression of the death gene and induction of the death phenotype with a signal or ligand, such that the cells may be grown up expressing the death gene, and then induced to die. A number of death genes/ligand pairs are known, including, but not limited to, the Fas receptor and Fas ligand (Bodmer, et al. (1997) J. Biol. Chem. 272:18827–18833; Gonzalez-Cuadrado, et al. (1997) Kidney Int. 51:1739–1746; Muruva, et al. (1997) Hum Gene Ther., 8:955); p450 and cyclophosphamide (Chen, et al. (1997) Cancer Res 57:48304837); thymidine kinase and gangcylovir (Stone, R. (1992) 256: 1513), tumor necrosis factor (TNF) receptor and TNF. Alternatively, the death gene need not require a ligand, and death results from high expression of the gene; for example, the overexpression of a number of programmed cell death (PCD) proteins are known to cause cell death, including, but not limited to, caspases, bax, TRADD, FADD, BADD, SCK, MEK, etc. Still other death genes require only moderate levels of expression to be lethal to a cell, and are more aptly referred to as toxins. These genes encode products including, but not limited to, anthrax toxin (Pannifer et al., Nature 414(6860):229–233 (2001)), botulinum toxin, pertussis toxin, cholera toxin, *Clostridium difidle* toxin A & B (Just et al., Int. J. Med. Microbiol. 291(4):243–250 (2001)) α-toxin, tetanus toxin, hemolysin (Worsham et al., Biochem. 40(45): 3607–3616 (2001)) and cytolethal distending toxins (Cortes-Bratti et al., Toxicon. 39(11):729–736 (2001)).

In a preferred embodiment, the reporter gene is a cell cycle gene, that is, a gene that causes alterations in the cell cycle. For example, Cdk interacting protein p21 (see Harper et al. (1993) Cell 75: 805–816), which inhibits cyclin dependent kinases, does not cause cell death but causes cell-cycle arrest. Thus, expressing the p21 allows selection for regulators of promoter activity or regulators of p21 activity based on detecting cells that grow out much more quickly due to low p21 activity, either through inhibiting promoter activity or inactivation of p21 protein activity. As will be appreciated by those in the art, it is also possible to configure the system to select cells based on their inability to grow out due to increased p21 activity.

In a preferred embodiment, the fusion partner includes a linker or tethering sequence.

Linkers may comprise nucleic acid encoding protein to form a protein linker or tether. Alternatively, linkers may be separation sequences that provide for the expression of separate proteins.

Linker sequences between various targeting sequences (for example, membrane targeting sequences) and the other components of the constructs (such as the candidate agents, i.e., cDNA expression products) may be desirable to allow the candidate agents to interact with potential targets unhindered. For example, when the candidate bioactive agent is a peptide, useful linkers include glycine-serine polymers (including, for example, $(GS)_n$, $(GSGGS)_n$ (SEQ ID NO:52) and $(GGGS)_n$, (SEQ ID NO:53) where n is an integer of at least one), glycine-alanine polymers, alanine-serine polymers, and other flexible linkers such as the linker for the shaker potassium channel, and a large variety of other flexible linkers, as will be appreciated by those in the art. Glycine-serine polymers are preferred since both of these amino acids are relatively unstructured, and therefore may be able to serve as a neutral linker between components. Secondly, serine is hydrophilic and therefore able to solubilize what could be a globular glycine chain. Third, similar chains have been shown to be effective in joining subunits of recombinant proteins such as single chain antibodies.

In a preferred embodiment, the linker is a separation sequence. Separation sequences include, but are not limited to, IRES, type 2a site, and peptidase cleavage sites, all of which are described below in reference to the preferred embodiment of retroviral vectors.

In addition, the fusion partners, including presentation structures, may be modified, randomized, and/or matured to alter the presentation orientation of the candidate agent. For example, determinants at the base of the loop may be modified to slightly modify the internal loop peptide tertiary structure, while maintaining the amino acid sequence of the cDNA encoded polypeptide moiety.

In a preferred embodiment, combinations of fusion partners are used. Thus, for example, any number of combinations of presentation structures, targeting sequences, rescue sequences, and stability sequences may be used, with or without linkers.

In one aspect, the cDNA expression vectors provided herein are lentiviral vectors. As is known, lentiviruses, such as HIV virus, are capable of infecting both dividing and non-dividing cells. Vectors based on HIV viruses and packaging methods are known in the art (see Miyoshi, H. (1998) J. Virol. 72: 8150–57; Zufferey, R. (1998) J. Virol. 72: 9873–80; Iwakuma, T. (1999) Virology 261: 120–32; Xu, K (2001) Mol. Ther. 3: 97–104).

In one aspect of the invention, the cDNA expression vectors provided herein are retroviral vectors.

Accordingly, provided herein are retroviral cDNA expression vector libraries. Each library comprises a plurality of retroviral cDNA expression vectors.

As used herein, "retroviral vector" refers to a retroviral genome which is other than a naturally occurring retroviral genome.

By retroviral genome herein is meant an RNA which is capable of being reverse transcribed (to DNA) and incorporated into the genome of a cell infected by a retroviral particle comprising the retroviral genome via the activity of the enzymatic proteins of the particle. Complete retroviral genomic maps have been produced for many different retroviruses (see *Appendix 2: Retroviral taxonomy, protein structures, sequences, and genetic maps*, In "Retroviruses", (Coffin et al., eds.) Cold Spring Harbor Laboratory Press, Cold Spring Harbor, N.Y. (1997), pp. 757–805), incorporated herein), and retrovirus replication cycle has been extensively studied (see John M. Coffin, *Retroviridae: The Viruses and Their Replication*, In "Virology", Volume 2, Third Edition (Fields et al., eds.), Lippincot-Raven Publishers, Philadelphia, Pa. (1996), pp. 1767–1847, also incorporated herein). Retroviral genomes and vectors useful in the present invention may be derived from any retrovirus. The skilled artisan will appreciate that the selection of a retrovirus for use in the invention will be based largely upon the intended use, particularly on the type of cell to be infected by a retroviral particle comprising a retroviral genome of the invention, as described below. One preferred retrovirus upon which a retroviral genome of the invention is based is the Murine leukemia virus (MuLV).

In a preferred embodiment, the retroviral genome comprises a 5' long terminal repeat (LTR). The 5' LTR is generally the sequence at the 5' end of the retroviral genomic RNA which encodes untranslated sequences when the retroviral genome has been incorporated into the genome of the host. In a preferred embodiment, the 5' LTR comprises a terminal redundant region (R region) and a 5' unique region (U5 region).

In a preferred embodiment, the retroviral genome comprises a 3' LTR, which is generally the 3' end of the retroviral genomic RNA which encodes un-translated sequences. Preferably, the 3' LTR comprises an R region (identical to the R region found at the 5' end) and a 3' unique region (U3). Preferably, the 3' LTR also comprises a poly adenosine terminal sequence (poly-A tail). In a preferred embodiment the poly-A tail is from 20–60 residues long, preferably about 40 residues long.

In a preferred embodiment, the retroviral genome is a modified MMLV genome and comprises a composite CMV promoter fused to the transcriptional start site of the MMLV R-U5 region of the LTR, an extended packaging sequence, and deletion of the MMLV Gag start ATG. For example, see Lorens et. al., Mol. Therapy, 1:438–447, 2000. This recombinant promoter is sometimes referred to herein as "CRU5".

The different components of the retroviral genome have been widely studied and are well known in the art (see Coffin, above). The retroviral genome may comprise other un-translated sequences, besides those mentioned above, including a primer binding site, adjacent to the U5 region, at which point the tRNA contained within the retroviral particle binds to the retroviral genome to initiate reverse transcription after infection of a host (see Coffin, above). The retroviral genome may also comprise a leader sequence between the 5' LTR and the internal translated region. In addition, the retroviral genome may comprise a polypurine tract immediately 5' to the U3 region.

"Retroviral vectors" as used herein also refers to vectors used to introduce into a host the cDNA nucleic acids of the present invention in the form of an RNA viral particle, as is generally outlined in PCT US 97/01019 and PCT US 97/01048, both of which are incorporated by reference. Various retroviral vectors are known, including a vector based on the murine stem cell virus (MSCV) (see Hawley, R. G. et al. (1994) Gene Ther. 1: 136–38), modified MFG virus (Riviere, I. et al. (1995) Genetics 92: 6733–37), pBABE (see PCT US97/01019), and pCRU5 (Naviaus, R. K. et al. (1996) J. Virol. 70: 5701–05), all of which are incorporated by reference. In addition, particularly well suited retroviral transfection systems for generating retroviral vectors are described in Mann et al., supra; Pear, W. S. et al. (1993) Pro. Natl. Acad. Sci. USA 90: 8392–96; Kitamura, T. et al. (1995) Proc. Natl. Acad. Sci. USA 92: 9146–50; Kinsella, T. M. et al. (1996) Hum. Gene Ther. 7: 1405–13; Hofmann, A. et al. (1996) Proc. Natl. Acad. Sci. USA 93: 5185–90; Choate, K. A. et al. (1996) Hum. Gene Ther. 7: 2247–53; WO 94/19478; PCT US97/01019, and references cited therein, all of which are incorporated by reference.

In a preferred embodiment, the retroviral vectors are self-inactivating retroviral vectors or SIN vectors.

By "self-inactivating, or "SIN" or grammatical equivalents herein is meant retroviral vectors in which the viral promoter elements are rendered ineffective or inactive (see Yu, S.-F. et al. (1986) Proc. Natl. Acad. Sci. USA 83: 3094–84). These promoter and enhancer elements are present in the 3' long terminal repeat (3' LTR), which is composed of segments designated as U3 and R (see Fields, B. N. et al. Virology, Vol. 2, Lippincott-Raven Publishers, New York, N.Y., 1996, pg 1767–1847). The integrated retroviral genome, called the provirus, is bound by two LTRs and is transcribed from the 5' LTR to the 3' LTR. The viral promoters and enhancers reside primarily in the U3 region of the 3' LTR, but the 3' LTR region is duplicated at the 5' LTR during viral replication and integration. The promoter situated at the 5' LTR directs expression of virally encoded genes and generates the RNA copies that are packaged into viral particles.

The self-inactivating feature of SIN vectors arises from the mechanism of viral replication and integration (see Coffin, J. M. "*Retroviridae: The Viruses and Their Replication*" in Virology: Vol 2, Fields et al., ed., Uppincoft-Raven Publishers, New York, pg 1767–1847). Following entry of the retrovirus into a cell, a tRNA molecule binds to the primer binding region (PB) at the 5' end of the viral RNA. Extension of the tRNA primer by reverse transcriptase results in a tRNA linked to a DNA segment containing the U5 and R sequences present at the 5' end of the viral RNA. RNase activity of reverse transcriptase acts on the viral RNA strand of the DNA/RNA hybrid, thus releasing the elongated tRNA, which then hybridizes to complementary R sequences present on the 3' end of the viral RNA. Elongation by reverse transcriptase results in synthesis of a DNA copy of the viral genome (minus strand DNA) and degradation of the RNA strand by RNase. A short RNA sequence designated the PP sequence, which is resistant to RNase action, remains hybridized to the newly synthesized DNA strand—generally at a region immediately preceding the U3 region at the 3' end of the viral genome—and acts as a primer for replication of the complementary strand (plus strand DNA). Extension of this PP primer results in replication of sequences comprising U3, R, U5, and PB segments, which eventually becomes the 5' LTR of the integrated virus. Subsequently, the PB region of the extended primer hybridizes to the complementary PB region present on the 3' end of the minus strand DNA, and subsequent extension of this hybrid results in synthesis of a double strand DNA intermediate in which the 5' and 3' LTR contain the U3, R, and U5 segments. Following replication and transport into the nucleus, the viral double stranded DNA integrates into the host chromosome via the attachment sites (aft) present near the ends of the LTRs to generate the integrated provirus.

Since the mechanism of viral replication results in duplication of the promoter elements at the 3' LTR to the 5' LTR of the integrated virus, inactivating or replacing the viral promoter results in inactivating or replacing the promoter normally present in the proviral 5' LTR. This feature describes the self-inactivating nature of these retroviral vectors. Inactivation of the 5' LTR promoter reduces expression of the proviral nucleic acid from the 5' LTR and reduces the potential deleterious effects arising from influences on cellular genes by the viral promoter present on the 3' LTR of the integrated virus.

"Retroviral vector" as used herein also refers to plasmid-based expression vectors comprising requisite cis-elements of a retroviral genome, including transcriptional and translational regulatory sequences, and packaging sequences, or functional variants thereof, which are required for the production of retroviral particles and packaging of vector into particles. By requisite ds-elements is meant those elements which are necessary for packaging the plasmid-based expression vector as a retroviral genome in a retroviral particle, and which are not supplied by other means, for example in trans by a host cell, as described below.

As used herein, retroviral vector also refers to retroviral particles comprising: a) a retroviral genome which is other than naturally occurring; or b) a plasmid-based retroviral expression vector as described above.

Preferred particles are not capable of replication after infection of a host cell which is other than a host cell that provides essential retroviral factors in trans for synthesizing and packaging retrovirus (for example, known packaging cell lines). Thus, these particles are typically capable of a single infection.

A retroviral expression vector system is generally described in PCT/US97/01019 and PCT/US97/01048, both of which are expressly incorporated herein by reference.

In one aspect, the present invention provides methods for producing retroviral cDNA expression vector libraries, which include retroviral particles.

The use of recombinant retroviruses was pioneered by Richard Mulligan and David Baltimore with the Psi-2 lines and analogous retrovirus packaging systems, based on NIH 3T3 cells (see Mann et al., Cell 33:153–159 (1993), hereby incorporated by reference). Such helper-defective packaging lines are capable of producing all the necessary trans proteins -gag, pol, and env- that are required for packaging, processing, reverse transcription, and integration of recombinant genomes. Those RNA molecules that have in cis the ψ packaging signal are packaged into maturing virions. Retroviruses are preferred for a number of reasons. First, their derivation is easy. Second, unlike Adenovirus-mediated gene delivery, expression from retroviruses is long-term. Adeno-associated viruses have limited space for genes and regulatory units and there is some controversy as to their ability to integrate. Retroviruses therefore offer the best current compromise in terms of long-term expression, genomic flexibility, and stable integration, among other features. The main advantage of retroviruses is that their integration into the host genome allows for their stable transmission through cell division. This ensures that in cell types which undergo multiple independent maturation steps, such as hematopoietic cell progression, the retrovirus construct will remain resident and continue to express.

A particularly well suited retroviral transfection system is described in Mann et al., supra: Pear et al., PNAS USA 90(18):8392–6 (1993); Kitamura et al., PNAS USA 92:9146–9150 (1995); Kinsella et al., Human Gene Therapy 7:1405–1413; Hofmann et al., PNAS USA 93:5185–5190; Choate et al., Human Gene Therapy 7:2247 (1996); and WO 94/19478; and references cited therein, all of which are incorporated by reference.

In one embodiment of the invention, the library is generated in a retrovirus DNA construct backbone. Description of an appropriate retroviral DNA construct backbone is found in Lorens et. al., Mol. Therapy, 1:438–447, 2000, incorporated herein by reference.

Any number of suitable retroviral vectors may be used. Generally, the retroviral vectors include a second nucleic acid encoding a detectable protein moiety or selection gene. Retroviral vectors may also include separation linkers such as an IRES, type 2a sequence, or cleavage site encoding sequence, as described herein. Retroviral vectors may also include promoters driving expression of a second gene, placed in sense or anti-sense relative to the 5' LTR. Suitable selection genes include, but are not limited to, neomycin, blastocidin, bleomycin, puromycin, and hygromycin resistance genes, as well as self-fluorescent markers such as green fluorescent protein, enzymatic markers such as lacZ, and surface proteins such as CD8, etc. In a preferred embodiment, the second nucleic acid encodes a GFP from *Aequorea, Renilla*, or *Ptilosarcus* species, as described herein.

Preferred vectors include a vector based on the murine stem cell virus (MSCV) (see Hawley et al., Gene Therapy 1:136 (1994)) and a modified MFG virus (Rivere et al., Genetics 92:6733 (1995)), and PBABE, (see Moregenstern et. al., Nuc. Acids Res. 18:3587–3596, 1990; Nolan et. al., U.S. Pat. No. 6,153,380 issued Nov. 28, 2000; Hofmann et. al., Proc. Nat'l. Acad. Sci., 93:51855190, 1996; all expressly incorporated herein by reference. Another preferred vector is based on the murine leukemia virus (for example, see Lorens et. al., Mol. Therapy, 1:438–447, 2000).

The retroviruses may include inducible and constitutive promoters. Inducible expression may be desired, for example to provide for turning cDNA-encoded peptide or antisense nucleic acid expression on and off during the selection process in screening methods described herein to confirm the effect of candidate agent or to ensure the survival of producer cells in which prolonged candidate agent expression may be lethal.

In addition, it is possible to configure a retroviral vector to allow inducible expression of retroviral inserts after integration of a single vector in target cells; importantly, the entire system is contained within the single retrovirus. Tet-inducible retroviruses have been designed incorporating the Self-Inactivating (SIN) feature of 3' LTR enhancer/promoter retroviral deletion mutant (Hoffman et al., PNAS USA 93:5185 (1996)). Expression of this vector in cells is virtually undetectable in the presence of tetracycline or other active analogs. However, in the absence of Tet, expression is turned on to maximum within 48 hours after induction, with uniform increased expression of the whole population of cells that harbor the inducible retrovirus, indicating that expression is regulated uniformly within the infected cell population. A similar, related system uses a mutated Tet DNA-binding domain such that it bound DNA in the presence of Tet, and was removed in the absence of Tet. Either of these systems is suitable. For the Tet inducible system, see also U.S. Ser. No. 10/096,339, filed Mar. 8, 2002, incorporated herein by reference.

A preferred inducible promoter for use in the present invention is a tet-inducible promoter comprising multiple copies of the tet operon operably linked to a minimal human CMV promoter (for example, see Gossen et al., PNAS 89:5547–5551, 1992).

Delivery of the retroviral cDNA expression vectors, described herein, into a retroviral packaging system results in conversion to infectious virus. Suitable retroviral packaging system cell lines include, but are not limited to, the Bing and BOSC23 cell lines described in WO 94/19478; Soneoka et al., Nucleic Acid Res. 23(4):628 (1995); Finer et al., Blood 83:43 (1994); Pheonix packaging lines such as PhiNX-eco and PhiNX-ampho, described below; 292T+ gag-pol and retrovirus envelope; PA317; and cell lines outlined in Markowitz et al., Virology 167:400 (1988), Markowitz et al., J. Virol. 62:1120 (1988), Li et al., PNAS USA 93:11658 (1996), Kinsella et al., Human Gene Therapy 7:1405 (1996), all of which are incorporated by reference.

Preferred systems include PhiNX-eco and PhiNX-ampho or similar cell lines, which are two cells lines as follows. The cell lines are based on the BING and BOSC23 cell lines described in WO 94/19478, which are based on the 293T cell line (a human embryonic kidney line transformed with adenovirus E1 a and carrying a temperature sensitive T antigen co-selected with neomycin). The unique feature of this cell line is that it is highly transfectable with either calcium phosphate mediated transfection or lipid-based transfection protocols—greater than 50% of 293T cells can be transiently transfected with plasmid DNA. Thus, the cell line is a cellular milieu in which retroviral structural proteins and genomic viral RNA can be brought together rapidly for creation of helper-defective virus. 293T cells were therefore engineered with stably integrated defective constructs capable of producing gag-pol, and envelope protein for either ecotropic or amphotropic viruses. These lines were called BOSC23 and Bing, respectively. The utility of these lines was that one could produce small amounts of recombinant virus transiently for use in small-scale experimentation. The lines offered advantages over previous stable systems in that virus could be produced in days rather than months.

Two problems became apparent with these first generation lines over the first two years they were in wide use. First, gag-pol and envelope expression was unstable and the lines required vigilant checking for retroviral production capacity; second the structure of the vectors used for protein production were not considered fully "safe" for helper virus production; and third, one of the lines was shown to be inadvertently carrying a hygromycin-containing retrovirus. Although the BING and BOSC23 lines are useful in the present invention, all of these potentially problematic issues are addressed in the PhiNX second-generation lines. These lines are based on 293T cells as well, with the following improvements. First, the ability to monitor gag-pol production on a cell-by cell basis was made by introducing an IRES-CD8 surface marker expression cassette downstream of the reading frame of the gag-pol construct (other surface markers besides CD8 are also useful). IRES (internal ribosome entry site) sequences allow secondary or tertiary protein translation from a single mRNA transcript. Thus, CD8 expression is a direct reflection of intracellular gag-pol and the stability of the producer cell population's ability to produce gag-pol can be readily monitored by flow cytometry. Second, for both the gag-pol and envelope constructs non-Moloney promoters were used to minimize recombination potential with introduced retroviral constructs, and different promoters for gag-pol and envelope were used to minimize their inter-recombination potential. The promoters used were CMV and RSV. Two cell lines were created, PHEONIX-ECO and PHEONIX-AMPHO. Gag-pol was introduced with hygromycin as the co-selectable marker and the envelope proteins were introduced with diptheria resistance as the co-selectable marker. Finally, the cells were screened to find a relatively rare cell type that produced gag-pol and env in a uniform distribution, although this is not required. In addition, a line termed PHEONIX-gp has been produced that expresses only gag-pol. This line is available for further pseudotyping of retroviral virions with other envelope proteins such as gibbon ape leukemia virus envelope or Vesicular Stomatitus VSV-G protein, Xenotropic, or retargeting envelopes can also be added.

Both PHEONIX-ECO and PHEONIX-AMPHO were tested for helper virus production and established as being helper-virus free. Both lines can carry episomes for the creation of stable cell lines which can be used to produce retrovirus. Both lines are readily testable by flow cytometry for stability of gag-pol (CD8) and envelope expression; after several months of testing the lines appear stable, and do not demonstrate loss of titre as did the first-generation lines BOSC23 and Bing (partly due to the choice of promoters driving expression of gag-pol and envelope). Both lines can also be used to transiently produce virus in a few days. Thus, these new lines are fully compatible with transient, episomal stable, and library generation for retroviral gene transfer experiments. Finally, the titres produced by these lines have been tested. Using standard polybrene-enhanced retroviral infection, titres approaching or above $10^7$ per ml were observed for both PHEONIX-eco and PHEONIX-ampho when carrying episomal constructs. When transiently produced virus is made, titres are usually ½ to ⅓ that value.

These lines are helper-virus free, carry episomes for long-term stable production of retrovirus, stably produce gag-pol and env, and do not demonstrate loss of viral titre over time. In addition, PhiNX-eco and PhiNX-ampho are capable of producing titres approaching or above $10^7$ per ml when carrying episomal constructs, which, with concentration of virus, can be enhanced to $10^8$ to $10^9$ per ml.

In a preferred embodiment, the cell lines disclosed above, and the other methods for producing retrovirus, are useful for production of virus by transient transfection. The virus can either be used directly or be used to infect another retroviral producer cell line for "expansion" of the library.

Concentration of virus may be done as follows. Generally, retroviruses are titred by applying retrovirus-containing supernatant onto indicator cells, such as NIH3T3 cells, and then measuring the percentage of cells expressing phenotypic consequences of infection. The concentration of the virus is determined by multiplying the percentage of cells infected by the dilution factor involved, and taking into account the number of target cells available to obtain a relative titre. If the retrovirus contains a reporter gene, such as lacZ, then infection, integration, and expression of the recombinant virus is measured by histological staining for lacZ expression or by flow cytometry (FACS). In general, retroviral titres generated from even the best of the producer cells do not exceed $10^7$ per ml, unless concentration by relatively expensive or exotic apparatus is done. However, as it has been recently postulated that since a particle as large as a retrovirus will not move very far by Brownian motion in liquid, fluid dynamics predicts that much of the virus never comes in contact with the cells to initiate the infection process. However, if cells are grown or placed on a porous filter and retrovirus is allowed to move past cells by gradual gravitometric flow, a high concentration of virus around cells can be effectively maintained at all times. Thus, up to a ten-fold higher infectivity by infecting cells on a porous membrane and allowing retrovirus supernatant to flow past them has been seen. This should allow titres of $10^9$ after concentration.

In one aspect, methods for constructing retroviral cDNA expression vectors, and libraries comprising the same, are provided herein. The methods involve the directional cloning of cDNA into a retroviral expression vector using adaptors that generate an SfiI site on one end of an adaptor-modified cDNA. In a preferred embodiment, directional cloning is used to operably link cDNA to a transcriptional regulatory sequence in sense configuration. By convention, mRNA is a sense strand. Therefore, operably linked to a transcriptional regulatory sequence in sense configuration means that an antisense strand serves as template for transcription. In a preferred embodiment, the cDNA additionally comprises a native translation start site such that a cDNA transcript will be translated in the same frame as the ORF of the corresponding mRNA. This ORF is sometimes referred to herein as the native ORF. Such a vector may be used to express a polypeptide encoded by the corresponding mRNA, or a fragment thereof.

Importantly, a cDNA encoded transcript from such a vector will only be translated if the cDNA comprises a native translation start site (i.e. sequence complementary to the translation start site of the corresponding mRNA). Use of this type of expression vector, which lacks an heterologous translation start site, to express polypeptides, selects for cDNAs that capture the 5' terminus of the ORF, as only these cDNAs are translated.

This type of vector is useful for the expression of cDNA restriction fragments as well. While cDNA restriction fragments comprising a 3' terminus GG or a 5' terminus CC, but not both, may be directionally cloned, the direction of insertion (sense or antisense) of each fragment is not known absent the determination of fragment ends. However, in general, only those fragments that comprise a native translation start site and are inserted in sense orientation will provide cDNA transcripts that will be translated.

A preferred transcriptional regulatory sequence comprises a composite CMV promoter fused to the transcriptional start site of the MMLV R-U5 region of the LTR. For example, see Lorens et. al., Mol. Therapy, 1:438–447, 2000.

Directional cloning may also be used to operably link cDNA to a transcriptional regulatory sequence in antisense configuration (i.e. sense sequence serving as template for transcription). Such a retroviral vector may be used to express antisense nucleic acid.

If desired, an heterologous translation start site may be included in the retroviral expression vector, resulting in the translation of antisense encoded peptide, provided a stop translation codon is not encountered. In addition, cDNA in sense orientation may be translated in frame or out of frame under the control of an heterologous translation regulatory sequence, depending on the location of the cDNA relative to the regulatory sequence. Ir addition, cDNA fragments lacking a native translation start site may be translated under the control of an heterologous translation start site.

In a preferred embodiment, the retroviral expression vector library made by methods provided herein comprises a plurality of retroviral expression vectors, each vector comprising a) a first nucleic acid comprising a cDNA; b) a second nucleic acid which encodes a fusion partner; and c) a transcriptional regulatory sequence (sometimes referred to herein as a transcriptional regulatory region) recognized by a host cell. The first and second nucleic acids form a fusion nucleic acid which is operably linked to the transcriptional regulatory sequence. The vectors may additionally comprise a translational regulatory sequence that initiates translation of the fusion nucleic add, as described below. However, vectors lacking an heterologous translation start site are preferred.

In a preferred embodiment, the fusion partner is a detectable protein (sometimes referred to herein as detectable protein moiety) as described herein.

In a preferred embodiment, the first nucleic acid is fused to the 5' end of the second nucleic acid. The expression products of such a vector include a fusion nucleic acid wherein cDNA encoded sequence is located at the 5' end and nucleic acid sequence encoding detectable protein is located at the 3' end.

The expression products of such a vector also include a fusion protein. Such a fusion protein comprises an N-terminal polypeptide encoded by cDNA and a C-terminal polypeptide which is a detectable protein moiety.

In a preferred embodiment, the expression vector does not include an heterologous translation start site. Rather, translation of the fusion protein relies on a translation start site being present in the cDNA, rather than the vector. In this way, the expression vectors selectively express at the protein level only those cDNAs that extend 5' to the end of the ORF, covering the translation start site.

Where cDNA is cloned in antisense orientation, the expression products include a fusion nucleic acid wherein antisense nucleic acid is located at the 5' end and nucleic acid sequence encoding detectable protein is located at the 3' end.

It will be appreciated that such an antisense nucleic acid may be used to inhibit the normal RNA processing/editing and/or translation of a host cell mRNA, particularly the corresponding mRNA used for cDNA synthesis and mRNAs related thereto by sequence. Importantly, an advantage of such fusion antisense nucleic acids is the stability conferred to the fusion nucleic add by inclusion of the second nucleic acid sequence which encodes a detectable protein moiety. A fusion nucleic acid of this sort in general provides an antisense nucleic acid that is more stable than antisense nucleic acid alone and is potentially more potent as an inhibitor of native mRNA processing/editing and/or translation.

If desired, an heterologous translation start site may be included in the expression vector to allow for translation of the fusion nucleic acid. cDNA in sense orientation will be translated in frame or out of frame relative to the native ORF, depending on its location relative to the regulatory sequence. cDNAs that do not comprise native translation start sites, including some cDNA restriction fragments, will be translated. In addition, antisense cDNA transcripts will be translated under the control of an heterologous translation regulatory sequence. Some cDNA inserts of the present expression vectors may also include nucleic acid sequence corresponding to untranslated mRNA sequence. These sequences may also be translated under the control of a heterologous translation start site. In addition, some vectors may harbor a native translation start site provided by the cDNA. As such, some vectors may comprise more than one translation start site.

In one embodiment, CAP oligonucleotides are used to increase the full length character of cDNAs that are cloned for expression.

In one embodiment, CAP oligonucleotides are combined with random primers to yield cDNA that is biased towards the 5' end, as described herein.

In one embodiment, CAP oligos are engineered to introduce 3' terminus GG sequence into cDNA.

In one embodiment, the first nucleic acid is fused to the 3' end of the second nucleic acid. The expression products of such a vector include a fusion nucleic acid wherein cDNA encoded sequence is located at the 3' end and nucleic acid sequence encoding detectable protein is located at the 5' end.

The expression products of such a vector also include a fusion protein. Such a fusion protein comprises an C-terminal polypeptide encoded by cDNA and an N-terminal polypeptide which is a detectable protein moiety. Termination of translation of the fusion protein is ensured by the incorporation of a triple frame translation stop sequence in the vector immediately downstream of the cDNA insert.

In this embodiment, translation begins with the transcript of the second nucleic acid, and a translation start site is engineered in the vector or in the second nucleic acid to provide for the initiation of translation.

A cDNA insert may include an mRNA's 5' untranslated sequence, which may be translated in the context of the fusion nucleic acid. Additionally, cDNAs inserted in sense orientation may be translated in one of three possible frames. One frame is the same as that of the native ORF of the corresponding mRNA, while the other two frames provide for the expression of "random" polypeptides. Of course the sequence of such random polypeptides is dictated by the sequence of cDNA, which is in turn dictated by the sequence of template mRNA. By "random" is meant that the amino add sequence of the polypeptide expression product does not correspond to the amino acid sequence encoded by the native ORF.

Where cDNA is cloned in antisense orientation, the expression products include a fusion nucleic acid wherein antisense nucleic acid is located at the 3' end and nucleic add sequence encoding detectable protein is located at the 5' end. Importantly, an advantage of such fusion antisense nucleic adds is the stability conferred to the fusion nucleic acid by inclusion of the second nucleic add sequence which encodes a detectable protein moiety. A fusion nucleic acid of this sort in general provides an antisense nucleic acid that is more stable than antisense nucleic acid alone and is potentially more potent as an inhibitor of native mRNA processing/ editing and/or translation.

The expression products of such a vector also include a fusion protein, comprising an N-terminus peptide which is a detectable protein moiety, and a C-terminal peptide which is encoded by antisense nucleic acid, provided a stop codon is not encountered.

In a preferred embodiment, expression vectors additionally comprise a third nucleic add sequence which is a linker, as described herein, interposed between the first and second nucleic acids.

In this embodiment, the linker may encode a protein to form a protein linkage (or tether) between cDNA-encoded protein and detectable protein moieties, as described herein, or may be a separation sequence, as described herein.

When the linker encodes a protein tether, expression products include a fusion protein additionally comprising a protein tether that separates the cDNA-encoded polypeptide from the detectable protein moiety in the fusion protein. The tether sequence may be desirable to allow the cDNA encoded polypeptide to interact with potential targets unhindered.

In a preferred embodiment, the first nucleic acid is fused to the second nucleic acid through a linker which is a separation sequence. In a preferred embodiment, the first nucleic acid is fused to the 5' end of the second nucleic acid through a linker. In another embodiment, the first nucleic acid is fused to the 3' end of the second nucleic acid through a linker.

In a preferred embodiment, the linker connecting the first and second nucleic acids comprises an internal ribosome entry sequence (IRES). IRES sequences are well known in the art, for example see Jackson et. al., Trends in Biochem. Sci., 15:477–483, 1990. Such a linker may be used to fuse the first nucleic acid to the 5' end or the 3' end of the second nucleic acid. The expression products of such a vector include a fusion nucleic acid and two separate polypeptides translated from a fusion nucleic acid, particularly a first polypeptide which is encoded by a cDNA fragment, and a second polypeptide which is a detectable protein. In a preferred embodiment, cDNA is located 5' of nucleic acid encoding detectable protein.

IRES sequences provide for CAP (here used to refer to 7-methyl-Gppp cap) independent initiation of translation (Kim, et al. (1992) Mol. Cell. Biol. 12:3636–3643; McBratney, et al. (1993) Current Opinion in Cell Biology 5:961–65) and appear to act by recruiting 40S ribosomal subunit to the mRNA in the absence of translation initiation factors required for normal CAP dependent translation initiation. IRES sequences are heterogenous in nucleotide sequence, RNA structure, and factor requirements for ribosome binding and are frequently located on the untranslated leader regions of RNA viruses, such as the Picomaviruses. The viral sequences range from about 450–500 nucleotides in length, although IRES sequences may also be shorter or longer (Adam, et al. J. Virol. (1991) 65, 4985–4990; Borman et al. (1997) Nucleic Acids Res 25:925–32; Hellen, et al. (1995) Curr. Top. Microbiol. Immunol. 203: 39–63 Mounfford, et al. (1995) Trends Genet. 11: 179–184). One embodiment of the IRES separation sites are the Type I IRESs present in enteroviral and rhinoviral sequences. These sequences are not efficient initiators of translations. A more preferred embodiment of IRESs are Type II sequences of cardioviruses and aphtoviruses (i e. encephalomyocarditis virus, see Elroy-Stein et al. (1989) Proc. Natl. Acad. Sci. USA, 86: 6126–30.), which are efficient initiators of translation. Another embodiment are Type III IRES sequences, such as those found in hepatitis A viruses. Also useful in the present invention include IRES sequences found in other viruses: avian reticuloendotheleliosis virus (Lopez-Lastra, et al. (1997) Hum. Gene Ther. 8: 1855–65), Moloney murine leukemia virus (Vagner et al., (1995) J. Biol. Chem. 270: 20376–83), short IRES segments of hepatitis C virus (Urabe, et al. (1997) Gene 200: 157–62), coronavirus (Lie et al. (1991) Virology 184: 531–44), and other virus families such as flaviruses and DNA viruses (i.e. Karposi's Sarcoma-associated virus).

In the case of the use of an IRES sequence, the cDNA portion of the construct is preferably upstream of the IRES, as it is well documented that the ratio of expression product upstream:downstream can reach levels as high a 10:1. By using this orientation, more of the expression product is made. The orientation matters less in the case where a 2a sequence is used.

Additionally, preferred embodiments of IRES sequences are non-viral IRES elements found in a variety of organisms including yeast, *Drosophila*, birds and mammals. Like the viral IRES sequences, cellular IRES sequences are heterogeneous in sequence and secondary structure. Cellular IRES sequences, however, may comprise much shorter sequences (Oh et al. (1992) Genes Dev. 6: 1643–53; Chappell et al. (2000) 97: 1536–41). Specific IRES sequences include, but are not limited to, immunoglobulin heavy chain binding protein, transcription factors, protein kinases, protein phosphatases, elF4G (Johannes et al. 1999; Johannes et al. 1998), vacular endothelial growth factor (Huez, et al. (1989) Mol. Cell. Biol. 18: 6178–90), c-myc (Stoneley et al. (2000) Nucleic Acids Res. 28: 87–94), pro-apoptotic protein Apaf-1 (Coldwell et al. (2000) Oncogene, 19: 899–905), DAP-5 (Henis-Korenblit et al.(2000) Molecular Cell Bio. 20: 496–506), connexin (Werner, R. (2000) IUBMB Life, 50: 173–176), Notch 2 (Lauring et al. (2000) Mol Cell. 6: 939–45), and fibroblast growth factor (Creancier, et al. (2000) J. Cell. Biol. 150: 275–281). As some IRES sequences act or function efficiently in particular cell types, the person skilled in the art will choose IRES elements with relevance to particular cells that will be expressing the retroviral cDNA expression vector. Moreover, multiple IRES sequences in various combinations, either homomultimeric or heteromultimeric, as direct tandem repeats or with linkers, are useful for increasing efficiency of translation initiation of cDNA and fusion partner. The combinations of IRES elements comprise at least 2 to 10 or more copies or combinations of IRES sequences, depending on the efficiency of initiation desired.

The present invention further contemplates use of enhancers of IRES mediated initiation sequences. IRES initiated translation may be enhanced by any number of methods. Cellular expression of virally encoded protease, which cleaves elF4F to dissociate CAP-binding activity of the elF4F complex from the 40S ribosome complexes, may be employed to increase preference for IRES translation initiation events. These proteases are found in certain Picornaviruses and can be expressed in a cell by introducing the viral protease gene by transfection of nucleic acids encoding the protease or introduction into the cell through retroviral delivery. Other enhancers of IRES elements that may be used with the present embodiment include cis acting elements, such as 3' untranslated region of hepatitis C virus (Ito et al. (1998) J. Virol. 72: 8789–8786) and polyA segments (Bergamini, et al. (2000) RNA 6: 1781–1790). In addition, preferential use of cellular IRES sequences may occur when CAP dependent mechanisms are impaired, for example by dephosphorylation of 4E-BP, proteolytic cleavage of elF4G, or especially when cells are placed under stress such g-irradiation, amino acid starvation, or hypoxia. Thus In addition to the methods described above, activation or introduction of phosphatases acting on 4E-BP, proteases of elF4G, or treatment to induce stress in the cell are all included in the enhancing methods. Other enhancers are trans-acting IRES factors, which include, but not limited to, heterogeneous nuclear ribonucleoprotein (hnRNP) (Kaminski et al. (1998) RNA 4: 626–638), PTB hnRNP E2/PCBP2 (Walter et al. (1999) RNA 5: 1570–1585), La autoantigen (Meerovitch et al (1993) J. Virol. 67: 3798–3807), unr (Hunt et al. (1999) Genes Dev. 13: 437–448), ITAF45/Mpp1 (Pilipenko et al (2000) Genes Dev. 14: 2028–2045), DAP5/NAT1/p97 (He- nis-Korenblit et al (2000) Mol. Cell. Biol. 20: 496–506), and nucleolin (Izumi et al. (2001) Virus Res. 76: 17–29). These factors may be introduced into a cell either alone or in combination to increase efficiency of translation initiation from particular IRES elements. Accordingly, various combinations of IRES elements and enhancing factors are used to effect a separation reaction.

In a preferred embodiment, the linker connecting the first and second nucleic acids comprises a cleavage site. Such a linker may fuse the first nucleic acid to the 5' end or the 3' end of the second nucleic acid. The expression products of such a vector include a fusion nucleic acid, and a fusion protein wherein the cDNA-encoded polypeptide moiety and the detectable protein moiety encoded by the second nucleic acid are separated by an intervening cleavage site which is a polypeptide sequence that is recognized by a protease. This site provides for cleavage of the covalent peptide linkage which links the cDNA-encoded polypeptide moiety to the detectable protein moiety in the fusion protein and for covalent separation of the two polypeptides unless otherwise covalently linked (e.g. by cysteine bridge).

Many protease recognition sites are known in the art and may be used as cleavage sites in the present invention. For example see *Current Protocols in Protein Science*, John Wiley & Sons, Coligan et. al. eds., updated December 2001, Chapter 21, *Peptidases*, expressly incorporated herein by reference.

Preferred protease cleavage sites include, but are not limited to prosequences of retroviral proteases including human immunodeficiency virus protease and sequences recognized and cleaved by trypsin (EP 578472; Takasuga et al. (1992) J. Biochem. 112: 652), proteases encoded by Picornaviruses (Ryan, et al. (1997) J. Gen. Virol. 78: 699–723), factor $X_a$ (Gardella et al. (1990) J. Biol. Chem. 265:15854; WO 9006370), collagenase (J03280893; WO 9006370; Tajima et al. (1991) J. Ferment. Bioeng. 72:362), clostripain (EP 578472), subtilisin (including mutant H64A subtilisin, Forsberg et al. (1991) J. Protein Chem. 10: 517), chymosin, yeast KEX2 protease (Bourbonnais et al. (1988) J. Bio. Chem. 263:15342, thrombin (Forsberg et al., supra; Abath et al. (1991) BioTechniques 10:178), *Staphylococcus aureus* V8 protease or similar endoproteinase-Glu-C to cleave after Glu residues (EP 578472; Ishizaki et al. (1992) Appl. Microbiol. Biotechnol. 36:483), cleavage by NIa proteainase of tobacco etch virus (Parks et al. (1994) Anal. Biochem. 216: 413), endoproteinase-Lys-C (U.S. Pat. No. 4,414,332) and endoproteinase-AspN, *Neisseria* type 2 IgA protease (Pohlner et al. (1992) Bio/Technology 10:799–804), soluble yeast endoproteinase yscF (EP 467839), chymotrypsin (Altman et al. (1991) Protein Eng. 4:593), enteropeptidase (WO 9006370), and lysostaphin, a polyglycine specific endoproteinase (EP 316748).

In a preferred embodiment, the linker is a type 2a sequence.

By type 2A sequences herein is meant sequences that when translated inhibit formation of peptide linkages during the translation process. Type 2A sequences are distinguished from IRES sequences in that 2A sequences do not involve CAP independent translation initiation. Although the mechanism of action is unclear, type 2A sequences appear to act by disrupting peptide bond formation between the nascent polypeptide chain and the incoming activated $tRNA^{PRO}$ (Donnelly et al., J. of Virology (2001) 82, 1013–1025). An advantage of type 2A separation sequences is that near stoichiometric amounts of cDNA encoded peptide and detectable protein are made as compared to IRES sequences, and Type 2A sequences do not require additional factors as compared to protease recognition sites.

The type 2a sequence of the Foot and Mouth Disease virus is especially preferred (Ryan et. al., EMBO J., 13: 928–933, 1994).

In a preferred embodiment, the retroviral cDNA fragment expression vectors are self-inactivating (SIN) vectors, as discussed above. Self-inactivating vectors which contain a deletion in the enhancer and promoter sequences of the 3' LTR and transfer this sequence to the 5' LTR are known (Yu et. al., PNAS 83:3194–3198, 1986, expressly incorporated herein by reference.

In a preferred embodiment, the retroviral cDNA expression vectors comprise a fusion partner as generally described for cDNA expression vectors above, in addition to the second nucleic acid encoding a detectable protein.

In one aspect of the invention, methods for screening for a bioactive agent capable of altering the phenotype of a cell in a desirable way are provided. Importantly, the methods have the advantage of being function-based screening methods. Accordingly, no knowledge of the mechanism by which a bioactive agent works to effect a change in phenotype is required; bioactive agents are selected based on their ability to alter a cell in an observable way. Further, while a bioactive agent may modulate a signal transduction pathway to effect a change in phenotype, no knowledge of the signaling pathway or targets therein with which the bioactive agent interacts is required. Thus, the disclosed methods are an in vivo stratagem for accessing intracellular signaling mechanisms and altering cell phenotype and do not require prior knowledge of signaling pathways or their relationship to phenotype. The invention does, however, provide tools to characterize signaling pathways and identify target molecules therein that modulate cell phenotype. These target molecules may serve as lead compounds for pharmaceutical development, and may be used to characterize signaling pathways and provide additional lead compounds.

The present methods provide a significant improvement over conventional screening techniques, as they allow the rapid screening of large numbers of oligonucleotides and their corresponding expression products in a single, in vivo step. Thus, by delivering nucleic acids to cells and then screening cells, without having to collect or synthesize candidate agents in vitro, highly efficient screening is accomplished. In addition, the present methods allow screening in the absence of significant prior characterization of the cellular defect per se.

The present methods of using cDNA libraries disclosed herein have an additional advantage over prior screening methods. The present cDNA libraries provide for the expression of products that are directed at naturally occurring mRNAs and proteins. Particularly, the present expression vector libraries are produced using physiological sources of mRNA and consequently are, in part, directed to the inhibition of mRNA and mRNA expression products. In a preferred embodiment, the present retroviral libraries comprise vectors which may be used to express antisense nucleic adds and dominant negative polypeptides for inhibiting the activity of host cell mRNAs and polypeptide products thereof.

In one aspect of the invention, methods of screening for a bioactive agent capable of altering the phenotype of a cell in a desirable way are provided. In one embodiment, the method comprises the steps of a) introducing a retroviral cDNA expression vector library into a plurality of cells; b) screening the plurality of cells for a cell exhibiting a phenotype which is altered in a desirable way, wherein the altered phenotype is due to the expression of a cDNA. The method may also comprise any of the steps of c) isolating at least one cell exhibiting an altered phenotype; d) isolating a nucleic acid comprising the cDNA from the cell exhibiting an altered phenotype; e) identifying the bioactive agent; and f) identifying and/or isolating the molecule(s) to which the agent binds. Additionally, in some preferred embodiments, the methods involve stimulating the plurality of cells in manner known to produce a disease-like behavioral response or a phenotype of the disease process.

In a further embodiment, the method comprises the steps of a) introducing a retroviral cDNA expression vector library into a first plurality of cells; b) contacting the first plurality of cells with a second plurality of cells; and c) screening the second plurality of cells for a cell exhibiting a phenotype which is altered in a desirable way, wherein the altered phenotype is due to contact with the first plurality of cells and expression of cDNA in the first plurality of cells. The method may also comprise any of the steps of d) isolating a cell from the first plurality of cells which is contacted with at least one cell in the second plurality of cells exhibiting an altered phenotype; e) isolating a nucleic acid comprising the cDNA from the cell isolated from the first plurality of cells; f) identifying the bioactive agent; and g) identifying and/or isolating the molecule(s) to which the agent binds.

A general description of the techniques used for these methods and examples demonstrating the use thereof are found in U.S. Pat. No. 6,153,380 issued to Nolan et. al. Nov. 28, 2000, expressly incorporated herein by reference. See also Lorens et al., Curr. Opin. Biotechnol., 12:613–621, 2001; Lorens et al., Nat Genet., 27: 23–29, 2001, each of which is expressly incorporated herein by reference.

By "candidate bioactive agents" or "candidate drugs" or "candidate expression products" or grammatical equivalents herein is meant the cDNA expression vector of the present invention, or the expression products thereof, particularly the cDNA-encoded nucleic acid and peptide expression products. Candidate bioactive agents may be translation products of the cDNA expression vectors, i.e. peptides, or transcription products of the vectors, i.e. either DNA or RNA.

Candidate nucleic acids may be tested for the ability to modulate the phenotype of a cell.

By nucleic acid or "oligonucleotide" or grammatical equivalents herein is meant at least two nucleotides covalently linked together. A nucleic acid of the present invention will generally contain phosphodiester bonds, although in some cases, as outlined below, nucleic acid analogs are included that may have alternate backbones, comprising, for example, phosphoraride (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Adds Res. 19:1437 (1991); and U.S. Pat. No. 5,644,048), phosphorodithioate (Briu et al., J. Am. Chem. Soc. 111:2321 (1989), O-methylphophoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meier et al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169–176). Several nucleic acid analogs are described in Rawls, C & E News Jun. 2, 1997 page 35. All of these references are hereby expressly incorporated by reference. These modifications of the ribosephosphate backbone may be done to increase the stability and half-life of such molecules in physiological environments.

The nucleic adds may be single stranded or double stranded, as specified, or contain portions of both double stranded or single stranded sequence. The nucleic acid may be DNA, both genomic and cDNA, RNA or hybrid, where the nucleic acid contains any combination of deoxyribo- and ribonucleotides, and any combination of bases, including uracil, adenine, thymine, cytosine, guanine, xanthanine hypoxanthanine, isocytosine, isoguanine, etc., although generally occurring bases are preferred. As used herein, the term "nucleoside includes nucleotides as well as nucleoside and nucleotide analogs, and modified nucleosides such as amino modified nucleosides. In addition, "nucleoside" includes non-naturally occurring analog structures. Thus for example the individual units of a peptide nucleic add, each containing a base, are referred herein as a nucleotide.

In a preferred embodiment, the candidate bioactive agents are translation products of cDNA expression vectors. In this embodiment, the cDNA expression vectors are introduced into cells and used to express peptides. Thus, in this embodiment, the candidate bioactive agents are peptides.

By "peptide", "polypeptide", "oligopeptide" or "protein" herein is meant at least two covalently attached amino acids. In a preferred embodiment, a protein is made up of naturally occurring amino adds and peptide bonds, such as proteins synthesized by the cellular translation system. However, as used below, a protein may also be made up of synthetic peptidomimetic structures. Thus "amino acid" or "peptide residue" as used herein means both naturally occurring and synthetic amino adds. For example, homo-phenylalanine, citrulline, and norleucine are considered amino acids for the purposes of the invention. "Amino acids" also includes imino residues such as proline and hydroxyproline. The side chains may be either the (R) or (S) configuration. In the preferred embodiment, the amino acids are in the (S) or L configuration. If non-naturally occurring side chains are used, non-amino acid substituents may be used, for example to prevent or retard in-vivo degradations. Proteins including non-naturally occurring amino acids may be synthesized or in some cases, made by recombinant techniques (see van Hest et al. (1998) FEBS Left. 428:68–70 and Tang et al. (1999) Abstr. Pap. Am. Chem. S218: U138-U138 Part 2, both of which are expressly incorporated by reference herein).

The candidate peptides comprise a cDNA-encoded peptide moiety. In one embodiment, the candidate peptides additionally comprise a detectable protein moiety and are fusion proteins. In a preferred embodiment, the detectable protein moiety is an autofluorescent protein. In a further preferred embodiment, the autofluorescent protein is GFP, preferably GFP from *Aequeora, Renilla*, or *Ptilosarcus* species, as described herein.

It will be appreciated that a plurality of expression vectors may be used to express a plurality of fusion proteins having different cDNA-encoded moieties and the same detectable protein moiety. It is understood that differences in the activities of candidate agents are due to differences in the cDNA-encoded expression products. Accordingly, the cDNA and expression products thereof are sometimes referred to herein as candidate bioactive agents.

In a preferred embodiment, candidate bioactive agents are translation products of retroviral cDNA expression vectors.

In a preferred embodiment, candidate nucleic acids are introduced into host cells in the form of RNA genomes of retroviruses by transduction with retroviral particles.

In a preferred embodiment, the candidate bioactive agents are transcription products of the cDNA expression vectors, and are thus also nucleic acids. The candidate agents comprise a cDNA-encoded nucleic acid. The cDNA nucleic acid may be in sense or antisense orientation which is predetermined by the directional cloning strategy described herein. In one embodiment, the candidate agents additionally comprise a nucleic acid encoding a detectable protein and are fusion nucleic adds. In a preferred embodiment, the detectable protein moiety is an autofluorescent protein. In a further preferred embodiment, the autofluorescent protein is GFP, preferably GFP from *Aequeora, Renilla*, or *Ptilosarcus* species, as described herein.

In a preferred embodiment, the candidate bioactive agents are transcription products of retroviral cDNA expression vectors. The transcription products may be either primary transcripts or secondary transcription products. That is, using the retroviral reverse transcriptase, primary DNA is made which is later converted into double stranded DNA. Additionally, using the primary DNA, RNA transcripts can be generated within the cell, including mRNA and antisense RNA.

In a preferred embodiment, the cDNA is linked to the 5' end of a fusion partner, which is a detectable protein, as described herein.

In an especially preferred embodiment, the fusion partner is a detectable protein selected from the group consisting of GFPs from *Aequeora, Renilla*, or *Ptilosarcus* species, as described herein, and the linkage comprises an IRES separation sequence.

In another embodiment, the cDNA is fused to a fusion partner as described herein.

In one embodiment, the fusion partner is a rescue tag, as described herein, and is preferably fused to the cDNA fragment encoded polypeptide moiety.

As discussed above, the cDNA may be 5', 3', or situated within an internal position of the fusion partner, with the appropriate location depending on the particular fusion partner, as is known in the art.

In the screening methods provided herein, generally, cDNA expression vectors are expressed within host cells to produce candidate bioactive agents. As outlined above, the candidate agents include translation products, i.e. peptides, and transcription products, i.e. nucleic acids. The cDNA expression vectors are introduced into cells to screen for bioactive agents capable of altering the phenotype of a cell in a desirable way.

By "introduced into" or grammatical equivalents herein is meant that the nucleic acids enter the cells in a manner suitable for subsequent expression of the nucleic acid. The preferred method of the present invention is transduction by retroviral particle, although other methods may be used.

Thus, in a preferred embodiment, retroviral cDNA expression vectors are used to produce retroviral particles in appropriate retroviral packaging cells as described herein. In this embodiment, a retroviral cDNA expression vector is packaged in the form of a retroviral genome which may then be introduced to a host cell for expression of candidate agents including nucleic acids and polypeptides.

However, it will be recognized by those in the art that other methods of nucleic acid introduction, such as $CaPO_4$ precipitation, liposome fusion, lipofectin®, and electroporation, may be used. The candidate nucleic acids may stably integrate into the genome of the host cell (for example, with retroviral introduction, outlined below), or may exist either transiently or stably in the cytoplasm (i.e. through the use of traditional plasmids, utilizing standard regulatory sequences, selection markers, etc.). As many pharmaceutically important screens require human or model mammalian cell targets, retroviral vectors capable of transfecting (or transducing) such targets are preferred.

In a preferred embodiment, the candidate nucleic acids are part of a retroviral particle which infects the cells. Generally, infection of the cells is straightforward with the application of the infection-enhancing reagent polybrene, which is a polycation that facilitates viral binding to the target cell. Infection can be optimized such that each cell generally expresses a single construct, using the ratio of virus particles to number of cells. Infection follows a Poisson distribution.

In a preferred embodiment, the candidate nucleic acids are introduced into the cells using retroviral vectors. Currently, the most efficient gene transfer methodologies harness the capacity of engineered viruses, such as retroviruses, to bypass natural cellular barriers to exogenous nucleic acid uptake.

The candidate nucleic acids, as part of the retroviral construct, are introduced into the cells to screen for bioactive agents capable of altering the phenotype of a cell.

As will be appreciated by those in the art, the type of cells used in the present invention can vary widely. Basically, any mammalian cells may be used, with mouse, rat, primate and human cells being particularly preferred, although as will be appreciated by those in the art, modifications of the system by pseudotyping allows all eukaryotic cells to be used, preferably higher eukaryotes. As is more fully described below, a screen will be set up such that the cells exhibit a selectable phenotype in the presence of a bioactive agent. As is more fully described below, cell types implicated in a wide variety of disease conditions are particularly useful, so long as a suitable screen may be designed to allow the selection of cells that exhibit an altered phenotype as a consequence of the presence of a bioactive agent within the cell.

Accordingly, suitable cell types include, but are not limited to, tumor cells of all types (particularly melanoma, myeloid leukemia, carcinomas of the lung, breast, ovaries, colon, kidney, prostate, pancreas and testes), cardiomyocytes, endothelial cells, epithelial cells, lymphocytes (T-cell and B cell) mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Suitable cells also include known research cells, including, but not limited to, Jurkat T cells, NIH3T3 cells, CHO, Cos, HeLa, NIH 3T3 etc. See the ATCC cell line catalog, hereby expressly incorporated by reference. Also included are cells from the following tissue types: adipose, adrenal, adult brain, adult liver, adult ovary, amygdala, aorta, bladder, blood, bone marrow, brain tumor, breast, breast tumor, capillary endothelial cells, carcinoma, cerebellum, cervix, chondrocyte, colon, colon tumor, colorectal adenocarcinoma, embryo, embryonic brain, embryonic adrenal, embryonic eye, embryonic gut, embryonic liver, embryonic lung, embryonic muscle, embryonic spleen, endothelial, epidermis, epithelial cell, erythroleukemia, esophageal tumor, esophagus, eye, fetus, fetal brain, fetal adrenal, fetal eye, fetal gut, fetal liver, fetal lung, fetal muscle, fetal spleen, fibroblast, fibrosarcoma, glioblastoma, glioma, heart, adult heart, hepatocarcinoma, hepatoma, hippocampus, hypothalamus, intestine, small intestine, keratinocyte, kidney, kidney tumor, liver, liver tumor, lung, lung tumor, lymph node, lymphocyte, lymphoblast, lymphoma, macrophage, microglia, mammary gland, mucus-producing gland, muscle, myoblast, monocyte, nasal mucosa, neuronal, stomach, thyroid, uterus, oocyte, pancreas, ovarian tumor, pituitary, prostate, rectal tumor, rectum, retina, salivary gland, spinal cord, spleen, submucosa, stem cell, and tonsil.

In one embodiment, the cells may be genetically engineered, that is, contain exogenous nucleic acid, for example, to contain target molecules that are exogenous.

In a preferred embodiment, a first plurality of cells is screened. That is, the cells into which the candidate nucleic acids are introduced are screened for an altered phenotype. Thus, in this embodiment, the effect of the bioactive agent is seen in the same cells in which it is made; i.e. an autocrine effect.

By a "plurality of cells" herein is meant roughly from about $10^3$ cells to $10^8$ or $10^9$, with from $10^6$ to $10^8$ being preferred. This plurality of cells comprises a cellular library, wherein generally each cell within the library contains a member of the retroviral molecular library, i.e. a different candidate nucleic acid, although as will be appreciated by those in the art, some cells within the library may not contain a retrovirus, and some may contain more than one. When methods other than retroviral infection are used to introduce the candidate nucleic adds into a plurality of cells, the distribution of candidate nucleic adds within the individual cell members of the cellular library may vary widely, as it is generally difficult to control the number of nucleic acids which enter a cell during electroporation, etc.

In a preferred embodiment, the candidate nucleic acids are introduced into a first plurality of cells, and the effect of the candidate bioactive agents is screened in a second or third plurality of cells, different from the first plurality of cells, i.e. generally a different cell type. That is, the effect of the bioactive agents is due to an extracellular effect on a second cell; i.e. an endocrine or paracrine effect. This is done using standard techniques. The first plurality of cells may be grown in or on one media, and the media is allowed to touch a second plurality of cells, and the effect measured. Alternatively, there may be direct contact between the cells. Thus, "contacting" is functional contact, and includes both direct and indirect. In this embodiment, the first plurality of cells may or may not be screened.

If necessary, the cells are treated to conditions suitable for the expression of the candidate nucleic acids (for example, when inducible promoters are used), to produce the candidate expression products, either translation or transcription products.

Thus, the methods of the present invention comprise introducing a molecular library of candidate nucleic acids into a plurality of cells to form a cellular library comprising candidate nucleic acids. Each of the nucleic acids comprises a cDNA. The plurality of cells is then screened, as is more fully outlined below, for a cell exhibiting an altered phenotype. The altered phenotype is due to the presence of a bioactive agent.

By "altered phenotype" or "changed physiology" or other grammatical equivalents herein is meant that the phenotype of the cell is altered in some way, preferably in some detectable and/or measurable way. As will be appreciated in the art, a strength of the present invention is the wide variety of cell types and potential phenotypic changes which may be tested using the present methods. Accordingly, any phenotypic change which may be observed, detected, or measured may be the basis of the screening methods herein. Suitable phenotypic changes include, but are not limited to: gross physical changes such as changes in cell morphology, cell growth, cell viability, adhesion to substrates or other cells, and cellular density; changes in the expression of one or more RNAs, proteins, lipids, hormones, cytokines, or other molecules; changes in the equilibrium state (i.e. half-life) or one or more RNAs, proteins, lipids, hormones, cytokines, or other molecules; changes in the localization of one or more RNAs, proteins, lipids, hormones, cytokines, or other molecules; changes in the bioactivity or specific activity of one or more RNAs, proteins, lipids, hormones, cytokines, receptors, or other molecules; changes in the secretion of ions, cytokines, hormones, growth factors, or other molecules; alterations in cellular membrane potentials, polarization, integrity or transport; changes in infectivity, susceptability, latency, adhesion, and uptake of viruses and bacterial pathogens; etc. By "capable of altering the phenotype" herein is meant that the bioactive agent can change the phenotype of the cell in some detectable and/or measurable way.

The altered phenotype may be detected in a wide variety of ways, as is described more fully below, and will generally depend and correspond to the phenotype that is being changed. Generally, the changed phenotype is detected using, for example: microscopic analysis of cell morphology; standard cell viability assays, including both increased cell death and increased cell viability, for example, cells that are now resistant to cell death via virus, bacteria, or bacterial or synthetic toxins; standard labeling assays such as fluorometric indicator assays for the presence or level of a particular cell or molecule, including FACS or other dye staining techniques; biochemical detection of the expression of target compounds after killing the cells; etc. In some cases, as is more fully described herein, the altered phenotype is detected in the cell in which the cDNA expression vector was introduced; in other embodiments, the altered phenotype is detected in a second cell which is responding to some molecular signal from the first cell as a consequence of candidate agent expression in the first cell.

In a preferred embodiment, once a cell with an altered phenotype is detected, the cell is isolated from the plurality which do not have altered phenotypes. This may be done in any number of ways, as is known in the art, and will in some instances depend on the assay or screen. Suitable isolation techniques include, but are not limited to, FACS, lysis selection using complement, cell cloning, scanning by Fluorimager, expression of a "survival" protein, induced expression of a cell surface protein or other molecule that can be rendered fluorescent or taggable for physical isolation; expression of an enzyme that changes a non-fluorescent molecule to a fluorescent one; overgrowth against a background of no or slow growth; death of cells and isolation of DNA or other cell vitality indicator dyes, etc.

In a preferred embodiment, the candidate nucleic acid and/or the bioactive agent is isolated from the positive cell. This may be done in a number of ways. In a preferred embodiment, primers complementary to DNA regions common to the retroviral constructs, or to specific components of the library such as a rescue sequence, defined above, are used to "rescue" the candidate nucleic acid. Alternatively, the bioactive agent is isolated using a rescue sequence. Thus, for example, rescue sequences comprising epitope tags or purification sequences may be used to pull out the bioactive agent, using immunoprecipitation or affinity columns. In some instances, as is outlined below, this may also pull out the primary target molecule, if there is a sufficiently strong binding interaction between the bioactive agent and the target molecule. Alternatively, the peptide may be detected using mass spectroscopy.

Once rescued, the sequence of the bioactive agent and/or bioactive nucleic acid is determined. This information can then be used in a number of ways.

In a preferred embodiment, the bioactive agent is resynthesized and reintroduced into the target cells, to verify the effect. This may be done using retroviruses, or alternatively using fusions to the HIV-1 Tat protein, and analogs and related proteins, which allows very high uptake into target cells. See for example, Fawell et al., PNAS USA 91:664 (1994); Frankel et al., Cell 55:1189 (1988); Savion et al., J. Biol. Chem. 256:1149 (1981); Derossi et al., J. Biol. Chem. 269:10444 (1994); and Baldin et al., EMBO J. 9:1511 (1990), all of which are incorporated by reference.

In a preferred embodiment, the sequence of a bioactive agent is used to generate more candidate bioactive agents. For example, the sequence of the bioactive agent may be used to develop bioactive agents with increased or altered activities through mutation. Alternatively, bioactive agents with different affinity may be sought through mutation. Furthermore, it may be desirable to put the identified cDNA-fragment expression product into other presentation structures, or to alter the sequence of the constant region of the presentation structure, to alter the conformation/shape of the bioactive agent. It may also be desirable to "walk" around a potential binding site, in a manner similar to the mutagenesis of a binding pocket, by keeping one end of the ligand region constant and randomizing the other end to shift the binding of the peptide around.

In a preferred embodiment, either the bioactive agent or the bioactive nucleic acid encoding it is used to identify target molecules. Bioactive agents interact with target molecules to modulate or alter cell phenotype. As will be appreciated by those in the art, there may be primary target molecules, to which the bioactive agent binds or acts upon directly, and secondary target molecules, which are part of the signalling pathway affected by the bioactive agent; these might be termed "validated targets".

In a preferred embodiment, the bioactive agent is used to pull out target molecules. For example, as outlined herein, if the target molecules are proteins, the use of epitope tags or purification sequences can allow the purification of primary target molecules via biochemical means (co-immunoprecipitation, affinity columns, etc.). Alternatively, the peptide, when expressed in bacteria and purified, can be used as a probe against a bacterial cDNA expression library made from mRNA of the target cell type. Or, peptides can be used as "bait" in either yeast or mammalian two or three hybrid systems. Such interaction cloning approaches have been very useful to isolate DNA-binding proteins and other interacting protein components. The peptide(s) can be combined with other pharmacologic activators to study the epistatic relationships of signal transduction pathways in question. It is also possible to synthetically prepare labeled peptide bioactive agent and use it to screen a cDNA library expressed in bacteriophage for those cDNAs which bind the peptide. Furthermore, it is also possible that one could use cDNA cloning via retroviral libraries to "complement" the effect induced by the peptide. In such a strategy, the peptide would be required to be stochiometrically titrating away some important factor for a specific signaling pathway. If this molecule or activity is replenished by over-expression of a cDNA from within a cDNA library, then one can clone the target. Similarly, cDNAs cloned by any of the above yeast or bacteriophage systems can be reintroduced to mammalian cells in this manner to confirm that they act to complement function in the system the peptide acts upon.

Once primary target molecules have been identified, secondary target molecules may be identified in the same manner, using the primary target as the "bait". In this manner, signalling pathways may be elucidated. Similarly, bioactive agents specific for secondary target molecules may also be discovered, to allow a number of bioactive agents to act on a single pathway, for example for combination therapies.

The screening methods of the present invention may be useful to screen a large number of cell types under a wide variety of conditions. Generally, the host cells are cells that are involved in disease states, and they are tested or screened under conditions that normally result in undesirable consequences on the cells. When a suitable bioactive agent is found, the undesirable effect may be reduced or eliminated. Alternatively, normally desirable consequences may be reduced or eliminated, with an eye towards elucidating the cellular mechanisms associated with the disease state or signalling pathway.

In preferred embodiments, methods of screening for bioactive agents capable of modulating the following physiological processes or biochemical activities are provided: IgE production in B cells; mast cell activation by IgE binding; mast cell degranulation; B cell activation and antibody secretion in response to antigen receptor simulation; T cell activation in response to antigen receptor stimulation; epithelial cell activation; E3 ubiquitin ligase activity; inflammation induced by E3 ubiquitin ligase activity; inflammation induced by TNF activity; apoptosis in activated T cells; angiogenesis; uncontrolled cell proliferation; uncontrolled cell proliferation mediated by E3 ubiquitin ligase activity; and translation of Hepatitis C-encoded proteins. Methods for measuring these activities and processes are found in U.S. patent application Ser. Nos. 10/039,761; 09/062,330; 09/293,670; 09/826,312; 09/050,861; 09/425,324; 09/076,624, each incorporated herein in their entirety by reference; and U.S. Provisional Patent Application Ser. No. 60/316,723, incorporated herein in its entirety by reference.

In one embodiment, the present invention is useful in identifying modulators of the immune response. For example, activation of B-cells initiates various facets of humoral immunity, including immunoglobulin synthesis and antigen presentation by B-cells. Activation is mediated by engagement of the B-cell receptor (BCR), for example by binding of anti-IgM F(ab') fragments, which induces several signal transduction pathways leading to various responses by the B-cell, including immunoglobulin synthesis and secretion, apoptosis, expression of cell surface marker CD69, and modulation of IgH promoter activity. cDNA expression vector are introduced into appropriate B-cell lines, such as Ramos Human B-cell lines, M12.4 etc., to identify various effectors of the signaling pathways activated by B-cell receptor engagement. The assays may comprise determining the level of CD69 cell surface marker (i.e. by fluorescently labeled anti-CD69 antibody and FACS selection of cells expressing high levels of CD69) following receptor activation.

In a preferred embodiment, the present methods and compositions are useful for screening for agents capable of modulating exocytosis. By "alteration" or "modulation" in relation to exocytosis is meant a decrease or increase in amount or frequency of exocytosis in one cell compared to another cell or in the same cell under different conditions. Often mediated by specialized cells, exocytosis is vital for a variety of cellular processes, including neurotramitter release by neurons, hormone release by adrenal chromaffin cells (adrenaline) and pancreatic β-cells (insulin), and histamine release by mast cells.

Disorders involving exocytosis are numerous. For example, inflammatory immune response mediated by mast cells leads to a variety of disorders, including asthma and allergies. Therapy for allergy remains limited to blocking mediators released by mast cells (i.e. anti-histamines) and non-specific anti-inflammatory agents, such as steroids and mast cell stabilizers. These treatments are only marginally effective in alleviating the symptoms of allergy. To identify cellular targets for drug design or candidate effectors of exocytosis, cDNA expression vectors may be introduced into appropriate cells, for example mast cells, and selected for modulation of exocytosis by assaying for changes in cellular exocytosis properties. These cells are stimulated with appropriate inducer if exocytosis is triggered by an inducing signal.

Assays for changes in exocytosis may comprise sorting cells in a fluorescence cell sorter (FACS) by measuring alterations of various exocytosis indicators, such as light scattering, fluorescent dye uptake, fluorescent dye release, granule release, and quantity of granule specific proteins (as provided in U.S. Ser. No. 09/293,670, incorporated herein by reference). Use of combinations of indicators reduces background and increases specificity of the sorting assay.

The exocytosis assay based on changes in the cell's light scattering properties, including use of forward and side scatter properties of the cells, are indicative of the size, shape, and granule content of the cell. Multiparameter FACS selection based on light scattering properties of cells are well known in the art, (see Perretti, M. et al. (1990) J. Pharmacol. Methods 23: 187–94; Hide, I. et al. (1993) J. Cell Biol. 123: 585–93).

Assays based on uptake of fluorescent dyes reflect the coupling of exocytosis and endocytosis in which endocytosis levels indirectly reflect exocytosis levels since the cell attempts to maintain cell volume and membrane integrity as the amount of cell membrane rapidly changes when secretory vesicles fuse with the cell membrane. Preferred fluorescent dyes include styryl dyes, such as FM1-43, FM4-64, FM14-68, FM2-10, FM4-84, FM1-84, FM14-27, FM14-29, FM3-25, FM3-14, FM5-55, RH414, FM6-55, FM10-75, FM1-81, FM9-49, FM4-95, FM4-59, FM9-40, and combinations thereof. Styryl dyes such as FM1-43 are only weakly fluorescent in water but very fluorescent when associated with a membrane, such that dye uptake by endocytosis is readily discernable (Betz, et al. (1996) Current Opinion in Neurobiology, 6:365–371; Molecular Probes, Inc., Eugene, Oreg., "Handbook of Fluorescent Probes and Research Chemicals", 6th Edition, 1996, particularly, Chapter 17, and more particularly, Section 2 of Chapter 17, (including referenced related chapter), hereby incorporated herein by reference). Useful solution dye concentration is about 25 to 1000–5000 nM, with from about 50 to about 1000 nM being preferred, and from about 50 to 250 being particularly preferred.

Exocytosis assays based on fluorescent dye release rely on release of dye that is taken up passively by the cell or dye that is actively endocytosed by the cell. Release of dyes initially taken up by a cell results in decreased cellular fluorescence and presence of the dye in the cellular medium, thus providing two ways to measure dye release. For example, styryl dyes taken up into cells by endocytosis is released into the cellular media by exocytosis, resulting in decreased cellular fluorescence and presence of the dye in the medium. Another dye release assay uses low pH dyes, such as acridine orange, LYSOTRACKER™ red, LYSOTRACKER™ green, and LYSOTRACKER™ blue (Molecular Probes, supra), which stains exocytic granules when dye is internalized by the cell.

Preferential staining of exocytic granules when the vesicles fuse with the cell membrane provides an additional assay for measuring exocytosis. Annexin V, which binds to phospholipid (phospahtidyl serine) in a divalent ion dependent manner, specifically binds to exocytic granules present on the cell surface but fails to bind internally localized exocytic granules. This property of Annexin provides a basis for determining exocytosis by the level of Annexin bound to cells. Cells show an increase in Annexin binding in proportion to the time and intensity of the exocytic response. Annexin is detectable directly by use of fluorescently labeled Annexin derivatives (i.e. FITC, TRITC, AMCA, APC, or Cy-5 fluorescent labels), or indirectly by use of Annexin modified with a primary label (e.g. biotin), which is detected using a labeled secondary agent that binds to the primary label (e.g. fluorescently labeled avidin).

Alternatively, in a preferred embodiment the exocytosis indicators are engineered into the cells. For example, recombinant proteins comprising fusion proteins of a granule specific, or a secreted protein, and a reporter molecule are expressed in a cell by transforming the cells with a fusion nucleic acid encoding a fusion protein comprising a granule specific or secreted protein and a reporter protein. This is generally done as is known in the art, and will depend on the cell type. Generally, for mammalian cells, retroviral vectors are preferred for delivery of the fusion nucleic acid. Preferred reporter molecules include, but are not limited to, *Aequoria victoria* GFP, *Renilla mulleris* GFP, *Renilla reniformis* GFP, *Renilla ptilosarcus*, GFP, BFP, YFP, and enzymes including luciferases (*Renilla*, firefly etc.) and β-galactosidases. Presence of the granule protein-reporter fusion construct on the cell surface or presence of secreted protein-reporter fusion construct in the medium indicates the level of exocytosis in the cells. Thus, in one preferred embodiment cells are transformed with retroviral vectors expressing a fusion protein comprising granule specific (i.e. secretory vesicle) proteins, such as VAMP (synaptobrevin) or synaptotagmin, fused to a GFP reporter molecule. The cells are monitored for localization of the fusion protein to the cell membrane. Candidate agents (cDNA expression vectors) are introduced into these transformed cells and are tested for their ability to affect distribution of the fusion protein. Since the definition of granule specific proteins encompasses mediators released during exocytosis, including, but not limited to, serotonin, histamine, heparin, hormones, etc., these granule proteins may be identified using specific antibodies.

In a preferred embodiment, the present methods are useful in cancer applications. The ability to rapidly and specifically kill tumor cells is a cornerstone of cancer chemotherapy. In general, using the methods of the present invention, cDNA expression libraries can be introduced into any tumor cell (primary or cultured), and bioactive agents identified which by themselves induce apoptosis, cell death, loss of cell division or decreased cell growth. The methods of the present invention can be combined with other cancer therapeutics (e.g. drugs or radiation) to sensitize the cells and thus induce rapid and specific apoptosis, cell death, loss of cell division or decreased cell growth after exposure to a secondary agent. Similarly, the present methods may be used in conjunction with known cancer therapeutics to screen for agonists to make the therapeutic more effective or less toxic. This is particularly preferred when the chemotherapeutic is very expensive to produce such as taxol.

Known oncogenes such as v-Abl, v-Src, v-Ras, and others, induce a transformed phenotype leading to abnormal cell growth when transfected into certain cells. This is also a major problem with micro-metastases. Thus, in a preferred embodiment, non-transformed cells can be transfected with these oncogenes, and then cDNA libraries introduced into these cells, to select for bioactive agents which reverse or correct the transformed state. One of the signal features of oncogene transformation of cells is the loss of contact inhibition and the ability to grow in soft-agar. When transforming viruses are constructed containing v-Abl, v-Src, or v-Ras in IRES-puro retroviral vectors, infected into target 3T3 cells, and subjected to puromycin selection, all of the 3T3 cells hyper-transform and detach from the plate. The cells may be removed by washing with fresh medium. This can serve as the basis of a screen, since cells which express a bioactive agent will remain attached to the plate and form colonies.

Similarly, the growth and/or spread of certain tumor types is enhanced by stimulatory responses from growth factors and cytokines (PDGF, EGF, Heregulin, and others) which bind to receptors on the surfaces of specific tumors. In a preferred embodiment, the methods of the invention are used to inhibit or stop tumor growth and/or spread, by finding bioactive agents capable of blocking the ability of the growth factor or cytokine to stimulate the tumor cell. The methods involve the introduction of cDNA libraries into specific tumor cells with the addition of the growth factor or cytokine, followed by selection of bioactive agents which block the binding, signaling, phenotypic and/or functional responses of these tumor cells to the growth factor or cytokine in question.

Similarly, the spread of cancer cells (invasion and metastasis) is a significant problem limiting the success of cancer therapies. The ability to inhibit the invasion and/or migration of specific tumor cells would be a significant advance in the therapy of cancer. Tumor cells known to have a high metastatic potential (for example, melanoma, lung cell carcinoma, breast and ovarian carcinoma) can have cDNA expression libraries introduced into them, and peptides selected which in a migration or invasion assay, inhibit the migration and/or invasion of specific tumor cells. Particular applications for inhibition of the metastatic phenotype, which could allow a more specific inhibition of metastasis, include the metastasis suppressor gene NM23, which codes for a dinucleoside diphosphate kinase. Thus intracellular peptide activators of this gene could block metastasis, and a screen for its upregulation (by fusing it to a reporter gene) would be of interest. Many oncogenes also enhance metastasis. Peptides which inactivate or counteract mutated RAS oncogenes, v-MOS, v-RAF, A-RAF, v-SRC, v-FES, and v-FMS would also act as anti-metastatics. Peptides which act intracellularly to block the release of combinations of proteases required for invasion, such as the matrix metalloproteases and urokinase, could also be effective antimetastatics.

In a preferred embodiment, the cDNA libraries of the present invention are introduced into tumor cells known to have inactivated tumor suppressor genes, and successful reversal by either reactivation or compensation of the knockout would be screened by restoration of the normal phenotype. A major example is the reversal of p53-inactivating mutations, which are present in 50% or more of all cancers. Since p53's actions are complex and involve its action as a transcription factor, there are probably numerous potential ways a peptide or small molecule derived from a peptide could reverse the mutation. One example would be upregulation of the immediately downstream cyclin-dependent kinase p21CIP1/WAF1. To be useful such reversal would have to work for many of the different known p53 mutations. This is currently being approached by gene therapy; one or more small molecules which do this might be preferable.

Another example involves screening for bioactive agents which restore the constitutive function of the brca-1 or brca-2 genes, and other tumor suppressor genes important in breast cancer such as the adenomatous polyposis *coli* gene (APC) and the homolog of the *Drosophila* discs-large gene (Dlg), which are components of cell-cell junctions. Mutations of brca-1 are important in hereditary ovarian and breast cancers, and screening for bioactive agents cpable of supressing these cancers is an additional application of the present invention.

In a preferred embodiment, the methods of the present invention are used to create novel cell lines from cancers from patients. A retrovirally delivered candidate agents which inhibits the final common pathway of programmed cell death should allow for short- and possibly long-term cell lines to be established. Conditions of in vitro culture and infection of human leukemia cells will be established. There is a real need for methods which allow the maintenance of certain tumor cells in culture long enough to allow for physiological and pharmacological studies. Currently, some human cell lines have been established by the use of transforming agents such as Ebstein-Barr virus that considerably alters the existing physiology of the cell. On occasion, cells will grow on their own in culture but this is a random event. Programmed cell death (apoptosis) occurs via complex signaling pathways within cells that ultimately activate a final common pathway producing characteristic changes in the cell leading to a non-inflammatory destruction of the cell. It is well known that tumor cells have a high apoptotic index, or propensity to enter apoptosis in vivo. When cells are placed in culture, the in vivo stimuli for malignant cell growth are removed and cells readily undergo apoptosis. The objective would be to develop the technology to establish cell lines from any number of primary tumor cells, for example primary human leukemia cells, in a reproducible manner without altering the native configuration of the signaling pathways in these cells. By introducing nucleic acids encoding peptides which inhibit apoptosis, increased cell survival in vitro, and hence the opportunity to study signalling transduction pathways in primary human tumor cells, is accomplished. In addition, these methods may be used for culturing primary cells, i.e. non-tumor cells.

In a preferred embodiment, the present methods are useful in cardiovascular applications. In a preferred embodiment, cardiomyocytes may be screened for the prevention of cell damage or death in the presence of normally injurious conditions, including, but not limited to, the presence of toxic drugs (particularly chemotherapeutic drugs), for example, to prevent heart failure following treatment with adriamycin; anoxia, for example in the setting of coronary artery occlusion; and autoimmune cellular damage by attack from activated lymphoid cells (for example as seen in post viral myocarditis and lupus). Candidate bioactive agents are inserted into cardiomyocytes, the cells are subjected to the insult, and bioactive agents are selected that prevent any or all of: apoptosis; membrane depolarization (i.e. decrease arrythmogenic potential of insult); cell swelling; or leakage of specific intracellular ions, second messengers and activating molecules (for example, arachidonic acid and/or lysophosphatidic acid).

In a preferred embodiment, the present methods are used to screen for diminished arrhythmia potential in cardiomyocytes. The screens comprise the introduction of the candidate nucleic acids encoding candidate bioactive agents, followed by the application of arrythmogenic insults, with screening for bioactive agents that block specific depolarization of cell membrane. This may be detected using patch clamps, or via fluorescence techniques). Similarly, channel activity (for example, potassium and chloride channels) in cardiomyocytes could be regulated using the present methods in order to enhance contractility and prevent or diminish arrhythmias.

In a preferred embodiment, the present methods are used to screen for enhanced contractile properties of cardiomyocytes and diminish heart failure potential. The introduction of the libraries of the invention followed by measuring the rate of change of myosin polymerization/depolymerization using fluorescent techniques can be done. Bioactive agents which increase the rate of change of this phenomenon can result in a greater contractile response of the entire myocardium, similar to the effect seen with digitalis.

In a preferred embodiment, the present methods are useful to identify agents that will regulate the intracellular and sarcolemmal calcium cycling in cardiomyocytes in order to prevent arrhythmias. Bioactive agents are selected that regulate sodium-calcium exchange, sodium proton pump function, and regulation of calcium-ATPase activity.

In a preferred embodiment, the present methods are useful to identify agents that diminish embolic phenomena in arteries and arterioles leading to strokes (and other occlusive events leading to kidney failure and limb ischemia) and angina precipitating a myocardial infarct are selected. For example, bioactive agents which will diminish the adhesion of platelets and leukocytes, and thus diminish the occlusion events. Adhesion in this setting can be inhibited by the libraries of the invention being inserted into endothelial cells (quiescent cells, or activated by cytokines, i.e. IL-1, and growth factors, i.e. PDGF/EGF) and then screening for peptides that either: 1) downregulate adhesion molecule expression on the surface of the endothelial cells (binding assay); 2) block adhesion molecule activation on the surface of these cells (signaling assay); or 3) release in an autocrine manner peptides that block receptor binding to the cognate receptor on the adhering cell.

Embolic phenomena can also be addressed by activating proteolytic enzymes on the cell surfaces of endothelial cells, and thus releasing active enzyme which can digest blood clots. Thus, delivery of the libraries of the invention to endothelial cells is done, followed by standard fluorogenic assays, which will allow monitoring of proteolytic activity on the cell surface towards a known substrate. Bioactive agents can then be selected which activate specific enzymes towards specific substrates.

In a preferred embodiment, arterial inflammation in the setting of vasculitis and post-infarction can be regulated by decreasing the chemotactic responses of leukocytes and mononuclear leukocytes. This can be accomplished by blocking chemotactic receptors and their responding pathways on these cells. Candidate bioactive libraries can be inserted into these cells, and the chemotactic response to diverse chemokines (for example, to the IL-8 family of chemokines, RANTES) inhibited in cell migration assays.

In a preferred embodiment, arterial restenosis following coronary angioplasty can be controlled by regulating the proliferation of vascular intimal cells and capillary and/or arterial endothelial cells. Candidate bioactive agent libraries can be inserted into these cell types and their proliferation in response to specific stimuli monitored. One application may be intracellular peptides which block the expression or function of c-myc and other oncogenes in smooth muscle cells to stop their proliferation. A second application may involve the expression of libraries in vascular smooth muscle cells to selectively induce their apoptosis. Application of small molecules derived from these peptides may require targeted drug delivery; this is available with stents, hydrogel coatings, and infusion-based catheter systems. Peptides which downregulate endothelin-1A receptors or which block the release of the potent vasoconstrictor and vascular smooth muscle cell mitogen endothelin-1 may also be candidates for therapeutics. Peptides can be isolated from these libraries which inhibit growth of these cells, or which prevent the adhesion of other cells in the circulation known to release autocrine growth factors, such as platelets (PDGF) and mononuclear leukocytes.

The control of capillary and blood vessel growth is an important goal in order to promote increased blood flow to ischemic areas (growth), or to cut-off the blood supply (angiogenesis inhibition) of tumors. Candidate bioactive agent libraries can be inserted into capillary endothelial cells and their growth monitored. Stimuli such as low oxygen tension and varying degrees of angiogenic factors can regulate the responses, and peptides isolated that produce the appropriate phenotype. Screening for antagonism of vascular endothelial cell growth factor, important in angiogenesis, would also be useful.

In a preferred embodiment, the present methods are useful in screening for decreases in atherosclerosis producing mechanisms to find peptides that regulate LDL and HDL metabolism. Candidate libraries can be inserted into the appropriate cells (including hepatocytes, mononuclear leukocytes, endothelial cells) and peptides selected which lead to a decreased release of LDL or diminished synthesis of LDL, or conversely to an increased release of HDL or enhanced synthesis of HDL. Bioactive agents can also be isolated from candidate libraries which decrease the production of oxidized LDL, which has been implicated in atherosclerosis and isolated from atherosclerotic lesions. This could occur by decreasing its expression, activating reducing systems or enzymes, or blocking the activity or production of enzymes implicated in production of oxidized LDL, such as 15-lipoxygenase in macrophages.

In a preferred embodiment, the present methods are used in screens to regulate obesity via the control of food intake mechanisms or diminishing the responses of receptor signaling pathways that regulate metabolism. Bioactive agents that regulate or inhibit the responses of neuropeptide Y (NPY), cholecystokinin and galanin receptors, are particularly desirable. Candidate libraries can be inserted into cells that have these receptors cloned into them, and inhibitory peptides selected that are secreted in an autocrine manner that block the signaling responses to galanin and NPY. In a similar manner, peptides can be found that regulate the leptin receptor.

In a preferred embodiment, the present methods are useful in neurobiology applications. Candidate libraries may be used for screening for anti-apoptotics for preservation of neuronal function and prevention of neuronal death. Initial screens would be done in cell culture. One application would include prevention of neuronal death, by apoptosis, in cerebral ischemia resulting from stroke. Apoptosis is known to be blocked by neuronal apoptosis inhibitory protein (NAIP); screens for its upregulation, or effecting any coupled step could yield peptides which selectively block neuronal apoptosis. Other applications include neurodegenerative diseases such as Alzheimer's disease and Huntington's disease.

In a preferred embodiment, the present methods are useful in bone biology applications. Osteoclasts are known to play a key role in bone remodeling by breaking down "old" bone, so that osteoblasts can lay down "new" bone. In osteoporosis one has an imbalance of this process. Osteoclast overactivity can be regulated by inserting candidate libraries into these cells, and then looking for bioactive agents that produce: 1) a diminished processing of collagen by these cells; 2) decreased pit formation on bone chips; and 3) decreased release of calcium from bone fragments.

The present methods may also be used to screen for agonists of bone morphogenic proteins, hormone mimetics to stimulate, regulate, or enhance new bone formation (in a manner similar to parathyroid hormone and calcitonin, for example). These have use in osteoporosis, for poorly healing fractures, and to accelerate the rate of healing of new fractures. Furthermore, cell lines of connective tissue origin can be treated with candidate libraries and screened for their growth, proliferation, collagen stimulating activity, and/or proline incorporating ability on the target osteoblasts. Alternatively, candidate libraries can be expressed directly in osteoblasts or chondrocytes and screened for increased production of collagen or bone.

In a preferred embodiment, the present methods are useful in skin biology applications. Keratinocyte responses to a variety of stimuli may result in psoriasis, a proliferative change in these cells. Candidate libraries can be inserted into cells removed from active psoriatic plaques, and bioactive agents isolated which decrease the rate of growth of these cells.

In a preferred embodiment, the present methods are useful in the regulation or inhibition of keloid formation (i.e. excessive scarring). Candidate libraries inserted into skin connective tissue cells isolated from individuals with this condition, and bioactive agents isolated that decrease proliferation, collagen formation, or proline incorporation. Results from this work can be extended to treat the excessive scarring that also occurs in burn patients. If a common peptide motif is found in the context of the keloid work, then it can be used widely in a topical manner to diminish scarring post burn.

Similarly, wound healing for diabetic ulcers and other chronic "failure to heal" conditions in the skin and extremities can be regulated by providing additional growth signals to cells which populate the skin and dermal layers. Growth factor mimetics may in fact be very useful for this condition.

Candidate libraries can be inserted into skin connective tissue cells, and bioactive agents isolated which promote the growth of these cells under "harsh" conditions, such as low oxygen tension, low pH, and the presence of inflammatory mediators.

Cosmeceutcal applications of the present invention include the control of melanin production in skin melanocytes. A naturally occurring peptide, arbutin, is a tyrosine hydroxylase inhibitor, a key enzyme in the synthesis of melanin. Candidate libraries can be inserted into melanocytes and known stimuli that increase the synthesis of melanin applied to the cells. Bioactive agents can be isolated that inhibit the synthesis of melanin under these conditions.

In a preferred embodiment, the present methods are useful in endocrinology applications. The retroviral peptide library technology can be applied broadly to any endocrine, growth factor, cytokine or chemokine network which involves a signaling peptide or protein that acts in either an endocrine, paracrine or autocrine manner that binds or dimerizes a receptor and activates a signaling cascade that results in a known phenotypic or functional outcome. The methods are applied so as to isolate a peptide which either mimics the desired hormone (i.e., insulin, leptin, calcitonin, PDGF, EGF, EPO, GMCSF, IL1–17, mimetics) or inhibits its action by either blocking the release of the hormone, blocking its binding to a specific receptor or carrier protein (for example, CRF binding protein), or inhibiting the intracellular responses of the specific target cells to that hormone. Selection of peptides which increase the expression or release of hormones from the cells which normally produce them could have broad applications to conditions of hormonal deficiency.

In a preferred embodiment, the present methods are useful in infectious disease applications. Viral latency (herpes viruses such as CMV, EBV, HBV, and other viruses such as HIV) and their reactivation are a significant problem, particularly in immunosuppressed patients (patients with AIDS and transplant patients). The ability to block the reactivation and spread of these viruses is an important goal. Cell lines known to harbor or be susceptible to latent viral infection can be infected with the specific virus, and then stimuli applied to these cells which have been shown to lead to reactivation and viral replication. This can be followed by measuring viral titers in the medium and scoring cells for phenotypic changes. Candidate libraries can then be inserted into these cells under the above conditions, and peptides isolated which block or diminish the growth and/or release of the virus. As with chemotherapeutics, these experiments can also be done with drugs which are only partially effective towards this outcome, and bioactive agents isolated which enhance the virucidal effect of these drugs.

One example of many is the ability to block HIV-1 infection. HIV-1 requires CD4 and a co-receptor which can be one of several seven transmembrane G-protein coupled receptors. In the case of the infection of macrophages, CCR-5 is the required co-receptor, and there is strong evidence that a block on CCR-5 will result in resistance to HIV-1 infection. There are two lines of evidence for this statement. First, it is known that the natural ligands for CCR-5, the CC chemokines RANTES, MIP1a and MIP1b are responsible for CD8+mediated resistance to HIV. Second, individuals homozygous for a mutant allele of CCR-5 are completely resistant to HIV infection. Thus, an inhibitor of the CCR-5/HIV interaction would be of enormous interest to both biologists and clinicians. The extracellular anchored constructs offer superb tools for such a discovery. Into the transmembrane, epitope tagged, glycine-serine tethered constructs (ssTM V G20 E TM), one can place a cyclized peptide library of the general sequence CNNNNNNNNNNC or $C-(X)_n-C$. Then one infects a cell line that expresses CCR-5 with retroviruses containing this library. Using an antibody to CCR-5 one can use FACS to sort desired cells based on the binding of this antibody to the receptor. All cells which do not bind the antibody will be assumed contain inhibitors of this antibody binding site. These inhibitors, in the retroviral construct can be further assayed for their ability to inhibit HIV-1 entry.

Viruses are known to enter cells using specific receptors to bind to cells (for example, HIV uses CD4, coronavirus uses CD13, murine leukemia virus uses transport protein, and measles virus usesCD44) and to fuse with cells (HIV uses chemokine receptor). Candidate libraries can be inserted into target cells known to be permissive to these viruses, and bioactive agents isolated which block the ability of these viruses to bind and fuse with specific target cells.

In a preferred embodiment, the present invention finds use with infectious organisms. Intracellular organisms such as mycobacteria, *listeria, salmonella,* pneumocysts, *yersinia, leishmania, T. cruzi,* can persist and replicate within cells, and become active in immunosuppressed patents. There are currently drugs on the market and in development which are either only partially effective or ineffective against these organisms. Candidate libraries can be inserted into specific cells infected with these organisms (pre- or post-infection), and bioactive agents selected which promote the intracellular destruction of these organisms in a manner analogous to intracellular "antibiotic peptides" similar to magainins. In addition peptides can be selected which enhance the cidal properties of drugs already under investigation which have insufficient potency by themselves, but when combined with a specific peptide from a candidate library, are dramatically more potent through a synergistic mechanism. Finally, bioactive agents can be isolated which alter the metabolism of these intracellular organisms, in such a way as to terminate their intracellular life cycle by inhibiting a key organismal event.

Antibiotic drugs that are widely used have certain dose dependent, tissue specific toxicities. For example renal toxicity is seen with the use of gentamicin, tobramycin, and amphotericin; hepatotoxicity is seen with the use of INH and rifampin; bone marrow toxicity is seen with chloramphenicol; and platelet toxicity is seen with ticarcillin, etc. These toxicities limit their use. Candidate libraries can be introduced into the specific cell types where specific changes leading to cellular damage or apoptosis by the antibiotics are produced, and bioactive agents can be isolated that confer protection, when these cells are treated with these specific antibiotics.

Furthermore, the present invention finds use in screening for bioactive agents that block antibiotic transport mechanisms. The rapid secretion from the blood stream of certain antibiotics limits their usefulness. For example penicillins are rapidly secreted by certain transport mechanisms in the kidney and choroid plexus in the brain. Probenecid is known to block this transport and increase serum and tissue levels. Candidate agents can be inserted into specific cells derived from kidney cells and cells of the choroid plexus known to have active transport mechanisms for antibiotics. Bioactve agents can then be isolated which block the active transport of specific antibiotics and thus extend the serum halflife of these drugs.

In a preferred embodiment, the present methods are useful in drug toxicites and drug resistance applications. Drug toxicity is a significant clinical problem. This may manifest itself as specific issue or cell damage with the result that the drug's effectiveness is limited. Examples include myeloablation in high dose cancer chemotherapy, damage to epithelial cells lining the airway and gut, and hair loss. Specific examples include adriamycin induced cardiomyocyte death, cisplatinin-induced kidney toxicity, vincristine-induced gut motility disorders, and cyclosporin-induced kidney damage. Candidate libraries can be introduced into specific cell types with characteristic drug induced phenotypic or functional responses, in the presence of the drugs, and agents isolated which reverse or protect the specific cell type against the toxic changes when exposed to the drug. These effects may manifest as blocking the drug induced apoptosis of the cell of interest, thus initial screens will be for survival of the cells in the presence of high levels of drugs or combinations of drugs used in combination chemotherapy.

Drug toxicity may be due to a specific metabolite produced in the liver or kidney which is highly toxic to specific cells, or due to drug interactions in the liver which block or enhance the metabolism of an administered drug. Candidate libraries can be introduced into liver or kidney cells following the exposure of these cells to the drug known to produce the toxic metabolite. Bioactive agents can be isolated which alter how the liver or kidney cells metabolize the drug, and specific agents identified which prevent the generation of a specific toxic metabolite. The generation of the metabolite can be followed by mass spectrometry, and phenotypic changes can be assessed by microscopy. Such a screen can also be done in cultured hepatocytes, cocultured with readout cells which are specifically sensitive to the toxic metabolite. Applications include reversible (to limit toxicity) inhibitors of enzymes involved in drug metabolism.

Multiple drug resistance, and hence tumor cell selection, outgrowth, and relapse, leads to morbidity and mortality in cancer patents. Candidate libraries can be introduced into tumor cell lines (primary and cultured) that have demonstrated specific or multiple drug resistance. Bioactive agents can then be identified which confer drug sensitivity when the cells are exposed to the drug of interest, or to drugs used in combination chemotherapy. The readout can be the onset of apoptosis in these cells, membrane permeability changes, the release of intracellular ions and fluorescent markers. The cells in which multidrug resistance involves membrane transporters can be preloaded with fluorescent transporter substrates, and selection carried out for peptides which block the normal efflux of fluorescent drug from these cells. Candidate libraries are particularly suited to screening for peptides which reverse poorly characterized or recently discovered intracellular mechanisms of resistance or mechanisms for which few or no chemosensitizers currently exist, such as mechanisms involving LRP (lung resistance protein). This protein has been implicated in multidrug resistance in ovarian carcinoma, metastatic malignant melanoma, and acute myeloid leukemia. Particularly interesting examples include screening for agents which reverse more than one important resistance mechanism in a single cell, which occurs in a subset of the most drug resistant cells, which are also important targets. Applications would include screening for peptide inhibitors of both MRP (multidrug resistance related protein) and LRP for treatment of resistant cells in metastatic melanoma, for inhibitors of both p-glycoprotein and LRP in acute myeloid leukemia, and for inhibition (by any mechanism) of all three proteins for treating pan-resistant cells.

In a preferred embodiment, the present methods are useful in improving the performance of existing or developmental drugs. First pass metabolism of orally administered drugs limits their oral bioavailability, and can result in diminished efficacy as well as the need to administer more drug for a desired effect. Reversible inhibitors of enzymes involved in first pass metabolism may thus be a useful adjunct enhancing the efficacy of these drugs. First pass metabolism occurs in the liver, thus inhibitors of the corresponding catabolic enzymes may enhance the effect of the cognate drugs. Reversible inhibitors would be delivered at the same time as, or slightly before, the drug of interest. Screening of candidate libraries in hepatocytes for inhibitors (by any mechanism, such as protein downregulation as well as a direct inhibition of activity) of particularly problematical isozymes would be of interest. These include the CYP3A4 isozymes of cytochrome P450, which are involved in the first pass metabolism of the anti-HIV drugs saquinavir and indinavir. Other applications could include reversible inhibitors of UDP-glucuronyltransferases, sulfotransferases, N-acetyltransferases, epoxide hydrolases, and glutathione S-transferases, depending on the drug. Screens would be done in cultured hepatocytes or liver microsomes, and could involve antibodies recognizing the specific modification performed in the liver, or cocultured readout cells, if the metabolite had a different bioactivity than the untransformed drug. The enzymes modifying the drug would not necessarily have to be known, if screening was for lack of alteration of the drug.

In a preferred embodiment, the present methods are useful in immunobiology, inflammation, and allergic response applications. Selective regulation of T lymphocyte responses is a desired goal in order to modulate immune-mediated diseases in a specific manner. Candidate libraries can be introduced into specific T cell subsets (TH1, TH2, CD4+, CD8+, and others) and the responses which characterize those subsets (cytokine generation, cytotoxicity, proliferation in response to antigen being presented by a mononuclear leukocyte, and others) modified by members of the library. Agents can be selected which increase or diminish the known T cell subset physiologic response. This approach will be useful in any number of conditions, including: 1) autoimmune diseases where one wants to induce a tolerant state (select a peptide that inhibits T cell subset from recognizing a self-antigen bearing cell); 2) allergic diseases where one wants to decrease the stimulation of IgE producing cells (select peptide which blocks release from T cell subsets of specific B-cell stimulating cytokines which induce switch to IgE production); 3) in transplant patients where one wants to induce selective immunosuppression (select peptide that diminishes proliferative responses of host T cells to foreign antigens); 4) in lymphoproliferatve states where one wants to inhibit the growth or sensitize a specific T cell tumor to chemotherapy and/or radiation; 5) in tumor surveillance where one wants to inhibit the killing of cytotoxic T cells by Fas ligand bearing tumor cells; and 5) in T cell mediated inflammatory diseases such as Rheumatoid arthritis, Connective tissue diseases (SLE), Multiple sclerosis, and inflammatory bowel disease, where one wants to inhibit the proliferation of disease-causing T cells (promote their selective apoptosis) and the resulting selective destruction of target tissues (cartilage, connective tissue, oligodendrocytes, gut endothelial cells, respectively).

Regulation of B cell responses will permit a more selective modulation of the type and amount of immunoglobulin made and secreted by specific B cell subsets. Candidate libraries can be inserted into B cells and bioactve agents selected which inhibit the release and synthesis of a specific immunoglobulin. This may be useful in autoimmune diseases characterized by the overproduction of auto antibodies and the production of allergy causing antibodies, such as IgE. Agents can also be identified which inhibit or enhance the binding of a specific immunoglobulin subclass to a specific antigen either foreign of self. Finally, agents can be selected which inhibit the binding of a specific immunoglobulin subclass to its receptor on specific cell types.

Similarly, agents which affect cytokine production may be selected, generally using two cell systems. For example, cytokine production from macrophages, monocytes, etc. may be evaluated. Similarly, agents which mimic cytokines, for example erythropoetin and IL1–17, may be selected, or agents that bind cytokines such as TNF-α, before they bind their receptor.

Antigen processing by mononuclear leukocytes (ML) is an important early step in the immune system's ability to recognize and eliminate foreign proteins. Candidate agents can be inserted into ML cell lines and agents selected which alter the intracellular processing of foreign peptides and sequence of the foreign peptide that is presented to T cells by MLs on their cell surface in the context of Class II MHC. One can look for members of the library that enhance immune responses of a particular T cell subset (for example, the peptide would in fact work as a vaccine), or look for a library member that binds more tightly to MHC, thus displacing naturally occurring peptides, but nonetheless the agent would be less immunogenic (less stimulatory to a specific T cell clone). This agent would in fact induce immune tolerance and/or diminish immune responses to foreign proteins. This approach could be used in transplantation, autoimmune diseases, and allergic diseases.

The release of inflammatory mediators (cytokines, leukotrienes, prostaglandins, platelet activating factor, histamine, neuropeptides, and other peptide and lipid mediators) is a key element in maintaining and amplifying aberrant immune responses. Candidate libraries can be inserted into MLs, mast cells, eosinophils, and other cells participating in a specific inflammatory response, and bioactive agents selected which inhibit the synthesis, release and binding to the cognate receptor of each of these types of mediators.

In a preferred embodiment, the present methods are useful in biotechnology applications. Candidate library expression in mammalian cells can also be considered for other pharmaceutical-related applications, such as modification of protein expression, protein folding, or protein secretion. One such example would be in commercial production of protein pharmaceuticals in CHO or other cells. Candidate libraries resulting in bioactive agents which select for an increased cell growth rate (perhaps peptides mimicking growth factors or acting as agonists of growth factor signal transduction pathways), for pathogen resistance (see previous section), for lack of sialylation or glycosylation (by blocking glycotransferases or rerouting trafficking of the protein in the cell), for allowing growth on autoclaved media, or for growth in serum free media, would all increase productivity and decrease costs in the production of protein pharmaceuticals.

Peptides displayed on the surface of circulating cells can be used as tools to identify organ, tissue, and cell specific peptide targeting sequences. Any cell introduced into the bloodstream of an animal expressing a library targeted to the cell surface can be selected for specific organ and tissue targeting. The bioactive agent sequence identified can then be coupled to an antibody, enzyme, drug, imaging agent or substance for which organ targeting is desired.

Other agents which may be selected using the present invention include: 1) agents which block the activity of transcription factors, using cell lines with reporter genes; 2) agents which block the interaction of two known proteins in cells, using the absence of normal cellular functions, the mammalian two hybrid system or fluorescence resonance energy transfer mechanisms for detection; and 3) agents may be identified by tethering a candidate peptide to a protein binding region to allow interactions with molecules sterically close, i.e. within a signalling pathway, to localize the effects to a functional area of interest.

All references cited herein are incorporated by reference in their entirety. The following example is provided to further illustrate an embodiment of the present invention, but is in no way intended to be construed as defining the limits of the invention.

EXAMPLE 1

A Random Directionally Cloned Jurkat cDNA Library pTRAsf Random Directionally Cloned cDNA Library Construction First-strand cDNA Synthesis:

3 ug PolyA+ RNA+(Jurkat) and 0.8 ug $CCN_6$ random primer (5'-CCNNNNNN-3', where N is any nucleotide) was denatured at 70 c for 5 min., cool down on ice for 2 min. The reverse transcription reaction was carried out at 38 c for 1 hour 15 min. in a final volume of 20 ul with 2 ul 10× First-strand Buffer, 75 units of Stratascript Reverse Transcriptase (Stratagene) and 2.5 ul of 10 mM dNTP each.

Second-Strand cDNA Synthesis:

The second-strand cDNA synthesis reaction was carried out in a final volume of 150 ul with 3 units of RNase, 70 units of DNA Polymerase 1, 30 ul 5×Second Strand Buffer (100 mM Tris-HCl PH7.5, 50 mM KCl, 25 mM $MgCl_2$, 0.75 mM β-NAD and 50 mM $(NH_4)_2SO_4$) and 4 ul of dNTP each. The ds cDNA was then repaired with T4 DNA Polymerase at 37 c 0.5 hour. Extracted the ds cDNA once with Phenol: Chloroform:isoamyl alcohol (25:24:1), Chloroform once, precipitate with ethanol and 4 M $NH_4Oac$.

Adapter Ligation:

5 ul of 100 uM Sfi1ANB adapter was ligated to blunt-ended ds cDNA at 16 c for overnight. Extracted the cDNA once with phenol: Chloroform: isoamyl alcohol (25:24:1), chloroform once, precipitate with ethanol and $NH_4Oac$.

The cDNA were digested by Sfi1 enzyme at 50 c for 4 hours.

cDNA size selected by gel purification to remove cDNA smaller than 500 bp and cloned into Sfi1enzyme digested pTRAsf (Rigel's) vector.

The ligated plasmid was transformed into electro-competent cells *E. Coli* DH10B (Invitrogene) to obtain a random directional cDNA library of $3 \times 10^6$ independent cDNA clones.

Analysis of recombinant clones and inserts size by PCR inserts screening using 5'+3' TRA primer.

We claim:

1. A composition comprising combinable reagents for making a directionally cloned cDNA library, comprising:
   a primer having at its 5' terminus a first nucleotide sequence of a 3' portion of a restriction site for an infrequently cutting restriction endonuclease; and
   a double stranded adaptor having a second nucleotide sequence of a 5' end of said restriction site for said infrequently cutting restriction endonuclease.

2. The composition of claim 1, wherein said first and second nucleotide sequences, when ligated together, form a complete sequence of a restriction site for said infrequently cutting restriction endonuclease.

3. The composition of claim 1, wherein said infrequently cutting restriction endonuclease is Sfi1, BstAP1, PfiM1, Mwo1 or AlwN1.

4. The composition of claim 3, wherein said infrequently cutting restriction endonuclease is Sfi1.

5. The composition of claim 1, wherein said primer contains a CC at its 5' terminus.

6. The composition of claim 1, wherein said primer is a random primer.

7. The composition of claim 6, wherein said random primer contains 4 to 10 random nucleotides at its 3' end.

8. The composition of claim 1, wherein said primer comprises oligodT.

* * * * *